(12) United States Patent
Kuo et al.

(10) Patent No.: US 8,524,740 B2
(45) Date of Patent: Sep. 3, 2013

(54) SYNTHESIS AND ANTICANCER ACTIVITY OF ARYL AND HETEROARYL-QUINOLIN DERIVATIVES

(75) Inventors: Sheng-Chu Kuo, Taichung (TW); Kuo-Hsiung Lee, Chapel Hill, NC (US); Li-Jiau Huang, Taichung (TW); Li-Chen Chou, Taichung (TW); Tian-Shung Wu, Tainan (TW); Tzong-Der Way, Taichung (TW); Jing-Gung Chung, Taichung (TW); Jai-Sing Yang, Taichung (TW); Chi-Hung Huang, Taoyuan County (TW); Meng-Tung Tsai, Taichung (TW)

(73) Assignee: Tairx, Inc., Taipei (TW)

( * ) Notice: Subject to any disclaimer, the term of this patent is extended or adjusted under 35 U.S.C. 154(b) by 169 days.

(21) Appl. No.: 13/181,978

(22) Filed: Jul. 13, 2011

(65) Prior Publication Data

US 2012/0015908 A1    Jan. 19, 2012

Related U.S. Application Data

(60) Provisional application No. 61/364,760, filed on Jul. 15, 2010.

(51) Int. Cl.
  *A61K 31/04*    (2006.01)
  *C07D 215/04*    (2006.01)

(52) U.S. Cl.
  USPC .............. 514/313; 514/291; 546/156; 546/90

(58) Field of Classification Search
  USPC .......................... 546/159, 90; 514/313, 291
  See application file for complete search history.

(56) References Cited

U.S. PATENT DOCUMENTS

| | | | | |
|---|---|---|---|---|
| 6,897,316 B2 * | 5/2005 | Kuo et al. | .................. | 546/157 |
| 2009/0163545 A1 * | 6/2009 | Goldfarb | ..................... | 514/312 |

FOREIGN PATENT DOCUMENTS

| | | | |
|---|---|---|---|
| WO | 9402145 A2 | | 2/1994 |
| WO | 9610563 A1 | | 4/1996 |
| WO | 0226730 A2 | | 4/2002 |
| WO | 2008070176 | * | 6/2008 |
| WO | 2008070176 A1 | | 6/2008 |

OTHER PUBLICATIONS

Kuo, CA149:54096, abstract only of WO2008070176, 2008.*
Ward, CA152:37360, abstract only of Tetrahedron Letters, 50(47), pp. 6494-6497, 2009.*
Chang et al "Design and Synthesis of 2-(3-Benzo[b]thienyl)-6,7-methylenedioxyquinolin-4-one Analogues as Potent Antitumor Agents that Inhibit Tubulin Assembly" J. Med. Chem. 2009, 52, 4883-4891.
Li et al. "Antitumor Agents. 150.t2',3',4',5', 5,6,7-Substituted 2-Phenyl-4-quinolones and Related Compounds: Their Synthesis, Cytotoxicity, and Inhibition of Tubulin Polymerization" J. Med. Chem. 1994,37, 1126-1135.
PCT/US2011/043985, search report and written opinion. Oct. 10, 2011.

* cited by examiner

*Primary Examiner* — D M Seaman
(74) *Attorney, Agent, or Firm* — Hsiu-Ming Saunders; Intellectual Property Connections, Inc.

(57) ABSTRACT

A compound of Formula I is disclosed as follows:

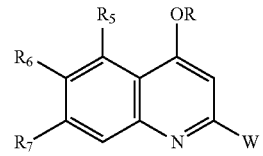

or a pharmaceutically acceptable salt, prodrug, solvate, or metabolite thereof, wherein R is hydrogen, $P(=O)(OH)_2$, $P(=O)(O(C_1-C_{18})$alkylene $(C_6-C_{20})$aryl$)_2$, $P(=O)(OH)(OM)$, $P(=O)(OM)_2$, $P=O(O_2M)$, $S(=O)(OH)_2$, $S(=O)(O(C_1-C_{18})$alkylene$(C_6-C_{20})$aryl$)_2$, $S(=O)(OH)(OM)$, $S(=O)(OM)_2$;

M is a monovalent or divalent metal ion, or alkylammonium ion;

W is $(C_6-C_{20})$aryl, $(C_6-C_{20})$heteroaryl, $(C_1-C_{18})$alkyl$(C_6-C_{20})$aryl, $(C_1-C_{18})$alkyl$(C_6-C_{20})$heteroaryl, hydroxy $(C_6-C_{20})$aryl, hydroxy$(C_6-C_{20})$heteroaryl, $(C_1-C_{18})$ alkoxy$(C_6-C_{20})$aryl, $(C_1-C_{18})$alkoxy$(C_6-C_{20})$ heteroaryl, $(C_1-C_{18})$alkylenedioxy$(C_6-C_{20})$aryl, $(C_1-C_{18})$alkylenedioxy$(C_6-C_{20})$heteroaryl, halo$(C_6-C_{20})$ aryl, halo$(C_6-C_{20})$heteroaryl, $(C_1-C_{18})$alkylamino$(C_6-C_{20})$aryl, $(C_1-C_{18})$alkylamino$(C_6-C_{20})$heteroaryl, $(C_1-C_{18})$cycloalkylamino$(C_6-C_{20})$aryl, or $(C_1-C_{18})$ cycloalkylamino$(C_6-C_{20})$heteroaryl, and their $OR_8$ substutes;

$R_5$ is $(C_1-C_{18}$alkoxy, hydrogen, hydroxyl, O—$(C_1-C_{18})$ alkyl$(C_6-C_{20})$aryl, halo or $OR_8$, or $R_5$ and $R_6$ are $(C_1-C_{18})$dioxy provided that $R_7$ is hydrogen;

$R_6$ is hydroxyl, O—$(C_1-C_{18})$alkyl$(C_6-C_{20})$aryl, halo or $OR_8$, $(C_1-C_{18})$alkoxy, $(C_1-C_{18})$alkylamino, or $(C_1-C_{18})$ cycloalkylamino, or $R_6$ and $R_7$ are $(C_1-C_{18})$dioxy provided that $R_5$ is hydrogen;

$R_7$ is hydrogen, halo or $OR_8$, hydroxyl, or O—$(C_1-C_{18})$ alkyl$(C_6-C_{20})$aryl; and $R_8$ is $P(=O)(OH)_2$, $P(=O)(O(C_1-C_{18})$alkyl$(C_6-C_{20})$ aryl$)_2$, $P(=O)(OH)(OM)$, or $P(=O)(OM)_2$, $P=O$ $(O_2M)$.

20 Claims, 12 Drawing Sheets

SYNTHESIS AND ANTICANCER ACTIVITY OF ARYL AND HETEROARYL-QUINOLIN DERIVATIVES

REFERENCE TO RELATED APPLICATION

The present application claims the priority to U.S. Provisional Application Ser. No. 61/364,760, filed Jul. 15, 2010, which is herein incorporated by reference in its entirety.

FIELD OF THE INVENTION

The present invention relates generally to derivatives and analogues of aryl and heteroaryl-quinolin, and more specifically to synthesis and use of aryl and heteroaryl-quinolin derivatives and analogues for anticancer activities.

BACKGROUND OF THE INVENTION

A series of substituted 2-phenylquinolin-4-ones (2-PQs) have been previously synthesized and identified as new anticancer agents. Through the process of structure-activity relationship (SAR) establishment, it was discovered that many of these compounds had potent cytotoxicity. In a recent in vivo evaluation of a series of 2-PQs with potent cytotoxicity, excellent antitumor activity was identified in 2-(2-fluorphenyl)-6,7-methylenedioxyquinolin-4-one (CHM-2133) and its phosphate derivative (CHM-2133-P) (FIG. 1). See WO2008/070176A1 and Yu-Hsun Chang et al. (2009) "Design and Synthesis of 2-(3-Benzo[b]thienyl)-6,7-methylenedioxyquinolin-4-one Analogues as Potent Antitumor Agents that Inhibit Tubulin Assembly" *J. Med. Chem.* 52, 4883-4891, each of which is herein incorporated by reference in its entirety. There is still a need for discovery of more potential anticancer compounds.

SUMMARY OF THE INVENTION

In one aspect, the invention relates to a compound of Formula I:

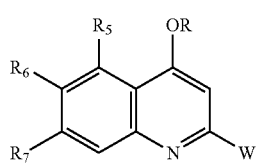

Formula I or a pharmaceutically acceptable salt, prodrug, solvate, or metabolite thereof, wherein R is hydrogen, $P(=O)(OH)_2$, $P(=O)(O(C_1-C_{18})$alkylene$(C_6-C_{20})$aryl$)_2$, $P(=O)(OH)(OM)$, $P(=O)(OM)_2$, $P=O(O_2M)$, $S(=O)(OH)_2$, $S(=O)(O(C_1-C_{18})$alkylene$(C_6-C_{20})$aryl$)_2$, $S(=O)(OH)(OM)$, $S(=O)(OM)_2$;

M is a monovalent and divalent (ex: Mg, Ca) metal ion, or alkylammonium ion (ex: $N^{\oplus}R$);

W is $(C_6-C_{20})$aryl, $(C_6-C_{20})$heteroaryl, $(C_1-C_{18})$alkyl$(C_6-C_{20})$aryl, $(C_1-C_{18})$alkyl$(C_6-C_{20})$heteroaryl, hydroxy$(C_6-C_{20})$aryl, hydroxy$(C_6-C_{20})$heteroaryl, $(C_1-C_{18})$alkoxy$(C_6-C_{20})$aryl, $(C_1-C_{18})$alkoxy$(C_6-C_{20})$heteroaryl, $(C_1-C_{18})$alkylenedioxy$(C_6-C_{20})$aryl, $(C_1-C_{18})$alkylenedioxy$(C_6-C_{20})$heteroaryl, halo$(C_6-C_{20})$aryl, halo$(C_6-C_{20})$heteroaryl, $(C_1-C_{18})$alkylamino$(C_6-C_{20})$aryl, $(C_1-C_{18})$alkylamino$(C_6-C_{20})$heteroaryl, $(C_1-C_{18})$cycloalkylamino$(C_6-C_{20})$aryl, or $(C_1-C_{18})$cycloalkylamino$(C_6-C_{20})$heteroaryl, and their $OR_8$ substutes;

$R_5$ is $(C_1-C_{18})$alkoxy, hydrogen, hydroxyl, $O-(C_1-C_{18})$alkyl$(C_6-C_{20})$aryl, halo or $OR_8$, or $R_5$ and $R_6$ are $(C_1-C_{18})$dioxy provided that $R_7$ is hydrogen;

$R_6$ is hydroxyl, $O-(C_1-C_{18})$alkyl$(C_6-C_{20})$aryl, halo, $OR_8$, $(C_1-C_{18})$alkoxy, $(C_1-C_{18})$alkylamino, or $(C_1-C_{18})$cycloalkylamino, or $R_6$ and $R_7$ are $(C_1-C_{18})$dioxy provided that $R_5$ is hydrogen;

$R_7$ is hydrogen, halo or $OR_8$, hydroxyl, or $O-(C_1-C_{18})$alkyl$(C_6-C_{20})$aryl; and $R_8$ is $P(=O)(OH)_2$, $P(=O)(O(C_1-C_{18})$alkyl$(C_6-C_{20})$aryl$)_2$, $P(=O)(OH)(OM)$, or $P(=O)(OM)_2$, $P=O(O_2M)$.

In one embodiment of the invention, the aforementioned class of the compound is restricted with the proviso that if R5 is hydroxyl, then R6 is not (Cl)alkoxy and W is not 3-fluorophenyl.

In another embodiment of the invention, R5 is hydroxyl, R6 is (Cl)alkoxy and W is 3-fluorophenyl.

In another aspect, the invention relates to a composition comprising a compound as aforementioned and a pharmaceutically acceptable carrier.

Further in another aspect, the invention relates to a method for treating a tumor disease comprising administering to a subject in need thereof an effective amount of a composition as aforementioned. The administering step may be performed in vivo or in vitro. In one embodiment, the subject is a mammal.

Yet in another aspect, the invention relates to a process for preparing a compound as aforementioned comprising reacting a compound of Formula II

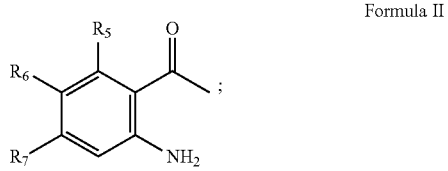

Formula II wherein $R_5$ is $(C_1-C_{18})$alkoxy, hydrogen, hydroxyl, $O-(C_1-C_{18})$alkyl$(C_6-C_{20})$aryl, or $OR_8$ or $R_5$ and $R_6$ are $(C_1-C_{18})$dioxy provided that $R_7$ is hydrogen;

$R_6$ is hydroxyl, $(C_1-C_{18})$alkoxy, $O-(C_1-C_{18})$alkyl$(C_6-C_{20})$aryl, $(C_1-C_{18})$alkylamino, or $(C_1-C_{18})$cycloalkylamino or $R_6$ and $R_7$ are $(C_1-C_{18})$dioxy provided that $R_5$ is hydrogen;

$R_7$ is hydrogen, hydroxyl, or $O-(C_1-C_{18})$alkyl$(C_6-C_{20})$aryl; and $R_8$ is hydrogen; with a compound of Formula III

Formula III in the presence of a base; wherein W is 2-fluorophenyl, 3-fluorophenyl, 4-fluorophenyl, benzo[d][1,3]dioxol-4-yl, 2,3-dimethoxyphenyl, 2,5-dimethoxyphenyl, 2-methoxyphenyl, 4-methoxyphenyl, 2-hydroxyphenyl, 3-hydroxyphenyl, 4-hydroxyphenyl, 2-benzyloxyphenyl, 3-benzyloxyphenyl, 4-benzyloxyphenyl, 4-benzyloxy-3-methoxyphenyl, 3-benzyloxy-5-methoxyphenyl, 4-hydroxy-3-methoxyphenyl, 5-hydroxy-2-methoxyphenyl, 2,5- dihydroxyphenyl, benzo[b]thiophen-3-yl, benzo[b]thiophen-2-yl, benzo[b]furan-3-yl, naphtha-1-yl, naphtha-2-yl, quinolin-4-yl, quinolin-3-yl, quinolin-2-yl, quinolin-5-yl, or anthracen-1-yl to afford a compound of Formula IV

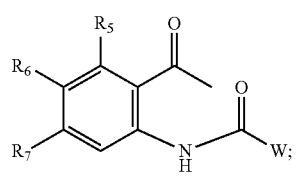

Formula IV wherein
R is hydrogen;
W is 2-fluorophenyl, 3-fluorophenyl, 4-fluorophenyl, benzo[d][1,3]dioxol-4-yl, 2,3-dimethoxyphenyl, 2,5-dimethoxyphenyl, 2-methoxyphenyl, 4-methoxyphenyl, 2-hydroxyphenyl, 3-hydroxyphenyl, 4-hydroxyphenyl, 2-benzyloxyphenyl, 3-benzyloxyphenyl, 4-benzyloxyphenyl, 4-benzyloxy-3-methoxyphenyl, 3-benzyloxy-5-methoxyphenyl, 4-hydroxy-3-methoxyphenyl, 5-hydroxy-2-methoxyphenyl, 2,5-dihydroxyphenyl, benzo[b]thiophen-3-yl, benzo[b]thiophen-2-yl, benzo[b]furan-3-yl, naphtha-1-yl, naphtha-2-yl, quinolin-4-yl, quinolin-3-yl, quinolin-2-yl, quinolin-5-yl, or anthracen-1-yl;

$R_5$ is hydrogen, methoxy, hydroxyl, O-benzyl or $OR_8$, or $R_5$ and $R_6$ are methylenedioxy provided that $R_7$ is hydrogen;

$R_6$ is N,N-dimethylamino, hydroxyl, O-benzyl, methoxy, N-morpholino, or N-pyrrolindino, or $R_6$ and $R_7$ are methylenedioxy provided that $R_5$ is hydrogen;

$R_7$ is hydrogen, hydroxyl, or O-benzyl; and $R_8$ is hydrogen; and reacting a compound of Formula IV with a base to afford the compound of Formula I.

The process may further comprise dealkylating the compound of Formula I. The dealkylated or non-dealkylated compound of Formula I may further react with tetrabenzylpyrophosphate (Method A) or dibenzylphosphite (Method B) to afford the compound of Formula I, wherein R is P(=O)(OCH$_2$Ph)$_2$, which treated with alcohol provided monophosphate. The monophosphoric acid were obtained by catalytic hydrogenation of the monophosphate. The monophosphoric acid may further react with a metal carbonate to afford the compound of Formula I, wherein R is P(=O)(OH)(OM), or P(=O)(OM)$_2$, in which M is a monovalent metal ion.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
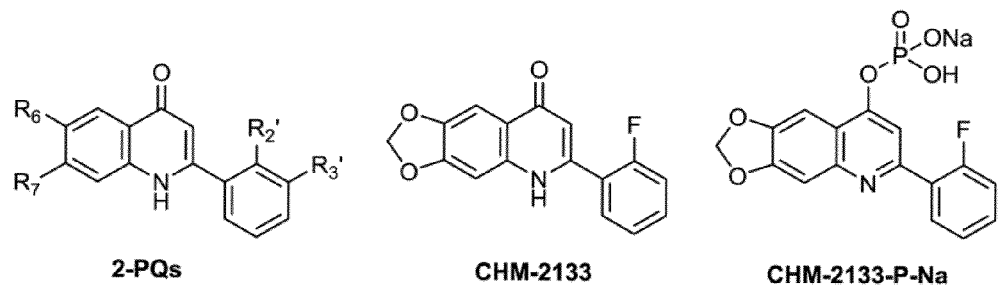
FIG. 1 shows the structures of substituted 2-phenylquinolin-4-ones (2-PQs), CHM-2133 and CHM-2133-P—Na.

One of ordinary skill in the art would readily appreciate that the pharmaceutical formulations and methods described herein can be prepared and practiced by applying known procedures in the pharmaceutical arts. These include, for example, unless otherwise indicated, conventional techniques of pharmaceutical sciences including pharmaceutical dosage form design, drug development, pharmacology, of organic chemistry, and polymer sciences. See generally, for example, Remington: The Science and Practice of Pharmacy, 21" edition, Lippincott, Williams & Wilkins, (2005).

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used/for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "and/or" refers to any one of the items, any combination of the items, or all of the items with which this term is associated.

The singular forms "a," "an," and "the" include plural reference unless the context clearly dictates otherwise. The claims may be drafted to exclude any optional element. As such, this statement is intended to serve as antecedent basis for use of such exclusive terminology as "solely," "only," and the like in connection with the recitation of claim elements, or use of a "negative" limitation.

Specific and preferred values listed below for radicals, substituents, and ranges, are for illustration only; they do not exclude other defined values or other values within defined ranges for the radicals and substituents.

The term "administration" refers to a method of placing a device to a desired site. The placing of a device can be by any pharmaceutically accepted means such as by swallowing, retaining it within the mouth until the drug has been dispensed, placing it within the buccal cavity, inserting, implanting, attaching, etc. These and other methods of administration are known in the art.

The term "anti-cancer agent" refers to an agent that either inhibits the growth of cancerous cells, or causes the death of cancerous cells. Known anti-cancer agents include, e.g., nucleotide and nucleoside analogs, adjunct antineoplastic agents, alkylating agents, etc. See, *Physician's Desk Reference*, 55th Edition, Medical Economics, Montvale, N.J., USA (2001).

The term "amino" refers to —$NH_2$. The amino group can be optionally substituted as defined herein for the term "substituted." The term "alkylamino" refers to —$NR_2$, wherein at least one R is alkyl and the second R is alkyl or hydrogen. The term "acylamino" refers to N(R)C(=O)R, wherein each R is independently hydrogen, alkyl, or aryl.

The term "alkyl" refers to a $C_1$-$C_{18}$ hydrocarbon containing normal, secondary, tertiary or cyclic carbon atoms. Examples are methyl, ethyl, 1-propyl, 2-propyl, 1-butyl, 2-methyl-1-propyl(iso-butyl, —$CH_2CH(CH_3)_2$), 2-butyl (sec-butyl, —$CH(CH_3)CH_2CH_3$), 2-methyl-2-propyl(tert-butyl, —$C(CH_3)_3$), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl.

The alkyl can be a monovalent hydrocarbon radical, as described and exemplified above, or it can be a divalent hydrocarbon radical (i.e., alkylene).

The alkyl can optionally be substituted with one or more alkoxy halo, haloalky hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoramethoxy, carboxy, carboxyalkyl, keto, thioxo, alkylthio, alkylsulfinyl, alkyisulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl or hydroxy. The alkyl can optionally be interrupted with one or more non-peroxide oxy (—O—), thio (—S—), amine (—N(H)—), methylene dioxy (—$OCH_2O$—), carbonyl (—C(=O)—), carboxy (—C(=O)O—), carbonyldioxy (—OC(=O)O—), carboxylato (—OC(=O)—), imino (C=NH), sulfinyl (SO) or sulfonyl ($SO_2$). Additionally, the alkyl can optionally be at least partially unsaturated, thereby providing an alkenyl.

The term "alkylene" refers to a saturated, branched or straight chain or cyclic hydrocarbon radical of 1-18 carbon atoms, and having two monovalent radical centers derived by the removal of two hydrogen atoms from the same or different carbon atoms of a parent alkane. Typical alkylene radicals include, but are not limited to: methylene (—$CH_2$—) 1,2-ethylene (—$CH_2CH_2$—), 1,3-propylene (—$CH_2CH_2CF_{12}$—), 1,4-butylene (—$CH_2CH_2CH_2CH_2$—), and the like.

The alkylene can optionally be substituted with one or more alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamayl, sulfino, sulfo, sulfoamino, thiasulfo, $NR^xR^y$ and/or $COOR^x$, wherein each $R^x$ and $R^y$ are independently H, alkyl, alkenyl, aryl, heteroaryl, heterocycle, cycloalkyl or hydroxy. Additionally, the alkylene can optionally be interrupted with one or more non-peroxide oxy (—O—), thio (—S—), amine (—N(H)—), methylene dioxy (—$OCH_2O$—), carbonyl (—C(=0)—), carboxy (—C(=O)O—), carbonyldioxy (—OC(=O)O—), carboxylato (—OC(=O)—), imine (C=NH), sulfinyl (SO) or sulfonyl ($SO_2$). Moreover, the alkylene can optionally be at least partially unsaturated, thereby providing an alkenylene.

The term "alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethenylene (—CH=CH—).

The alkenylene can optionally be substituted with one or more alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiasulfo, $NR^xR^y$ and/or $COOR^x$, wherein each $R^x$ and $R^y$ are independently H, alkyl, alkenyl, aryl, heteroaryl, heterocycle, cycloalkyl or hydroxy. Additionally, The alkenylene can optionally be interrupted with one or more non-peroxide oxy (—O—), thio (—S—), amine (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) or sulfonyl (SO$_2$).

The term "alkoxy" refers to the group alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like.

The alkoxy can optionally be substituted with one or more halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like. The aryl can optionally be a divalent radical, thereby providing an arylene.

The aryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

The term "carbocycle" refers to a saturated, unsaturated or aromatic ring having 3 to 8 carbon atoms as a monocycle, 7 to 12 carbon atoms as a bicycle, and up to about 30 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. The carbocycle can be optionally substituted as described above for alkyl groups.

The term "carboxyl" refers to —COOH.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

The term "chemically feasible" refers to a bonding arrangement or a compound where the generally understood rules of organic structure are not violated; for example a structure within a definition of a claim that would contain in certain situations a pentavalent carbon atom that would not exist in nature would be understood to not be within the claim.

When a substituent is specified to be an atom or atoms of specified identity, "or a bond", a configuration is referred to when the substituent is "a bond" that the groups that are immediately adjacent to the specified substituent are directly connected to each other by a chemically feasible bonding configuration.

The phrase "compounds of the disclosure" refer to compounds of Formula I and pharmaceutically acceptable enantiomers, diastereomers, and salts thereof. Similarly, references to intermediates, are meant to embrace their salts where the context so permits.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The cycloalkyl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

The cycloalkyl can optionally be at least partially unsaturated, thereby providing a cycloalkenyl. Additionally, the cycloalkyl can optionally be a divalent radical, thereby providing a cycloalkylene.

The term "delivery" refers to the release of a drug from a device comprising that drug into an environment surrounding the device. The environment into which the drug so released may or may not be the ultimate site of activity for that drug. In some instances, the released drug may need to be transported to its ultimate site of activity.

The term "derivative or analogue" of a compound refers to a chemically modified compound wherein the chemical modification takes place at one or more functional groups of the compound and for on an aromatic, alicyclic, or heterocyclic structures, when present. The derivative or analogue however is expected to retain the pharmacological activity of the compound from which it is derived.

The term "an effective amount" refers to an amount sufficient to effect beneficial or desired results. An effective amount can be administered in one or more administrations, applications, or dosages. Determination of an effective amount for a given administration is well within the ordinary skill in the pharmaceutical arts.

The term "exchanged" is intended to indicate that in between two or more adjacent carbon atoms, and the hydrogen atoms to which they are attached (e.g., methyl ($CH_3$), methylene ($CH_2$), or methine (CH)), indicated in the expression using "interrupted" is inserted with a selection from the indicated group(s), provided that the each of the indicated atoms' normal valency is not exceeded, and that the interruption results in a stable compound. Such suitable indicated groups include, e.g with one or more non-peroxide oxy (—O—), thio (—S—), amine (—N(H)—), methylene dioxy (—$OCH_2O$—), carbonyl (—C(=O)—), carboxy (—C(=O)O—), carbonyldioxy (—OC(=O)O—), carboxylato (—OC(=O)—), imino (C=NH), sulfinyl (SO) and sulfonyl ($SO_2$).

The term "halo" refers to fluoro, chloro, bromo, and iodo. Similarly, the term "halogen" refers to fluorine, chlorine, bromine, and iodine.

The term "haloalkyl" refers to alkyl as defined herein substituted by 1-4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted. The heteroaryl can optionally be a divalent radical, thereby providing a heteroarylene.

Examples at heteroaryl groups include, but are not limited to, 2H-pyrrolyl, 3H-indolyl, 4H-quinolizinyl, 4H-carbazolyl, acridinyl, benzo[b]thienyl, benzothiazolyl, β-carbolinyl, carbazolyl, chromenyl, cinnaolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridy pyrimidinyl, pyrrolyl, quinazoliny, quinoly quinoxalinyl, thiadiazotyl, thianthrenyl, thiazolyl, thienyl, triazolyl, and xanthenyl. In one embodiment the term "heteroaryl" denotes a monocyclic aromatic ring containing five or six ring atoms containing, carbon and 1, 2, 3, or 4 heteroatoms independently selected from the group non-peroxide oxygen, sulfur, and N(Z) wherein Z is absent or is H, O, alkyl, phenyl, or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The heteroaryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

The term "heterocycle" or "heterocyclyl" refers to a saturated or partially unsaturated ring system, containing at least one heteroatom selected from the group oxygen, nitrogen, and sulfur, and optionally substituted with alkyl, or C(=O)$OR^b$, wherein $R^b$ is hydrogen or alkyl. Typically heterocycle is a monocyclic, bicyclic, or tricyclic group containing one or more heteroatoms selected from the group oxygen, nitrogen, and sulfur. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine. The heterocycle can optionally be a divalent radical, thereby providing a heterocyclene.

The heterocycle can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "hydrate" refers to the complex where the solvent molecule is water.

The term "include," "for example," "such as," and the like are used illustratively and are not intended to limit the present invention.

The term "interrupted" indicates that another group is inserted between two adjacent carbon atoms (and the hydrogen atoms to which they are attached (e.g., methyl ($CH_3$), methylene ($CH_2$) or methine (CH))) of a particular carbon chain being referred to in the expression using the term "interrupted, provided that each of the indicated atoms' normal valency is not exceeded, and that the interruption results in a stable compound. Suitable groups that can interrupt a carbon chain include, e.g., with one or more non-peroxide oxy (—O—), thio (—S—), amine (—N(H)—), methylene dioxy (—$OCH_2O$—), carbonyl (—C(=O)—), carboxy (—C(=O)O—), carbonyldioxy (—OC(=O)O—), carboxylato (—OC(=O)—), imine (C=NH), sultinyl (SO) and sulfonyl ($SO_2$). Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number will be determined as set forth above.

The term "metabolite" refers to any compound of the formula (I) produced in vivo or in vitro from the parent drug, or its prodrugs. The term "molecular weight" refers to a weight-average molecular weight, as is well known in the art. The term "oxo" refers to =O.

The term "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio. Several pharmaceutically acceptable ingredients are known in the art and official publications such as *The United States Pharmacoepia* describe the analytical criteria to assess the pharmaceutical acceptability of numerous ingredients of interest.

The term "pharmaceutically acceptable salts" refers to ionic compounds, wherein a parent non-ionic compound is modified by making acid or base salts thereof. Examples of pharmaceutically acceptable salts include mineral or organic acid salts of basic residues such as amines; alkali or organic salts of acidic residues such as carboxylic acids; and the like. The pharmaceutically acceptable salts include conventional non-toxic salts and quaternary ammonium salts of the parent compound formed, for example, from non-toxic inorganic or organic acids. Non-toxic salts can include those derived from inorganic acids such as hydrochloric, hydrobromic, hydroiodic, sulfuric, sulfamic, phosphoric, nitric and the like. Salts prepared from organic acids can include those such as acetic, 2-acetoxybenzoic, ascorbic, benzenesulfonic, benzoic, citric, ethanesulfonic, ethane disulfonic, formic, fumaric, gentisinic, glucaronic, gluconic, glutamic, glycolic, hydroxymaleic, isethionic, isonicotinic, lactic, maleic, malic, mesylate or methanesulfonic, oxalic, pamoic (1,1'-methylene-bis-(2-hydroxy-3-naphthoate)), pantothenic, phenylacetic, propionic, salicylic, sulfanilic, toluenesulfonic, stearic, succinic, tartaric, bitartaric, and the like. Certain compounds can form pharmaceutically acceptable salts with various amino acids. For a review on pharmaceutically acceptable salts, see, e.g., Berge et al., *J. Pharm. Sci.* 1977, 66(1), 1-19, which is incorporated herein by reference.

The pharmaceutically acceptable salts of the compounds described herein can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of many suitable salts are found in *Remington: The Science and Practice of Pharmacy*, $21^{st}$ edition, Lippincott, Williams & Wilkins, (2005).

It will be appreciated by those skilled in the art that compounds useful in the disclosed subject matter having a chiral center may exist in and be isolated in optically active and racemic forms. Some compounds may exhibit polymorphism. It is to be understood that the presently disclosed subject matter encompasses any racemic, optically-active, polymorphic, or stereoisomeric form, or mixtures thereof, of a compound of the presently disclosed subject matter, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anticancer activity using the standard tests described herein, or using other similar tests which are well known in the art.

One diastereomer of a compound disclosed herein may display superior activity compared with the other. When required, separation of the racemic material can be achieved by HPLC using a chiral column or by a resolution using a resolving agent such as camphonic chloride as in Tucker et al., *J. Med. Chem.*, 37, 2437 (1994). A chiral compound described herein may also be directly synthesized using a chiral catalyst or a chiral ligand, e.g., Huffman et al., *J. Org. Chem.*, 60:1590 (1995).

The terms "prevent," "preventative," "prevention," "protect," and "protection" refer to medical procedures that keep the malcondition from occurring in the first place. The terms mean that there is no or a lessened development of disease or disorder where none had previously occurred, or no further disorder or disease development if there had already been development of the disorder or disease.

The term "prodrug" refers to any pharmaceutically acceptable form of compound of the formula I, which, upon administration to a patient, provides a compound of the formula I. Pharmaceutically acceptable prodrugs refer to a compound that is metabolized, for example hydrolyzed or oxidized, in the host to form a compound of the formula I. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The prodrug may be prepared with the objective(s) of improved chemical stability, improved patient acceptance and compliance, improved bioavailability, prolonged duration of action, improved organ selectivity (including improved brain penetrance), improved formulation (e.g., increased hydrosolubility), and/or decreased side effects (e.g., toxicity). See e.g. T. Higuchi and V. Stella, "Prodrugs as Novel Delivery Systems", Vol. 14 of the A.C.S. Symposium Series; Bioreversible Carriers in Drug Design, ed. Edward B. Roche, American Pharmaceutical Association and Pergamon Press, (1987). Prodrugs include, but are not limited to, compounds derived from compounds of formula I wherein hydroxy, amine or sulfhydryl groups, if present, are bonded to any group that, when administered to the subject, cleaves to form the free hydroxyl, amino or sulfhydryl group, respectively. Selected examples include, but are not limited to, biohydrolyzable amides and biohydrolyzable esters and biohydrolyzable carbamates, carbonates, acetate, formate and benzoate derivatives of alcohol and amine functional groups.

The prodrug can be readily prepared from the compounds of Formula (I) using methods known in the art. See, for example, Notarl, R. E., "Theory and Practice of Prodrug Kinetics," *Methods in Enzymology,* 112:309 323 (1985); Bodor, N., "Novel Approaches in Prodrug Design," *Drugs of the Future,* 6(3):165 182 (1981); and Bundgaard, H., "Design of Prodrugs: Bioreversible-Derivatives for Various Functional Groups and Chemical Entities," in *Design of Prodrugs* (H. Bundgaard, ed.), Elsevier, N.Y. (1985); *Burger's Medicinal Chemistry and Drug Chemistry,* Fifth Ed., Vol. 1, pp. 172-178, 949-982 (1995).

The term "solvate" refers to a complex of variable stoichiometry formed by a solute (in this invention, a compound of formula 1, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid.

The term "stereoisomer" refers to a compound made up of the same atoms bonded by the same bonds but having different three-dimensional structures, which are not interchangeable.

The term "substituted" is intended to indicate that one or more hydrogens on the atom indicated in the expression using "substituted" is replaced with a selection from the indicated group(s), provided that the indicated atom's normal valency is not exceeded, and that the substitution results in a stable compound. Suitable indicated groups include, e.g., alkyl, alkenyl, alkylidenyl, alkenylidenyl, alkoxy, halo, haloalkyl, hydroxy, hydroxyalkyl, aryl, heteroaryl, heterocycle, cycloalkyl, alkanoyl, acyloxy, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyanato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy. When a substituent is oxo (i.e., =O) or thioxo (i.e., =S) group, then two hydrogens on the atom are replaced. The term "sulfonyl" refers to $-SO_2-$.

The term "tautomer" refers to a proton shift from one atom of a molecule to another atom of the same molecule.

The term "therapeutically effective amount" is intended to include an amount of a compound described herein, or an amount of the combination of compounds described herein, e.g., to treat or prevent the disease or disorder, or to treat the symptoms of the disease or disorder, in a host. The combination of compounds is preferably a synergistic combination. Synergy, as described for example by Chou and Talalay, *Adv. Enzyme Regul.,* 22:27 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

The terms "therapy," and "therapeutic" refer to either "treatment" or "prevention," thus, agents that either treat damage or prevent damage are "therapeutic."

The terms "treating" or "treat" or "treatment" refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. As used herein, the term "treatment," covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

In various embodiments, the compound or set of compounds, such as are used in the inventive methods, can be any one of any of the combinations and/or sub-combinations of the above-listed embodiments.

Asymmetric carbon atoms may be present in the compounds described. All such isomers, including diastereomers and enantiomers, as well as the mixtures thereof are intended to be included in the scope of the recited compound. In certain cases, compounds can exist in tautomeric forms. All tautomeric forms are intended to be included in the scope. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated. Thus, reference herein to a compound includes all of the aforementioned isomeric forms unless the context clearly dictates otherwise.

Various forms are included in the embodiments, including polymorphs, solvates, hydrates, conformers, salts, and prodrug derivatives. A polymorph is a composition having the same chemical formula, but a different structure. A solvate is a composition formed by solvation (the combination of solvent molecules with molecules or ions of the solute). A hydrate is a compound formed by an incorporation of water. A conformer is a structure that is a conformational isomer. Conformational isomerism is the phenomenon of molecules with the same structural formula but different conformations (conformers) of atoms about a rotating bond. Salts of compounds can be prepared by methods known to those skilled in the art. For example, salts of compounds can be prepared by reacting the appropriate base or acid with a stoichiometric equivalent of the compound. A prodrug is a compound that undergoes biotransformation (chemical conversion) before exhibiting its pharmacological effects. For example, a prodrug can thus be viewed as a drug containing specialized protective groups used in a transient manner to alter or to eliminate undesirable properties in the parent molecule. Thus, reference herein to a compound includes all of the aforementioned forms unless the context clearly dictates otherwise.

Concentrations, amounts, etc., of various components are often presented in a range format throughout this disclosure. The description in range format is merely for convenience and brevity and should not be construed as an inflexible limitation on the scope of the claimed invention. Accordingly, the description of a range should be considered to have specifically disclosed all the possible subranges as well as individual numerical values within that range. For example, description of a range such as 1% to 8% should be considered to have specifically disclosed subranges such as 1% to 7%, 2% to 8%, 2% to 6%, 3% to 6%, 4% to 8%, 3% to 8% etc., as well as individual numbers within that range, such as, 2%, 5%, 7% etc. This construction applies regardless of the breadth of the range and in all contexts throughout this disclosure.

In the claims provided herein, the steps specified to be taken in a claimed method or process may be carried out in any order without departing from the principles of the invention, except when a temporal or operational sequence is explicitly defined by claim language. Recitation in a claim to the effect that first a step is performed then several other steps are performed shall be taken to mean that the first step is performed before any of the other steps, but the other steps may be performed in any sequence unless a sequence is further specified within the other steps. For example, claim elements that recite "first A, then B, C, and D, and lastly E" shall be construed to mean step A must be first, step E must be last, but steps B, C, and D may be carried out in any sequence between steps A and E and the process of that sequence will still fall within the four corners of the claim.

Furthermore, in the claims provided herein, specified steps may be carried out concurrently unless explicit claim language requires that they be carried out separately or as parts of different processing operations. For example, a claimed step of doing X and a claimed step of doing Y may be conducted simultaneously within a single operation, and the resulting process will be covered by the claim. Thus, a step of doing X, a step of doing Y, and a step of doing Z may be conducted simultaneously within a single process step, or in two separate process steps, or in three separate process steps, and that process will still fall within the four corners of a claim that recites those three steps.

Similarly, except as explicitly required by claim language, a single substance or component may meet more than a single functional requirement, provided that the single substance fulfills the more than one functional requirement as specified by claim language.

The compounds described herein can be prepared by any of the applicable techniques of organic synthesis. Many such techniques are well known in the art. However, many of the known techniques are elaborated in *Compendium of Organic Synthetic Methods* (John Wiley & Sons, New York) Vol. 1, Ian T. Harrison and Shuyen Harrison (1971); Vol. 2, Ian T. Harrison and Shuyen Harrison (1974); Vol. 3, Louis S. Hegedus and Leroy Wade (1977); Vol. 4, Leroy G. Wade Jr., (1980); Vol. 5, Leroy G. Wade Jr. (1984); and Vol. 6, Michael B. Smith; as well as March, J., *Advanced Organic Chemistry*, 3rd Edition, John Wiley & Sons, New York (1985); *Comprehensive Organic Synthesis, Selectivity, Strategy & Efficiency in Modern Organic Chemistry, In 9 Volumes*, Barry M. Trost, Editor-in-Chief, Pergamon Press, New York (1993); *Advanced Organic Chemistry, Part B: Reactions and Synthesis*, 4th Ed.; Carey and Sundberg; Kluwer Academic/Plenum Publishers: New York (2001); *Advanced Organic Chemistry, Reactions, Mechanisms, and Structure*, 2nd Edition, March, McGraw Hill (1977); *Protecting Groups in Organic Synthesis*, 2nd Edition, Greene, T. W., and Wutz, P. G. M., John Wiley & Sons, New York (1991); and *Comprehensive Organic Transformations*, 2nd Edition, Larock, R. C., John Wiley & Sons, New York (1999). Exemplary methods of making the compounds described herein are described herein in the examples below.

Obviously, numerous modifications and variations of the presently disclosed subject matter are possible in light of the above teachings. It is therefore to be understood that within the scope of the claims, the disclosed subject matter may be practiced otherwise than as specifically described herein.

Specific ranges, values, and embodiments provided herein are for illustration purposes only and do not otherwise limit the scope of the disclosed subject matter, as defined by the claims.

It should be understood that the present disclosure encompasses all stereochemical isomeric forms, or mixtures thereof, which possess the ability to kill cancer cells and/or inhibit growth of cancer cells. Enantiomers of the present disclosure may be resolved by methods known to those skilled in the art, for example, by formation of diastereoisomeric salts which may be separated by crystallization, gas-liquid or liquid chromatography, or selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

Certain compounds of the present disclosure may exist in zwitterionic form and the present disclosure includes each zwitterionic form of these compounds and mixtures thereof.

The starting materials useful to synthesize the compounds of the present disclosure are known to those skilled in the art and can be readily manufactured or are commercially available.

The following methods set forth below are provided for illustrative purposes and are not intended to limit the scope of the claimed disclosure. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

The invention relates to synthesis of anticancer compounds of (fluorophenyl)quinolin-4-one derivatives of formula

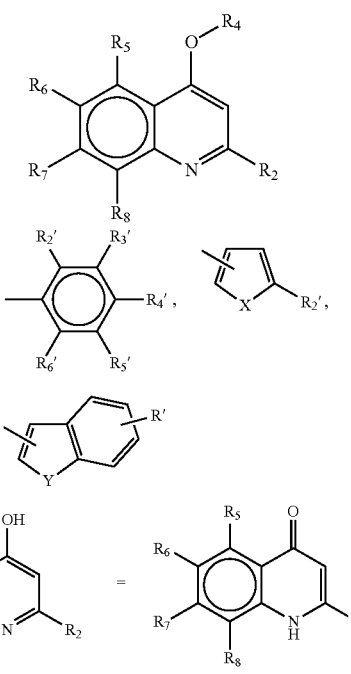

Where R2 =
And R4 = H or G
When R4 = H,

As mentioned above CHM-2133-P exhibited excellent antitumor activity, through both oral and intravenous administration, which is very likely related to its unique structure that was made up of the following three functional groups: Firstly, the phosphate group located on the 4-position of its quinoline ring. As stated in our previous report that pharmacokinetic study of CHM-2133-P confirmed its rapid bio-conversion into its active molecule CHM-2133 following administration. Alkaline phosphatase is known to over-expressed on the extracellular space of specific tumor cells such as ovarian and hepatoma cells, therefore the introduction of a phosphate group appears to be a reasonable strategy for target delivery.

Secondly, the methylenedioxy moiety bridges the 5- and 6-position of its quinoline ring, which could form an ortho-quinone upon metabolism, and could be subsequently metabolized into more cytotoxic metabolites in hypoxia cells. Because severe hypoxia is a common situation of locally advanced solid tumor, the incorporation of methylenedioxy moiety to fight tumors becomes a meaningful approach.

Thirdly, the fluorine atom located on the 2-phenyl group. To certain medicines, the unordinary nature of fluorine was reported to impart a variety of properties including enhanced potency, improved duration of action and attenuation of biliary clearance.

Figure 2:
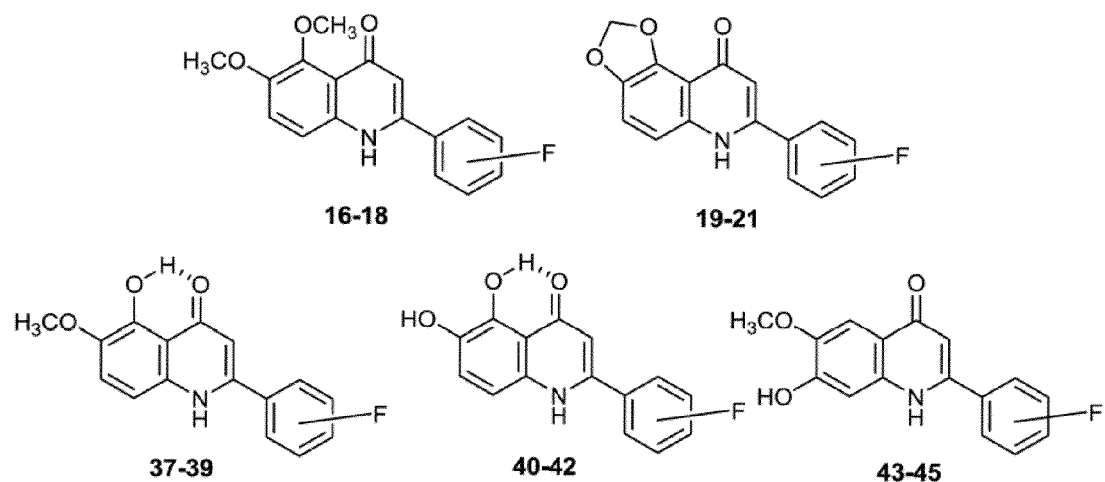
FIG. 2 shows the structures of target compounds 16-21 and 37-45.

Meanwhile, established SAR indicated the existence of a group with lone pair electrons (for instance, $OCH_3$, NRR, Cl, F) at both the 6-position of quinoline ring and 3'-position of 2-phenyl group enhanced the cytotoxicity of 2-PQs. Bearing the structural characteristics of CHM-2133-P in mind, the inventor designed compounds 16-21, 37-45 (FIG. 2) and their phosphates as target compounds based on the following principles: (1) The presence of a O—R group at 6-position of quinoline ring. (2) The presence of a fluorine atom at the 2-phenyl group. (3) Readiness to be metabolized into ortho-quinone in vivo and (4) should be new 2-PQs that were not synthesized before. For illustration, methods of synthesizing target compounds 16-21, 37-45 and evaluating their cytotoxicity are disclosed. Drug candidate compounds may be converted into water soluble, sodium salt of phosphate derivatives for improved hydrophilicity. All the synthesized phosphate derivatives may be evaluated for in vivo anticancer activity.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

General Structures of Compounds

A-Series (Scheme 1~Scheme 5)

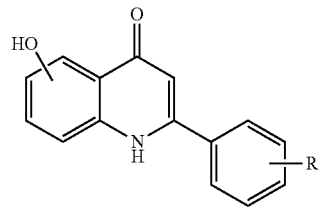

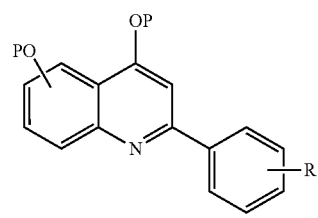

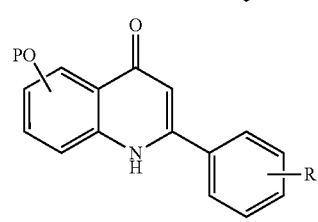

B-Series (Scheme 6~Scheme 10)

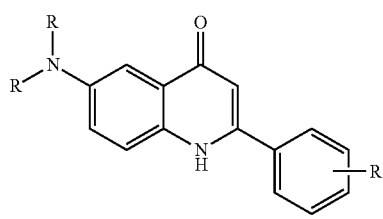

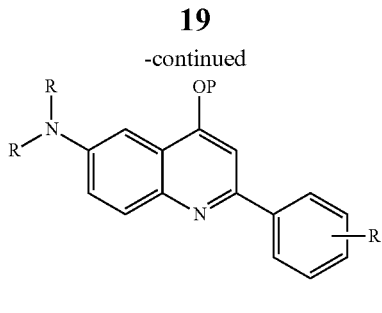

C-Series (Scheme 11 and Scheme 12)

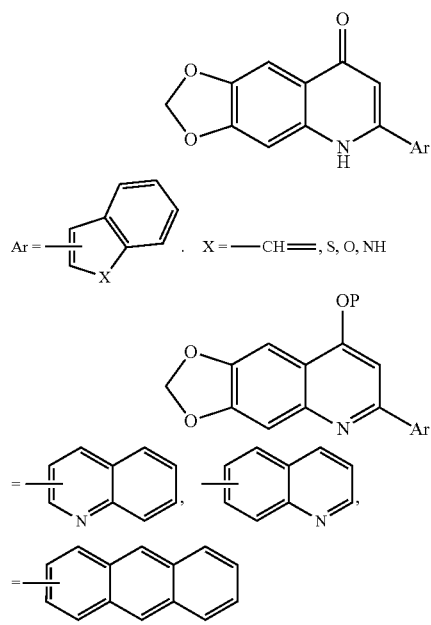

D-Series (Scheme 13)

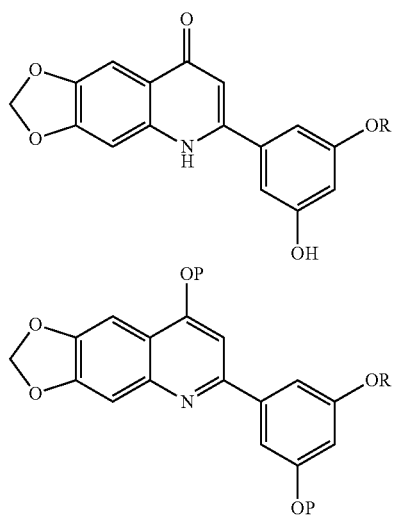

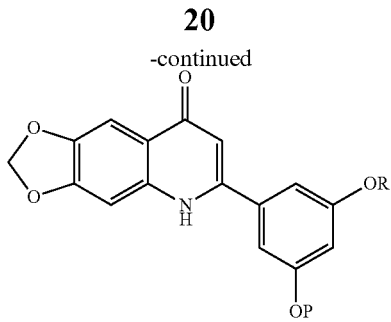

I. A Series

Chemical Synthesis

Scheme 1: Synthesis of Compounds 16-24. The synthesis of 5,6,7,2',3',4'-substituted 2-phenylquinolin-4-ones (16-24) was illustrated in Scheme 1. First, 3,4,5-substituted 1-amino-2-acetylbenzenes (1-3) were reacted separately with 2,3,4-substituted benzoyl chlorides (4-6) to yield the corresponding amides (7-15) that were subsequently cyclized in t-BuOH, in the presence of i-BuOK, to afford the desired compounds (16-24).

Scheme 2: Synthesis of Starting Compounds 1-3. The starting compounds 1-3 were not from commercial source, and were prepared according to Scheme 2. Following a published method,[8] 2,3-dimethoxybenzonitrile (25) was subjected to Grignard reaction by reacting with $CH_3MgBr$ in ether to yield 2,3-dimethoxyacetophenone (26). Compound 26 was then nitrated with 70% $HNO_3$ to give 2,3-dimethoxy-6-nitroacetophenone (27) which, without purification, was hydrogenated over Pd/C. The reaction product was purified by column chromatography to afford 6-amino-2,3-dimethoxyacetophenone (1) whose structure was confirmed by 2D-NMR spectra.

6-Amino-2,3-dimethoxyacetophenone (2) was also prepared according to published methods. The starting catechol (28) was acetylated, in microwave oven set at 300 Watt power, by reacting with mixture of acetic acid (29) and $BF_3 \cdot Et_2O$ to yield 2,3-dihydroxyacetophenone (30) which was further reacted with diiodomethane in DMF, in the presence of $K_2CO_3$, to afford 2,3-methylenedioxyacetophenone (31). Subsequent nitration of compound 31 with 70% $HNO_3$ afforded 2,3-methylenedioxy-6-nitroacetophenone (32). Without purification, compounds 32 was hydrogenated, and purified with column chromatography to provide 6-amino-2,3-methylenedioxyacetophenone (2).[10] Another published method was followed in preparation of 6-amino-3-methoxy-4-benzyloxyacetophenone (3). First, the benzylation of the starting acetovanillone (33) with benzylbromide (34) gave 4-benzyloxy-3-methoxyacetophenone (35) which was nitrated to yield 4-benzyloxy-3-methoxy-6-nitroacetophenone (36).[11] The so-obtained compound 36 was reduced with $SnCl_2$ to afford compound 3.

Scheme 3: Synthesis of Compounds 37-45. Scheme 3 illustrated the preparation of designed compounds 37-45. As shown, compounds 16-18 were selectively demethylated by treating with $BCl_3$ in $CH_2Cl_2$, to afford the corresponding 2-(fluorophenyl)-5-hydroxy-6-methoxyquinolin-4-ones (37-39) whose structures were confirmed by 2D-NMR spectra. Catalytic hydrogenation of compounds 19-21 yielded 2-(fluorophenyl)-5,6-dihydroxyquinolin-4-ones (40-42), and similarly, hydrogenation of 7-benzyloxy-2-(fluorophenyl)-6-methoxyquinolin-4-ones (22-24) gave 2-(fluorophenyl)-7-hydroxy-6-methoxyquinolin-4-ones (43-45).

Scheme 1

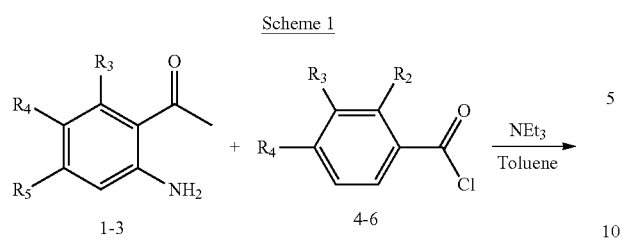

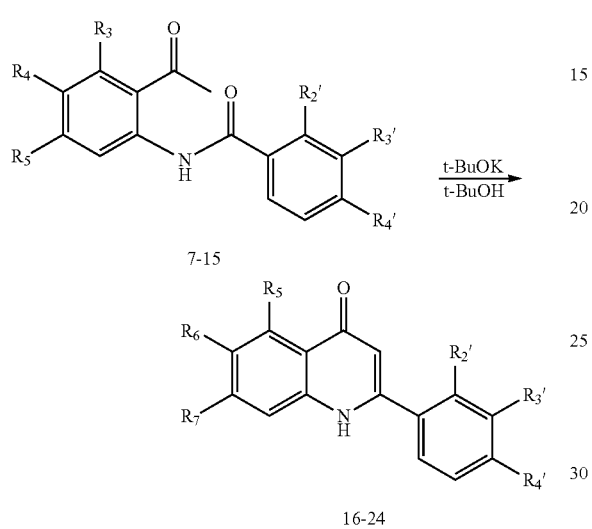

1, $R_3 = R_4 = OCH_3$, $R_5 = H$
2, $R_3, R_4 = $ —$OCH_2O$—, $R_5 = H$
3, $R_3 = H$, $R_4 = OCH_3$, $R_5 = OCH_2Ph$
4, $R_2 = F$, $R_3 = H$, $R_4 = H$
5, $R_2 = H$, $R_3 = F$, $R_4 = H$
6, $R_2 = H$, $R_3 = H$, $R_4 = F$
7, $R_3 = R_4 = OCH_3$, $R_5 = H$, $R_2' = F$, $R_3' = H$, $R_4' = H$
8, $R_3 = R_4 = OCH_3$, $R_5 = H$, $R_2' = H$, $R_3' = F$, $R_4' = H$
9, $R_3 = R_4 = OCH_3$, $R_5 = H$, $R_2' = H$, $R_3' = H$, $R_4' = F$
10, $R_3, R_4 = $ —$OCH_2O$—, $R_5 = H$, $R_2' = F$, $R_3' = H$, $R_4' = H$
11, $R_3, R_4 = $ —$OCH_2O$—, $R_5 = H$, $R_2' = H$, $R_3' = F$, $R_4' = H$
12, $R_3, R_4 = $ —$OCH_2O$—, $R_5 = H$, $R_2' = H$, $R_3' = H$, $R_4' = F$
13, $R_3 = H$, $R_4 = OCH_3$, $R_5 = OCH_2Ph$, $R_2' = F$, $R_3' = H$, $R_4' = H$
14, $R_3 = H$, $R_4 = OCH_3$, $R_5 = OCH_2Ph$, $R_2' = H$, $R_3' = F$, $R_4' = H$
15, $R_3 = H$, $R_4 = OCH_3$, $R_5 = OCH_2Ph$, $R_2' = H$, $R_3' = H$, $R_4' = F$
16, $R_5 = R_6 = OCH_3$, $R_7 = H$, $R_2' = F$, $R_3' = H$, $R_4' = H$
17, $R_5 = R_6 = OCH_3$, $R_7 = H$, $R_2' = H$, $R_3' = F$, $R_4' = H$
18, $R_5 = R_6 = OCH_3$, $R_7 = H$, $R_2' = H$, $R_3' = H$, $R_4' = F$
19, $R_5, R_6 = $ —$OCH_2O$—, $R_7 = H$, $R_2' = F$, $R_3' = H$, $R_4' = H$
20, $R_5, R_6 = $ —$OCH_2O$—, $R_7 = H$, $R_2' = H$, $R_3' = F$, $R_4' = H$
21, $R_5, R_6 = $ —$OCH_2O$—, $R_7 = H$, $R_2' = H$, $R_3' = H$, $R_4' = F$
22, $R_5 = H$, $R_6 = OCH_3$, $R_7 = OCH_2Ph$, $R_2' = F$, $R_3' = H$, $R_4' = H$
23, $R_5 = H$, $R_6 = OCH_3$, $R_7 = OCH_2Ph$, $R_2' = H$, $R_3' = F$, $R_4' = H$
24, $R_5 = H$, $R_6 = OCH_3$, $R_7 = OCH_2Ph$, $R_2' = H$, $R_3' = H$, $R_4' = F$

Scheme 2

A

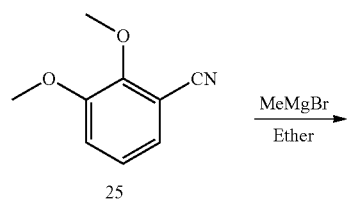

B

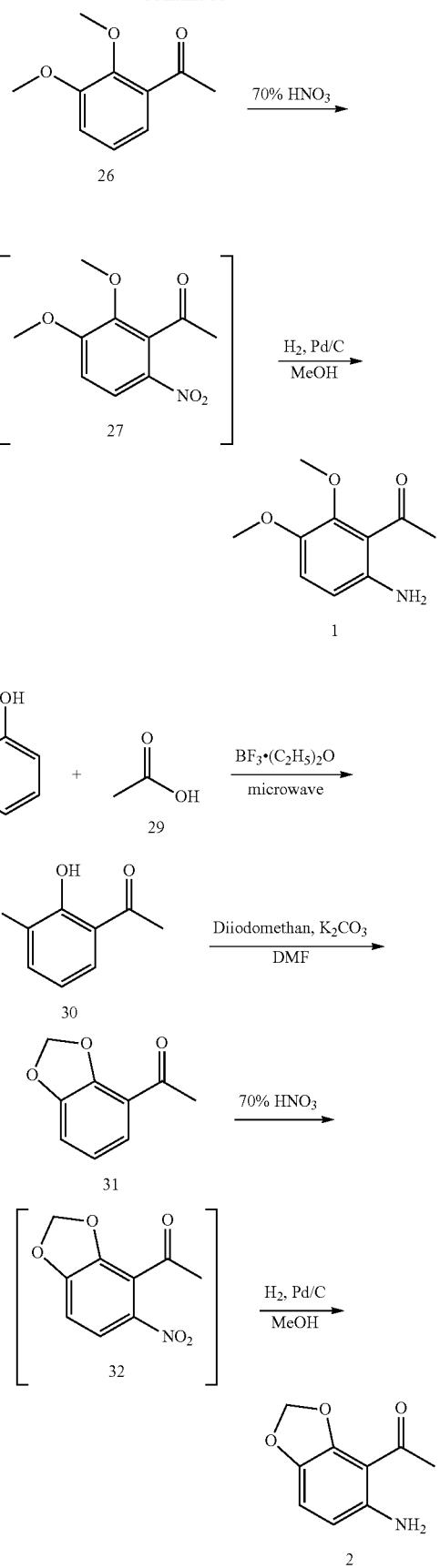

-continued

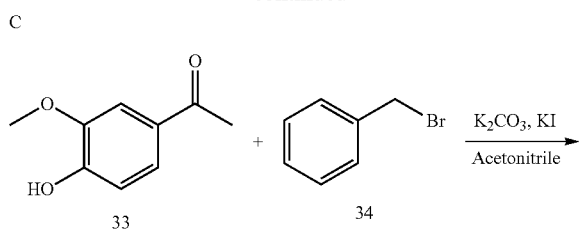

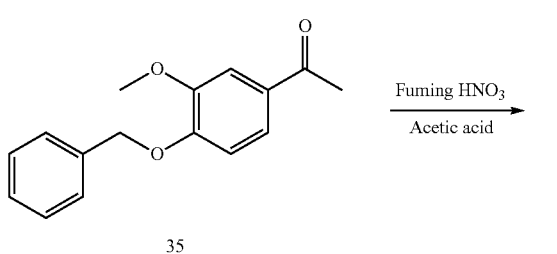

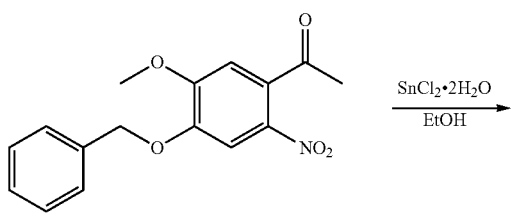

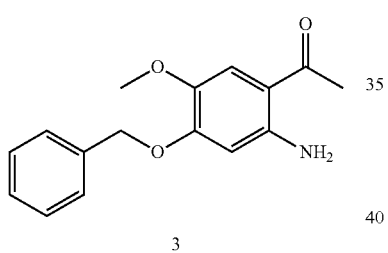

Scheme 3

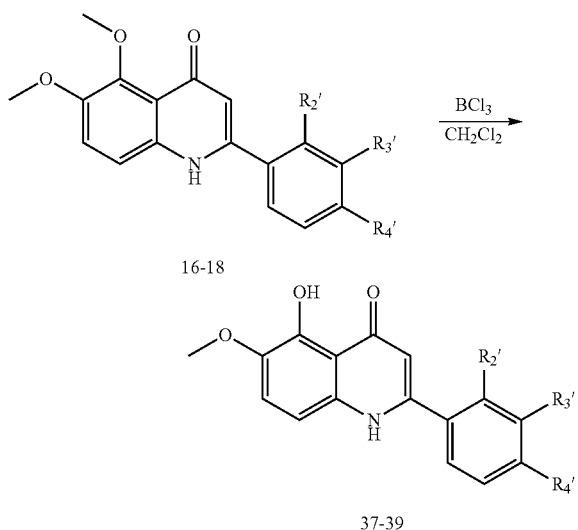

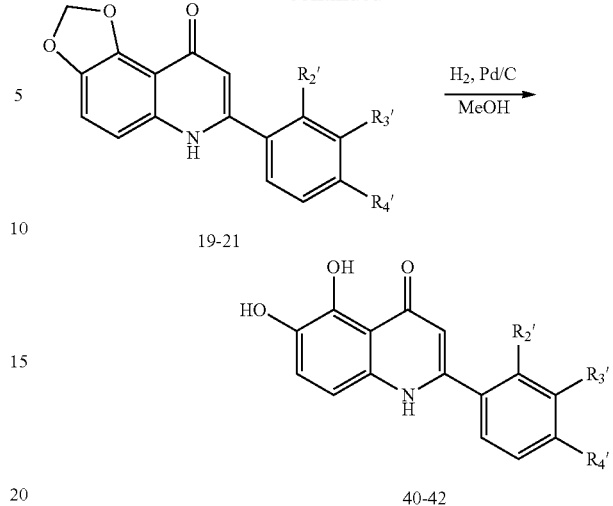

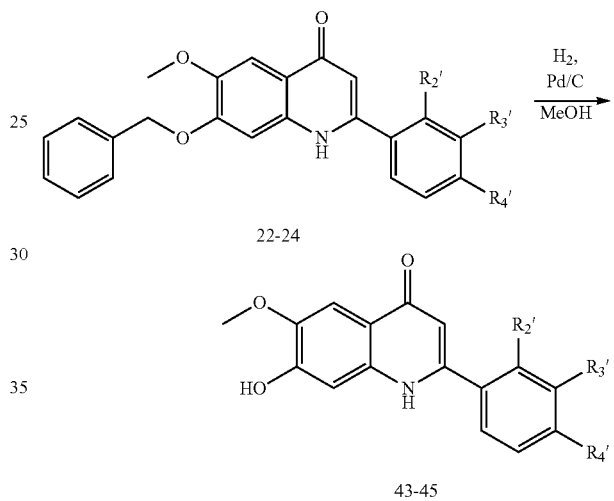

37, 40, 43, $R_2' = F, R_3' = H, R_4' = H$
38, 41, 44, $R_2' = H, R_3' = F, R_4' = H$
39, 42, 45, $R_2' = H, R_3' = H, R_4' = F$

Schemes 4-5: Phosphorylation of Compound 38. The phosphorylation of 2-(3-fluorophenyl)-5-hydroxy-6-methoxyquinoline-4-one (38) was illustrated in Schemes 4 and 5. Compound 38 was first reacted with tetrabenzylpyrophosphate (46) in THF in the presence of NaH or dibenzylphosphite (47) to yield 2-(3-fluorophenyl)-6-methoxyquinoline-4,5-diyl bis(dibenzyl phosphate) (48). Compound 48 was then subjected to catalytic hydrogenation in MeOH to give its diphosphoric acid (49). Finally, compound 49 was converted into water soluble sodium salt (50) by treatment with NaHCO₃. In the process of purifying compound 48, the coexistence of its dephosphorylated derivative was found. Presumably as illustrated in Scheme 5, the inductive effect by the nitrogen atom on the 1-position of quinoline ring facilitated the selective elimination of phosphate moiety on the 4-position of the same ring. Upon testing several conditions of reaction led to selective 4-phosphate elimination of compound 48, it was found that stirring at room temperature of compound 48 dissolved in MeOH resulted in precipitation of its monophosphate derivative 51 whose structure was confirmed by the ¹H-NMR chemical shift of its proton on the 3-position (δ 6.27). Finally, using the same synthetic procedure for compound 50, the hydrogenation of compound 51, followed by treatment with NaHCO₃, resulted in desired water soluble, sodium salt of monophosphate derivative (52).

Scheme 4
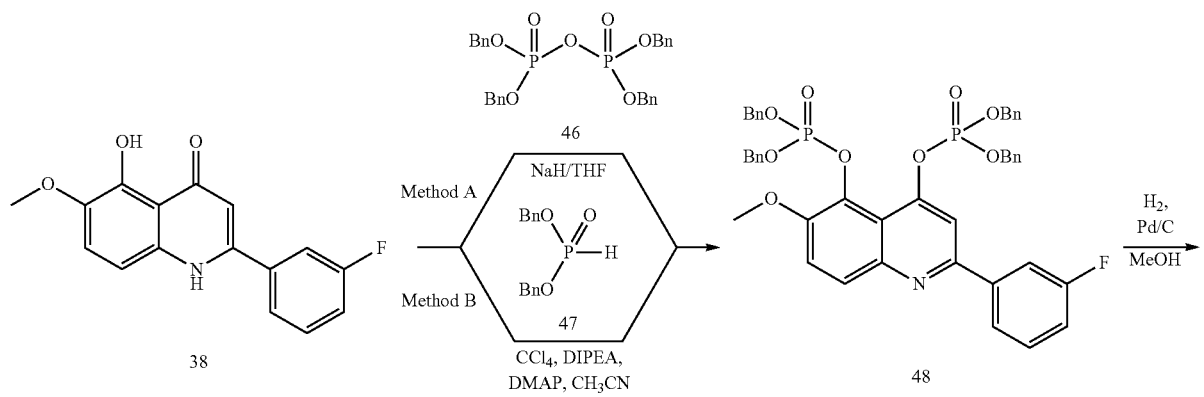
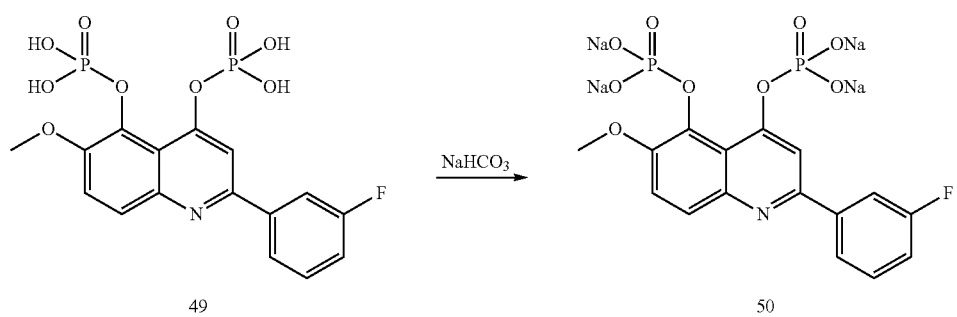
Scheme 5
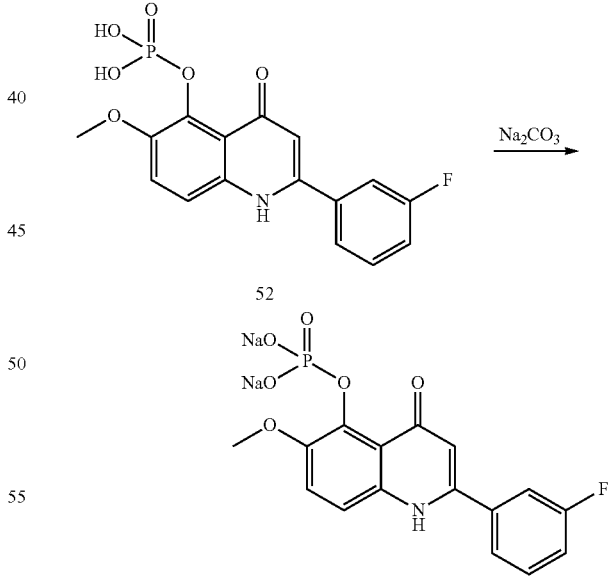
EXAMPLES
General Experimental Procedures. All of the reagents and solvents were obtained commercially and used without further purification. Reactions were monitored by thin-layer chromatography, using Merck plates with fluorescent indicator (TLC Silica gel 60 $F_{254}$). The following adsorbent was used for column chromatography: silica gel 60 (Merck, particle size 0.063-0.200 mm). Melting points were determined on a Yanaco MP-500D melting point apparatus and were uncorrected. IR spectra were recorded on Shimadzu IRPrestige-21 spectrophotometers as KBr pellets. NMR spectra were obtained on a Bruker Avance DPX-200 FT-NMR spectrometer in $CDCl_3$ or DMSO. The following abbreviations are used: s, singlet; d, doublet; t, triplet; q, quartet; dd, double doublet and m, multiplet. EI-MS spectra were measured with an HP 5995 GC-MS instrument. ESI-MS spectra were measured with a Finnigan LCQ ion-trap mass spectrometer (TSQ Quantum, Thermo Finnigan Corporation, San Jose, Calif.). Elemental analyses (C, H, and N) were performed on a Perkin-Elmer 2400 Series II CHNS/O analyzer, and the results were within ±0.4% of the calculated values.

N-(2-Acetyl-3,4-dimethoxyphenyl)-2-fluorobenzamide (7). To a solution of 2-fluorobenzoyl chloride (4), 0.48 g, 2.46 mmol) in 40 mL of dry toluene were added triethylamine (0.5 mL) and compound 1 (0.70 g, 4.43 mmol). The mixture was stirred at 55-60° C. for 30 min, and then poured into crushed ice, extracted with EtOAc. The organic layer was washed with brine, dried over $MgSO_4$ and evaporated. The crude product was purified by column chromatography (Silica gel, EtOAc/n-hexane) to give 7 (0.5 g, 1.58 mmol) as a yellow solid. Yield: 64.1%; mp 106-108° C.; MS (EI, 70 eV): m/z 317 ($M^+$); $^1$H-NMR (DMSO-$d_6$, 200 MHz): δ 2.45 (s, 3H), 3.76 (s, 3H), 3.81 (s, 3H), 7.14 (d, J=2.6 Hz, 2H), 7.24-7.34 (m, 2H), 7.52-7.63 (n7, 2H), 10.07 (s, 1H); $^{13}$C-NMR (DMSO-$d_6$, 50 MHz): δ 31.91, 56.52, 61.42, 114.52, 116.70, 121.43, 124.16, 125.06, 126.81, 130.52, 131.50, 133.35 (d, =8.0 Hz), 145.98, 150.47, 159.61 (d, J=247.5 Hz), 163.19, 201.38; Anal. calcd for $C_{17}H_{16}FNO_4$: C, 64.35; H, 5.08; N, 4.41. Found: C, 64.31; H, 5.10; N, 4.43.

N-(2-Acetyl-3,4-dimethoxyphenyl)-3-fluorobenzamide (8) was obtained from 1 and 3-fluorobenzoyl chloride (5). Yellow solid; Yield: 65.0%; nip 98-99° C.; MS (EI, 70 eV): m/z 317 ($M^+$); $^1$H-NMR (DMSO-$d_6$, 200 MHz): δ 2.43 (s, 3H), 3.76 (s, 3H), 3.81 (s, 3H), 7.03-7.15 (m, 2H), 7.39-7.71 (m, 4H), 10.18 (s, 1H); $^{13}$C-NMR (DMSO-$d_6$, 50 MHz): δ 31.74, 56.45, 61.38, 114.30, 114.73 (d, J=23 Hz), 119.04 (d, J=21 Hz), 121.98, 124.13, 126.91, 131.12 (d, J=7.5 Hz), 132.27, 136.89 (d, J=6.5 Hz), 145.90, 150.65, 162.40 (d, J=243 Hz), 164.67, 201.22; Anal. calcd for $C_{17}H_{16}FNO_4$: C, 64.35; H, 5.08; N, 4.41. Found: C, 64.34; H, 5.06; N, 4.44.

N-(2-Acetyl-3,4-dimethoxyphenyl)-4-fluorobenzamide (9) was obtained from 1 and 4-fluorobenzoyl chloride (6). Yellow solid; Yield: 64.7%; mp 146-147° C.; MS (EI, 70 eV): m/z 317 ($M^+$); $^1$H-NMR (DMSO-$d_6$, 200 MHz): δ 2.43 (s, 3H), 3.76 (s, 3H), 3.81 (s, 3H), 7.03-7.14 (m, 2H), 7.26-7.35 (m, 2H), 7.88-7.95 (m, 2H), 10.14 (s, 1H); $^{13}$C-NMR (DMSO-$d_6$, 50 MHz): δ 31.76, 56.48, 61.38, 114.33, 115.83 (d, J=22 Hz), 121.91, 127.17, 130.65 (d, J=9.0 Hz), 131.06, 132.21, 145.90, 150.53, 164.57 (d, J=247 Hz), 164.94, 201.25; Anal. calcd for $C_{17}H_{16}FNO_4$: C, 64.35; H, 5.08; N, 4.41. Found: C, 64.36; H, 5.11; N, 4.40.

N-(2-Acetyl-3,4-methylenedioxyphenyl)-2-fluorobenzamide (10) was obtained from 2 and 4. Yellow solid; Yield: 90.0%; mp 165-166° C.; MS (EI, 70 eV): m/z 301 ($M^+$); $^1$H-NMR (DMSO-$d_6$, 200 MHz): δ 2.53 (s, 3H), 6.13 (s, 2H), 7.12 (d, J=8.6 Hz, 1H), 7.28-7.38 (m, 2H), 7.56-7.61 (m, 1H), 7.72-7.82 (m, 1H), 7.85 (d, J=8.8 Hz, 1H), 11.50 (s, 1H); $^{13}$C-NMR (DMSO-$d_6$, 50 MHz): δ 32.53, 102.57, 111.92, 112.52, 114.74, 116.94 (d, J=22.5 Hz), 123.55 (d, J=12.5 Hz), 125.41, 130.98; 131.91, 134.04 (d, J=8.5 Hz), 144.46, 149.00, 157.18, 162.22, 199.61; Anal. calcd for $C_{16}H_{12}FNO_4$: C, 63.79; H, 4.01; N, 4.65. Found: C, 63.75; H, 4.03; N, 4.67.

N-(2-Acetyl-3,4-methylenedioxyphenyl)-3-fluorobenzamide (11) was obtained from 2 and 5. Yellow solid; Yield: 95.0%; mp 170-171° C.; MS (EI, 70 eV): m/z 301 ($M^+$); $^1$H-NMR (DMSO-$d_6$, 200 MHz): δ 2.56 (s, 3H), 6.14 (s, 2H), 7.13 (d, J=8.4 Hz, 1H), 7.43 (t, J=8.6 Hz, 1H), 7.52-7.68 (m, 2H), 7.72 (d, J=8.6 Hz, 2H), 11.56 (s, 1H); $^{13}$C-NMR (DMSO-$d_6$, 50 MHz): δ 32.48, 102.61, 112.48, 112.62, 114.48 (d, J=23 Hz), 114.89, 119.30 (d, J=21.5 Hz), 123.56, 131.52 (d, J=8.0 Hz), 131.96, 137.32, 144.61, 148.88, 162.61 (d, J=243.5 Hz), 163.97, 199.88; Anal. calcd for $C_{16}H_{12}FNO_4$: C, 63.79; H, 4.01; N, 4.65. Found: C, 63.67; H, 4.00; N, 4.63.

N-(2-Acetyl-3,4-methylenedioxyphenyl)-4-fluorobenzamide (12) was obtained from 2 and 6. Yellow solid; Yield: 84.0%; mp 185-186° C.; MS (EI, 70 eV): m/z 301 ($M^+$); $^1$H-NMR (DMSO-$d_6$, 200 MHz): δ 2.51 (s, 3H), 6.13 (s, 2H), 7.12 (d, J=8.6 Hz, 1H), 7.20-7.40 (m, 2H), 7.77 (d, J=8.6 Hz, 1H), 7.89-7.97 (m, 2H), 11.58 (s, 11-1); $^{13}$C-NMR (DMSO-$d_6$, 50 MHz): δ 32.55, 102.55, 111.20, 112.61, 114.54, 116.26 (d, J=22 Hz), 130.22 (d, J=7.0 Hz), 131.47, 132.41, 144.36, 148.97, 162.22, 164.67 (d, J=248 Hz), 200.04; Anal. calcd for $C_{16}H_{12}FNO_4$: C, 63.79; H, 4.01; N, 4.65. Found: C, 63.84; H, 3.98; N, 4.65.

N-(2-Acetyl-5-benzyloxy-4-methoxyphenyl)-2-fluorobenzamide (13) was obtained from 3 and 4. Yellow solid; Yield: 89.0%; mp 142-143° C.; MS (EI, 70 eV): m/z 393 ($M^+$); $^1$H-NMR (DMSO-$d_6$, 200 MHz): δ 2.60 (s, 3H), 3.82 (s, 3H), 5.16 (s, 2H), 7.10-7.50 (m, 8H), 7.56-7.67 (m, 1H), 7.80-7.89 (m, 1H), 8.57 (s, 1H), 12.45 (d, J=4.0 Hz, 1H); $^{13}$C-NMR (DMSO-$d_6$, 50 MHz): δ 29.08, 56.42, 70.41, 105.31, 115.28, 116.05, 117.08 (d, J=22 Hz), 123.27 (d, J=12.5 Hz), 125.60, 128.58, 128.95, 131.20, 134.45 (d, J=8.5 Hz), 135.77, 136.50, 144.46, 152.98, 157.26, 162.35, 201.78; Anal. calcd for $C_{23}H_{20}FNO_4$: C, 70.22; H, 5.12; N, 3.56. Found: C, 70.18; H, 5.10; N, 3.55.

N-(2-Acetyl-5-benzyloxy-4-methoxyphenyl)-3-fluorobenzamide (14) was obtained from 3 and 5. Yellow solid; Yield: 86.6%; mp 162-163° C.; MS (EI, 70 eV): m/z 393 ($M^+$); $^1$H-NMR (DMSO-$d_6$, 200 MHz): δ 2.62 (s, 3H), 3.81 (s, 3H), 5.15 (s, 2H), 7.26-7.52 (m, 7H), 7.54-7.78 (m, 3H), 8.51 (s, 1H), 12.70 (s, 1H); $^{13}$C-NMR (DMSO-$d_6$, 50 MHz): δ 29.10, 56.42, 70.40, 104.74, 114.45, 115.29, 115.83, 119.59 (d, J=21.5 Hz), 123.36, 128.53, 128.95, 131.74 (d, J=7.5 Hz), 136.28, 136.45, 137.30 (d, J=6.5 Hz), 144.43, 153.26, 162.71 (d, J=244 Hz), 163.91, 202.48; Anal. calcd for $C_{23}H_{20}FNO_4$: C, 70.22; H, 5.12; N, 3.56. Found: C, 70.20; H, 5.14; N, 3.52.

N-(2-Acetyl-5-benzyloxy-4-methoxyphenyl)-4-fluorobenzamide (15) was obtained from 3 and 6. Yellow solid; yield: 67.1%; mp 168-169° C.; MS (EI, 70 eV): m/z 393 ($M^+$); $^1$H-NMR (DMSO-$d_6$, 200 MHz): δ 2.63 (s, 3H), 3.81 (s, 3H), 5.15 (s, 2H), 7.2-7.5 (m, 7H), 7.9-8.1 (m, 3H), 8.54 (s, 1H), 12.69 (s, 1H); $^{13}$C-NMR (DMSO-$d_6$, 50 MHz): δ 29.11, 56.47, 70.41, 104.73, 115.39, 115.83, 116.27, 116.72, 128.53, 128.94, 130.17 (d, J=9.0 Hz), 132.54 (d, J=9.5 Hz), 136.48, 136.58, 144.33, 153.33, 164.24, 166.82, 202.48; Anal. calcd for $C_{23}H_{20}FNO_4$: C, 70.22; H, 5.12; N, 3.56. Found: C, 70.24; H, 5.12; N, 3.59.

2-(2-Fluorophenyl)-5,6-dimethoxyquinolin-4-one (16). To a suspension of 7 (0.50 g, 1.58 mmol) in t-butyl alcohol (30 mL) was added potassium t-butoxide (1.0 g, 8.93 mmol). The mixture was refluxed under argon for 20 h and evaporated. The residue was treated with a 10% ammonium chloride solution (30 mL). The solid precipitate was collected and washed with n-hexane and $Me_2CO$. The crude product was recrystallized from MeOH afforded yellow needle of 16 (0.27 g, 0.9 mmol). Yield: 57.1%; mp 215-217° C.; MS (EI, 70 eV): m/z 299 (M$^+$); IR (KBr): 1628 (C=O) cm$^{-1}$; $^1$H-NMR (DMSO-d$_6$. 200 MHz): δ 3.72 (s, 3.81 (s, 3H), 6.06 (s, 1H), 7.3-7.6 (m, 5H), 7.60-7.71 (m, 1H); Anal. calcd for C$_{17}$H$_{14}$FNO$_3$: C, 68.22; H, 4.71; N, 4.68. Found: C, 68.24; H, 4.67; N, 4.71.

2-(3-Fluorophenyl)-5,6-dimethoxyquinolin-4-one (17) was obtained from 8. Yellow needle; yield: 53.1%; mp 190-192° C.; MS (EI, 70 eV): m/z 299 (M$^+$); IR (KBr): 1599 (C=O) cm$^{-1}$; $^1$H-NMR (DMSO-d$_6$. 200 MHz): δ 3.73 (s, 3H), 3.81 (s, 3H), 6.35 (s, 1H), 7.28-7.40 (m, 1H), 7.46-7.60 (m, 3H), 7.64-7.76 (m, 2H); Anal. calcd for C$_{17}$H$_{14}$FNO$_3$: C, 68.22; H, 4.71; N, 4.68. Found: C, 68.17; H, 4.68; N, 4.66.

2-(4-Fluorophenyl)-5,6-dimethoxyquinolin-4-one (18) was obtained from 9. White needle; yield: 54.6%; mp 227-229° C.; MS (EI, 70 eV): m/z 299 (M$^+$); IR (KBr): 1607 (C=O) cm$^{-1}$; $^1$H-NMR (DMSO-d$_6$, 200 MHz): δ 3.72 (s, 3H), 3.80 (s, 3H), 6.26 (s, 1H), 7.31-7.40 (m, 2H), 7.44-7.54 (m, 2H), 7.83-7.90 (m, 2H); Anal. calcd for C$_{17}$H$_{14}$FNO$_3$: C, 68.22; H, 4.71; N, 4.68. Found: C, 68.16; H, 4.68; N, 4.65.

2-(2-Fluorophenyl)-5,6-methylenedioxyquinolin-4-one (19) was obtained from 10. Yellow solid; yield: 47.6%; mp 282-283° C.; MS (EI, 70 eV): m/z 283 (M$^+$); IR (KBr): 1605 (C=O) cm$^{-1}$; $^1$H-NMR (DMSO-d$_6$, 200 MHz): δ 5.92 (s, 1H), 6.11 (s, 2H), 7.09 (d, J=8.8 Hz, 1H), 7.27-7.38 (m, 3H), 7.55-7.70 (m, 2H), 11.71 (s, 1H); Anal. calcd for C$_{16}$H$_{10}$FNO$_3$: C, 67.84; H, 3.56; N, 4.94. Found: C, 67.82; H, 3.53; N, 4.91.

2-(3-Fluorophenyl)-5,6-methylenedioxyquinolin-4-one (20) was obtained from 11. White solid; yield: 44.9%; mp 286-288° C.; MS (EI, 70 eV): m/z 283 (M$^+$); IR (KBr): 1609 (C=O) cm$^{-1}$; $^1$H-NMR (DMSO-d$_6$, 200 MHz): δ 6.11 (s, 2H), 6.19 (s, 1H), 7.19-7.36 (m, 3H), 7.55-7.67 (m, 3H), 11.71 (s, 1H); Anal. calcd for C$_{16}$H$_{10}$FNO$_3$: C, 67.84; H, 3.56; N, 4.94. Found: C, 67.90; H, 3.52; N, 4.95.

2-(4-Fluorophenyl)-5,6-methylenedioxyquinolin-4-one (21) was obtained from 12. White solid; yield: 45.9%; mp 286-288° C.; MS (EI, 70 eV): m/z 283 (M$^+$); IR (KBr): 1613 (C=O) cm$^{-1}$; $^1$H-NMR (DMSO-d$_6$, 200 MHz): δ 6.10 (s, 3H), 7.17-7.31 (m, 2H), 7.32-7.41 (m, 2H), 7.78-7.85 (m, 2H), 11.46 (s, 1H); Anal. calcd for C$_{16}$H$_{10}$FNO$_3$: C, 67.84; H, 3.56; N, 4.94. Found: C, 67.88; H, 3.51; N, 4.97.

7-Benzyloxy-2-(2-fluorophenyl)-6-methoxyquinolin-4-one (22) was obtained from 13. White solid; yield: 60.5%; mp 132-134° C.; MS (EI, 70 eV): m/z 375 (M$^+$); $^1$H-NMR (DMSO-d$_6$, 200 MHz): δ 3.82 (s, 3H), 5.16 (s, 2H), 6.21 (s, 1H), 7.20-7.80 (m, 11H); $^{13}$C-NMR (DMSO-d$_6$, 50 MHz): δ 56.02, 70.40, 101.86, 104.14, 108.80, 116.77 (d, J=21.5 Hz), 118.86, 123.30 (d, J=13 Hz), 125.43, 128.50, 128.97, 131.24, 132.56 (d, J=8.0 Hz), 136.58, 137.08, 144.73, 147.73, 152.52, 159.64 (d, J=247 Hz), 174.57; Anal. calcd for C$_{23}$H$_{18}$FNO$_3$: C, 73.59; H, 4.83; N, 3.73. Found: C, 73.55; H, 4.81; N, 3.71.

7-Benzyloxy-2-(3-fluorophenyl)-6-methoxyquinolin-4-one (23) was obtained from 14. White solid; yield: 64.3%; mp 154-155° C.; MS (EI, 70 eV): m/z 375 (M$^+$); $^1$H-NMR (DMSO-d$_6$, 200 MHz): δ 3.83 (s, 3H), 5.17 (s, 2H), 6.56 (s, 1H), 7.30-7.50 (m, 8H), 7.55-7.60 (m, 1H), 7.60-7.80 (m, 2H); $^{13}$C-NMR (DMSO-d$_6$, 50 MHz): δ 56.07, 70.45, 102.27, 103.72, 106.03, 114.71 (d, J=23.5 Hz), 117.56 (d, J=20.5 Hz), 118.44, 123.95, 128.56, 128.99, 131.50, 136.49, 137.41, 148.02, 148.44, 152.72, 165.13, 173.61; Anal. calcd for C$_{23}$H$_{18}$FNO$_3$: C, 73.59; H, 4.83; N, 3.73. Found: C, 73.61; H, 4.80; N, 3.72.

7-Benzyloxy-2-(4-fluorophenyl)-6-methoxyquinolin-4-one (24) was obtained from 15. White solid; yield: 64.4%; mp 248-249° C.; MS (EI, 70 eV): m/z 375 (M$^+$); $^1$H-NMR (DMSO-d$_6$. 200 MHz): δ 3.80 (s, 3H), 5.13 (s, 2H), 6.26 (s, 1H), 7.20-7.60 (m, 9H), 7.80-8.00 (m, 2H); $^{13}$C-NMR (DMSO-d$_6$, 50 MHz): δ 55.96, 70.36, 101.41, 104.51, 106.61, 116.30 (d, J=21.5 Hz), 119.27, 128.56, 128.99, 130.05 (d, J=8.0 Hz), 136.60, 147.39, 148.06, 152.19, 163.63 (d, J=246.5 Hz), 176.10; Anal. calcd for C$_{23}$H$_{18}$FNO$_3$: C, 73.59; H, 4.83; N, 3.73. Found: C, 73.56; H, 4.83; N, 3.75.

2,3-Dimethoxyacetophenone (26). To a stirred solution of 2,3-dimethoxybenzonitrile (25) (5.0 g, 30 mmol) in Et$_2$O (12.5 mL) under N$_2$ atmosphere was added methylmagnesium bromide (37% in Et$_2$O) (12.5 mL, 37 mmol). The mixture was stirred for 16 h, and then 50% AcOH (20 mL) was added. After it was stirred for 30 min, the solution was poured into crushed ice, extracted with CH$_2$Cl$_2$, washed with 10% Na$_2$CO$_3$ and then with water, dried over MgSO$_4$ and concentrated. The crude was purified by column chromatography (SiO$_2$, n-hexane: EtOAc=4:1) to give 26. Liquid; yield: 92.5%; $^1$H-NMR (CDCl$_3$, 200 MHz): δ 2.56 (s, 3H), 3.82 (s, 3H), 3.85 (s, 3H), 6.99-7.02 (m, 2H), 7.13-7.18 (m, 1H); $^{13}$C-NMR (CDCl$_3$, 50 MHz): δ 31.18, 55.98, 61.29, 115.83, 120.80, 123.94, 133.62, 148.63, 153.04, 200.26; Anal. calcd for C$_{10}$H$_{12}$O$_3$: C, 66.65; H, 6.71. Found: C, 66.60; H, 6.73.

6-Amino-2,3-dimethoxyacetophenone (1). Compound 26 (5.0 g, 27.8 mmol) was stirred at −5±1° C. and 70% HNO$_3$ (60 mL) was added dropwise. After it was stirred at −5±1° C. for 10 min, the reaction mixture was poured into crushed ice, extracted with CH$_2$Cl$_2$. The extract was washed with 10% Na$_2$CO$_3$ and then with water, dried over MgSO$_4$ and concentrated. The crud intermediate (27) was directly in the next step.

A solution of 27 (1.85 g, 8.22 mmol) in anhydrous MeOH (40 mL) was hydrogenated in the presence of 10% Pd/C (0.5 g) at 25±2° C. for 2 h. The Pd/C was filtered off and the filtrate was evaporated. The residue was purified by column chromatography (SiO$_2$, n-hexane: EtOAc=25:1) to give 1. Liquid; yield: 43.7%; $^1$H-NMR (DMSO-d$_6$, 200 MHz): δ 2.41 (s, 3H), 3.66 (s, 3H), 3.74 (s, 3H), 5.88 (s, 2H), 6.41 (d, J=9.0 Hz, 1H), 6.98 (d, J=9.0 Hz, 1H); $^{13}$C-NMR (DMSO-d$_6$, 50 MHz): δ 33.09, 57.58, 61.14, 111.82, 116.82, 121.15, 142.62, 144.22, 149.87, 201.88; Anal. calcd for C$_{10}$H$_{13}$NO$_3$: C, 61.53; H, 6.71; N, 7.18. Found: C, 61.51; H, 6.74; N, 7.22.

2,3-Dihydroxyacetophenone (30). To a solution of 1,2-dihydroxybenzene (28) (2.0 g, 18.2 mmol) in AcOH (1.3 g, 21.7 mmol) was added boron trifluoride diethyl ether (98% in Et$_2$O, 2 mL). The mixture was reacted under microwave irradiation (300 W) for 1.5 min and then cooled to 25° C. The reaction mixture was dissolved in dichoromethane (10 mL) and H$_2$O (about 20 mL). The organic lay was washed with 10% NaHCO$_3$ and then with water, dried over MgSO$_4$ and concentrated. The crude was purified by column chromatography (SiO$_2$, CH$_2$Cl$_2$) to give 30. Yellow solid; yield: 10.4%; mp 76-77° C.; $^1$H-NMR (CDCl$_3$, 200 MHz): δ 2.58 (s, 3H), 5.79 (s, 1H), 6.79 (t, J=8.0 Hz, 1H), 7.10 (d, J=8.0 Hz, 1H), 7.26 (d, J=8.0 Hz, 1H), 12.45 (s, 1H); $^{13}$C-NMR (CDCl$_3$, 50 MHz): δ 26.73, 118.79, 119.52, 120.39, 121.44, 145.40, 149.50, 205.08; Anal. calcd for C$_8$H$_8$O$_3$: C, 63.15; H, 5.30. Found: C, 63.10; H, 5.33.

2,3-Methylenedioxyacetophenone (31). To a suspension of K$_2$CO$_3$ (1.24 g, 9.0 mmol) in DMF (10 mL) was added diiodomethane (2.4 g, 9.0 mmol). The mixture was heated to 100-110° C. and added a solution of 15 (1.0 g, 6.6 mmol) in DMF (5 mL) dropwise. The reaction mixture was stirred at 110° C. for 1 h and poured into crushed ice, extracted with CH$_2$Cl$_2$. The extract was washed with brine, dried over MgSO$_4$ and evaporated. The crude was purified by column chromatography (SiO$_2$, n-hexane: EtOAc=4:1) to give 31. White solid; yield: 61.0%; mp 89-91° C.; $^1$H-NMR (CDCl$_3$.

200 MHz): δ 2.58 (s, 3H), 6.07 (s, 2H), 6.87 (q, J=7.8 Hz, 1H), 6.95 (dd, J=8.0, 1.5 Hz, 1H), 7.35 (dd, J=8.0, 1.5 Hz, 1H); $^{13}$C-NMR (CDCl$_3$, 50 MHz): δ 30.29, 101.58, 112.51, 120.27, 121.25, 121.43, 148.00, 148.60, 195.58; Anal. calcd for C$_9$H$_8$O$_3$: C, 65.85; H, 4.91. Found: C, 65.75; H, 4.93.

6-Amino-2,3-methylenedioxyacetophenone (2). Compound 31 (0.63 g, 3.7 mmol) was allowed to react in the same manner as described in the preparation of compound 1 to give compound 2. Yellow solid; yield: 48.2%; mp 102-104° C.; $^1$H-NMR (DMSO-d$_6$.200 MHz): δ 2.44 (s, 3H), 5.92 (s, 2H), 6.14 (d, J=8.6 liz, 1H), 6.72 (s, 2H), 6.89 (d, J=8.6 Hz, 1H); $^{13}$C-NMR (DMSO-d$_6$, 50 MHz): δ 32.63, 101.08, 105.44, 107.71, 115.75, 136.77, 146.80, 148.78, 198.02; Anal. calcd for C$_9$H$_9$NO$_3$: C, 60.33; H, 5.06; N, 7.82. Found: C, 60.31; H, 5.09; N, 7.83.

4-Benzyloxy-3-methoxyacetophenone (35). To a solution of acetovanillone (33) (4.70 g, 28.3 mmol) in MeCN (60 mL) was added K$_2$CO$_3$ (8.05 g, 58.3 mmol) and KI (0.20 g, 1.2 mmol). The mixture was stirred under N$_2$ atmosphere and benzyl bromide (34) (4.0 mL, 34 mmol) was added dropwise. The reaction mixture was reflux for 24 h and then cooled to 25° C., then resulting precipitate was filtered off. The filtrate was evaporated and purified by column chromatography (SiO$_2$, n-hexane: CH$_2$Cl$_2$=1:2) to give 30. White solid; yield: 70.3%; mp 87-88° C.; $^1$H-NMR (CDCl$_3$. 200 MHz): δ 2.51 (s, 3H), 3.91 (s, 3H), 5.20 (s, 2H), 6.86 (d, J=8.2 Hz, 1H), 7.21-7.55 (m, 7H); $^{13}$C-NMR (CDCl$_3$, 50 MHz): δ 26.19, 56.05, 70.79, 110.53, 112.13, 123.07, 127.18, 128.10, 128.68, 130.72, 136.28, 149.49, 152.41, 196.80; Anal. calcd for C$_{16}$H$_{16}$O$_3$: C, 74.98; H, 6.29. Found: C, 75.02; H, 6.25.

4-Benzyloxy-3-methoxy-6-nitroacetophenone (36). To a solution of 35 (1.24 g, 4.83 mmol) in AcOH (15 mL) was added f. HNO$_3$ (1.5 mL, 36 mmol) dropwise at 0°±1° C. The mixture was stirred at 25° C. for 24 h and then poured into crushed ice. The precipitate was collected and washed with H$_2$O. The crude was purified by column chromatography (SiO$_2$, n-hexane: EtOAc=2:1) to give 36. Yellow solid; yield: 68.8%; mp 142-143° C.; $^1$H-NMR (CDCl$_3$. 200 MHz): δ 2.46 (s, 3H), 3.95 (s, 3H), 5.19 (s, 2H), 6.74 (s, 1H), 7.30-7.48 (m, 5H), 7.64 (s, 1H); $^{13}$C-NMR (CDCl$_3$, 50 MHz): δ 30.41, 56.67, 71.39, 108.78, 127.56, 128.56, 128.84, 133.08, 135.19, 138.21, 148.54, 154.53, 200.13; Anal. calcd for C$_{16}$H$_{15}$NO$_5$: C, 63.78; H, 5.02; N, 4.65. Found: C, 63.82; H, 5.00; N, 4.63.

2-Amino-4-benzyloxy-5-methoxyacetophenone (3). To a solution of 36 (1.0 g, 3.32 mmol) in anhydrous EtOH (100 mL) was added Tin chloride dihydrate (3.7 g, 16.4 mmol). The mixture was reflux for 2 h and then cooled to 25° C., and poured in 5% NaHCO$_3$ solution. The precipitate was collected and washed with H$_2$O and then extracted with EtOAc. The extract was wash with H$_2$O, dried over MgSO$_4$ and evaporated. The crude was purified by column chromatography (SiO$_2$, n-hexane: EtOAc=1:1) to give 7c. Yellow solid; yield: 72.2%; mp 135-137° C.; $^1$H-NMR (DMSO-d$_6$.200 MHz): δ 2.39 (s, 3H), 3.66 (s, 3H), 5.03 (s, 2H), 6.38 (s, 1H), 7.05 (s, 2H), 7.10 (s, 1H), 7.30-7.50 (m, 5H); $^{13}$C-NMR (DMSO-d$_6$, 50 MHz): δ 28.21, 56.94, 69.87, 100.05, 109.70, 115.40, 128.34, 128.49, 128.93, 136.83, 139.45, 148.74, 154.64, 198.06; Anal. calcd for C$_{16}$H$_{17}$NO$_3$: C, 70.83; H, 6.32; N, 5.16. Found: C, 70.82; H, 6.30; N, 5.20.

2-(2-Fluorophenyl)-5-hydroxy-6-methoxyquinolin-4-one (37). To a solution of 16 (0.2 g, 0.67 mmol) in CH$_2$Cl$_2$ (3 mL) was added 5 mL of BCl$_3$ solution (1 M in CH$_2$Cl$_2$) dropwise at 0°±1° C. The mixture was stirred at 25±1° C. for 2 h and then poured into crushed ice, extracted with EtOAc. The organic layer was washed with H$_2$O, dried over MgSO$_4$ and evaporated. The crude was purified by column chromatography (SiO$_2$, CHCl$_3$: MeOH=15:1) and recrystallized from MeOH to give 37. Yellow solid; yield: 24.1%; mp 268-270° C.; MS (EI, 70 eV): m/z 285 (M$^+$); IR (KBr): 1604.77 (C=O) cm$^{-1}$; $^1$H-NMR (DMSO-d$_6$. 200 MHz): δ 3.78 (s, 3H), 6.11 (s, 1H), 7.01 (d, J=7.4 Hz, 1H), 7.36-7.48 (m, 3H), 7.54-7.72 (m, 2H), 12.25 (s, 1H), 14.54 (s, 1H); $^{13}$C-NMR (DMSO-d$_6$, 50 MHz): δ 55.80, 106.22, 106.43, 112.88, 116.36 (d, J=23 Hz), 120.81, 121.96 (d, J=13.5 Hz), 125.04, 130.85, 132.67 (d, J=8.6 Hz), 135.09, 141.02, 146.27, 149.29, 158.92 (d, J=247.7 Hz), 181.97; Anal. calcd for C$_{16}$H$_{12}$FNO$_3$: C, 67.36; H, 4.24; N, 4.91. Found: C, 67.32; H, 4.26; N, 4.89.

2-(3-Fluorophenyl)-5-hydroxy-6-methoxyquinolin-4-one (38) was obtained from 17 and BCl$_3$. Yellow solid; yield: 26.7%; mp 274-276° C.; MS (EI, 70 eV): m z 285 (M$^+$); IR (KBr): 1606.70 (C=O) cm$^{-1}$; $^1$H-NMR (DMSO-d$_6$, 200 MHz): δ 3.77 (s, 3H), 6.33 (s, 1H), 7.11 (d, J=8.8 Hz, 1H), 7.33-7.48 (m, 2H), 7.51-7.76 (m, 3H), 12.09 (s, 1H), 14.56 (s, 1H); $^{13}$C-NMR (DMSO-d$_6$, 50 MHz): δ 57.19, 104.82, 106.97, 113.39, 115.09 (d, J=23 Hz), 118.06 (d, J=21 Hz), 121.07, 124.32, 131.64 (d, J=9.0 Hz), 135.61, 136.16 (d, J=8.0 Hz), 141.49, 149.64, 150.12, 162.64 (d, J=242.5 Hz), 182.69; Anal. calcd for C$_{16}$H$_{12}$FNO$_3$: C, 67.36; H, 4.24; N, 4.91. Found: C, 67.35; H, 4.24; N, 4.92.

2-(4-Fluorophenyl)-5-hydroxy-6-methoxyquinolin-4-one (39) was obtained from 18 and BCl$_3$. Yellow solid; yield: 23.0%; mp 307-309° C.; MS (EI, 70 eV): m/z 285 (M$^+$); IR (KBr): 1610.56 (C=O) cm$^{-1}$; $^1$H-NMR (DMSO-d$_6$, 200 MHz): δ 3.76 (s, 3H), 6.25 (s, 1H), 7.08 (d, J=9.0 Hz, 1H), 7.34-7.43 (m, 3H), 7.82-7.89 (m, 2H), 12.01 (s, 1H), 14.60 (s, 1H); $^{13}$C-NMR (DMSO-d$_6$, 50 MHz): δ 57.19, 104.53, 106.84, 113.23, 116.47 (d, J=22 Hz), 120.99, 130.55 (d, J=9.0 Hz), 135.62, 141.45, 149.69, 150.64, 164.02 (d, J=247 Hz), 182.59; Anal. calcd for C$_{16}$H$_{12}$FNO$_3$: C, 67.36; H, 4.24; N, 4.91. Found: C, 67.36; H, 4.24; N, 4.92.

2-(2-Fluorophenyl)-5,6-dihydroxyquinolin-4-one (40). To a solution of 19 (0.1 g, 0.35 mmol) in anhydrous MeOH (30 mL) was hydrogenated in the presence of 10% Pd/C (0.2 g) at 25±2° C. for 40 h. The catalyst was filtered off and the filtrate was evaporated. The crude was purified by column chromatography (SiO$_2$, EtOAc: MeOH=30:1) to give 40. White solid; yield: 13.7%; mp 152-154° C.; MS (EI, 70 eV): m/z 271 (M$^+$); IR (KBr): 1622.13 (C=O) cm$^{-1}$; $^1$H-NMR (DMSO-d$_6$, 200 MHz): δ 6.03 (s, 1H), 7.15 (d, J=8.8 Hz, 1H), 7.30-7.70 (m, 6H), 9.72 (s, 1H), 11.76 (s, 1H); $^{13}$C-NMR (DMSO-d$_6$, 50 MHz): δ 107.67, 108.57, 116.75 (d, J=21.5 Hz), 120.54, 122.67, 123.36, 125.42, 126.70, 131.22, 132.49, 134.35, 144.30, 154.29, 159.43 (d, J=248.5 Hz), 176.82; Anal. calcd for C$_{15}$H$_{10}$FNO$_3$: C, 66.42; H, 3.72; N, 5.16. Found: C, 66.38; H, 3.70; N, 5.15.

2-(3-Fluorophenyl)-5,6-dihydroxyquinolin-4-one (41) was obtained from 20. White solid; yield: 15.0%; mp 307-308° C.; MS (EI, 70 eV): m/z 271 (M$^+$); IR (KBr): 1608.63 (C=O) cm$^{-1}$; $^1$H-NMR (DMSO-d$_6$ 200 MHz): δ 6.25 (s, 1H), 7.15 (d, J=8.8 Hz, 1H), 7.30-7.50 (m, 2H), 7.50-7.80 (m, 4H), 9.72 (s, 1H), 11.60 (s, 1H); $^{13}$C-NMR (DMSO-d$_6$, 50 MHz): δ 106.38, 107.57, 114.65 (d, J=23 Hz), 117.38 (d, J=21.5 Hz), 120.91, 122.62, 123.91, 126.81, 131.52 (d, J=8.5 Hz), 134.45, 137.17, 147.66, 154.36, 162.70 (d, J=242 Hz), 176.82; Anal. calcd for C$_{15}$H$_{10}$FNO$_3$: C, 66.42; H, 3.72; N, 5.16. Found: C, 66.43; H, 3.74; N, 5.13.

2-(4-Fluorophenyl)-5,6-dihydroxyquinolin-4-one (42) was obtained from 21. White solid; yield: 13.9%; mp 332-334° C.; MS (EI, 70 eV): m/z 271 (M$^+$); IR (KBr): 1614.42 (C=O) cm$^{-1}$; $^1$H-NMR (DMSO-d$_6$, 200 MHz): δ 6.18 (s, 1H), 7.14 (dd, J=9.0, 2.8 Hz, 1H), 7.33-7.42 (m, 3H), 7.59 (d, J=8.8 Hz, 1H), 7.79-7.86 (m, 2H), 9.70 (s, 1H), 11.59 (s, 1H); $^{13}$C-NMR (DMSO-d$_6$, 50 MHz): δ 106.24, 107.68, 116.39 (d, J=21.5 Hz), 120.71, 122.48, 126.73, 130.19 (d, J=8.5 Hz), 131.38, 134.42, 148.24, 154.20, 163.70 (d, J=247.5 Hz), 176.81; Anal. calcd for $C_{15}H_{10}FNO_3$: C, 66.42; H, 3.72; N, 5.16. Found: C, 66.47; H, 3.69; N, 5.14.

2-(2-Fluorophenyl)-7-hydroxy-6-methoxyquinolin-4-one (43). Compound 22 (0.3 g, 0.80 mmol) was allowed to react in the same manner as described in the preparation of compound 40 to give 43. White solid; yield: 61.3%; mp 277-279° C.; MS (EI, 70 eV): m/z 285 (M+); IR (KBr): 1622.13 (C=O) cm$^{-1}$; $^1$H-NMR (DMSO-d$_6$ 200 MHz): δ 3.82 (s, 3H), 6.04 (s, 1H), 7.01 (s, 1H), 7.32-7.50 (m, 3H), 7.50-7.67 (m, 2H), 10.22 (s, 1H), 11.68 (s, 1H); $^{13}$C-NMR (DMSO-d$_6$, 50 MHz): δ 55.52, 102.72, 105.37, 108.20, 116.28 (d, J=22.5 Hz), 118.07, 122.94, 124.92, 130.75, 131.99 (d, J=7.95 Hz), 136.45, 143.61, 146.58, 151.59, 158.98 (d, J=246.9 Hz), 175.30; Anal. calcd for $C_{16}H_{12}FNO_3$: C, 67.36; H, 4.24; N, 4.91. Found: C, 67.37; H, 4.26; N, 4.90.

2-(3-Fluorophenyl)-7-hydroxy-6-methoxyquinolin-4-one (44) was obtained from 23. White solid; yield: 44.8%; mp 326-328° C.; MS (EI, 70 eV): m/z 285 (M+); IR (KBr): 1606.70 (C=O) cm$^{-1}$; $^1$H-NMR (DMSO-d$_6$, 200 MHz): δ 3.81 (s, 3H), 6.24 (s, 1H), 7.12 (s, 1H), 7.27-7.42 (m, 2H), 7.47-7.70 (m, 3H), 10.20 (s, 1H), 11.44 (s, 1H); $^{13}$C-NMR (DMSO-d$_6$, 50 MHz): δ 55.92, 103.35, 104.70, 106.67, 114.59 (d, J=23 Hz), 117.26 (d, J=21 Hz), 118.85, 123.85, 131.47 (d, J=8.0 Hz), 136.85, 137.16, 146.94, 147.33, 151.93, 162.69 (d, J=242.5 Hz), 176.37; Anal. calcd for $C_{16}H_{12}FNO_3$: C, 67.36; H, 4.24; N, 4.91. Found: C, 67.32; 1-1, 4.22; N, 4.93.

2-(4-Fluorophenyl)-7-hydroxy-6-methoxyquinolin-4-one (45) was obtained from 24. White solid; yield: 42.5%; mp 352-354° C.; MS (EI, 70 eV): m/z 285 (M+); IR (KBr): 1610.56 (C=O) cm$^{-1}$; $^1$H-NMR (DMSO-d$_6$, 200 MHz): δ 3.80 (s, 3H), 6.19 (s, 1H), 7.11 (s, 1H), 7.20-7.50 (m, 3H), 7.70-7.90 (m, 2H); $^{13}$C-NMR (DMSO-d$_6$, 50 MHz): δ 55.89, 103.50, 104.55, 106.18, 116.30 (d, J=21.5 Hz), 118.41, 130.03 (d, J=8.5 Hz), 131.57, 137.22, 147.00, 148.01, 152.21, 163.58 (d, J=246 Hz), 175.93; Anal. calcd for $C_{16}H_{12}FNO_3$: C, 67.36; H, 4.24; N, 4.91. Found: C, 67.39; H, 4.20; N, 4.89.

2-(3-Fluorophenyl)-6-methoxyquinoline-4,5-diyl bis(dibenzyl phosphate) (48)

Method A: To a stirred solution of 38 (0.12 g, 0.42 mmol) in dry THF (20 mL) was added NaH (96 mg, 4 mmol) at 0°±1° C. After it was stirred for 1 h, tetrabenzyl pyrophosphate (46) (430 mg, 0.8 mmol) was added and stirring was continued for 25 min. The reaction mixture was filtered and washed with CH$_2$Cl$_2$. The filtrate was concentrated under vacuum at a temperature below 30° C. The residue was purified by column chromatography (SiO$_2$, n-hexane: EtOAc) to give 48. Liquid; yield: 95.0%; Method B: To a stirred solution of 38 (1.85 g, 6.5 mmol) in acetonitrile (50 mL) was added CCl$_4$ (10 eq.) at −10° C. N,N-diisopropylethylamine (DIPEA)(4.2 eq.) followed by N,N-dimethylaminopyridine (DMAP)(0.2 eq.) were added. One minute later, dropwise addition of dibenzyl phosphate (47) was begun. When the reaction was complete as determined by TLC, 0.5 M aqueous KH$_2$PO$_4$ was added and the mixture was allowed to warm to room temperature and extracted with EtOAc. The organic layer was washed with H$_2$O, dried over MgSO$_4$ and evaporated. The crude was purified by column chromatography (EA: n-hex=1:1) to give 48. Liquid; yield: 96.0%. Compound 48: MS (EI, 70 eV): m/z 805 (M+); $^1$H-NMR (DMSO-d$_6$, 200 MHz): δ 3.87 (s, 3H), 5.10 (s, 2H), 5.14 (s, 2H), 5.18 (s, 2H), 5.22 (s, 2H), 7.20-7.36 (m, 21H), 7.47-7.60 (m, 1H), 7.72-7.84 (m, 4H), 8.01 (d, J=9.4 Hz, 1H); $^{13}$C-NMR (DMSO-d$_6$, 50 MHz): δ 57.27, 69.63, 69.74, 70.12, 70.23, 110.20, 113.57, 114.03, 116.23, 116.92, 117.35, 119.48, 123.28, 128.10, 128.38, 128.70, 128.79, 128.85, 128.95, 131.35, 131.51, 135.79, 135.94, 136.32, 136.47, 140.41, 140.56, 145.39, 149.74, 149.82, 153.44, 153.57, 153.92, 160.71, 165.56; Anal. ($C_{44}H_{38}FNO_9P_2$) C, H, N.

2-(3-Fluorophenyl)-6-methoxyquinoline-4,5-diyl bis(dihydrogen phosphate) (49). A suspension of 48 (153 mg, 0.19 mmol) in anhydrous MeOH (10 mL) was hydrogenated in the presence of 10% Pd/C (80 mg) at 25° C. for 15 min. The catalyst and precipitate were collected and dissolved in 10% NaHCO$_3$ solution and then filtered. The filtrate was acidified with dil aq HCl and the precipitate was then collected and washed with acetone to give 49. Yellow solid; yield: 87%; mp>300° C.; MS (ESI): m/z 444 (M−H)−; $^1$H-NMR (D$_2$O, 200 MHz): δ 3.85 (s, 3H), 7.29 (t, J=8.0 Hz, 1H), 7.43-7.68 (m, 4H), 7.72-7.92 (m, 2H); Anal. ($C_{16}H_{14}FNO_9P_2$) C, H, N.

2-(3-Fluorophenyl)-6-methoxyquinoline-4,5-diyl bis(disodium phosphate) (50). To a stirred solution of NaHCO$_3$ (0.67 g, 8.0 mmol) in H$_2$O (20 mL) was added 49 (0.89 g, 2.0 mmol) at 0°±1° C. After the addition was complete, the reaction mixture was removed from the ice bath, stirred at 25° C. for 10 min and the filtered though celite, after no dissolution from the solid was observed. The resulting filtrate (15 mL) was poured into acetone (60 mL), and kept it in an ice bath for 1 h. The precipitate was collected and washed with ice-cooled acetone (10 mL×5). The solid was dried under vacuum to give 50. White solid; yield: 52.3%; mp>300° C.; MS (ESI): m/z 534 (M+H)+; $^1$H-NMR (D$_2$O, 200 MHz): δ 3.81 (s, 3H), 7.10 (t, J=8.2 Hz, 1H), 7.34-7.52 (m, 2H), 7.60-7.72 (m, 4H); Anal. ($C_{16}H_{10}FNNa_4O_9P_2$) C, H, N.

Dibenzyl 2-(3-fluorophenyl)-6-methoxy-4-oxo-1,4-dihydroquinolin-5-yl phosphate (51). A suspension of 48 (2.42 mg, 3.0 mmol) in anhydrous MeOH (10 mL) was stirred at 25° C. for 24 h. The reaction mixture was concentrated under vacuum at a temperature below 30° C. The residue was purified by column chromatography (SiO$_2$, n-hexane: EtOAc) to give 51. Yellow solid; yield: 80.0%; mp 136-138° C.; MS (ESI): m/z 544.5 (M−H)−; $^1$H-NMR (DMSO-d$_6$, 200 MHz): δ 3.75 (s, 3H), 5.28 (s, 2H), 5.31 (s, 2H), 6.27 (s, 1H), 7.26-7.50 (m, 11H), 7.50-7.78 (m, 6H); $^{13}$C-NMR (DMSO-d$_6$, 50 MHz): δ 57.19, 69.32, 69.44, 108.51, 114.46, 114.93, 116.74, 117.38, 119.24, 123.92, 128.04, 128.51, 128.82, 131.49, 131.65, 136.74, 137.07, 137.23, 147.00, 160.29, 176.88; Anal. ($C_{30}H_{25}FNO_6P$)C, H, N.

2-(3-Fluorophenyl)-6-methoxy-4-oxo-1,4-dihydroquinolin-5-yl dihydrogen phosphate (52). Compound 51 (0.25 g, 0.46 mmol) was allowed to react in the same manner as described in the preparation of compound 49 to give 52. Yellow solid; yield: 63.7%; mp 179-181° C.; MS (ESI): m/z 366 (M+H)+; $^1$H-NMR (D$_2$O+NaOD, 200 MHz): δ 3.76 (s, 3H), 6.53 (s, 1H), 7.05 (1, =8.4 Hz, 1H), 7.24-7.60 (m, 5H); Anal. ($C_{16}H_{13}FNO_6P$) C, H, N.

Sodium 2-(3-fluorophenyl)-6-methoxy-4-oxo-1,4-dihydroquinolin-5-yl phosphate (53). Compound 52 (0.73 g, 2.0 mmol) was allowed to react in the same manner as described in the preparation of compound 50 to give 53. Yellow solid; yield: 48.0%; mp>300° C.; MS (ESI): m/z 410 (M+H)+; $^1$H-NMR (D$_2$O, 200 MHz): δ 3.72 (s, 3H), 6.54 (s, 3H), 6.99 (t, J=7.8 Hz, 1H), 7.15-7.55 (m, 5H); Anal. ($C_{16}H_{11}FNNa_2O_6P$)C, H, N.

I-2. Anticancer Activity
In Vitro Tests of Compounds

MTT (3-(4,5-Dimethylthiazol-2-yl)-2,5-diphenyltetrazolium bromide) assays.[21,22] HL-60, HCT-116, Hep 3B, H460, Detroit 551 and HT29/FuR cells were treated with tested compounds for the indicated periods. After treatment, cells were washed once with PBS and incubated with MTT (Sigma, St. Louis, Mo., USA) for 2 h. The formazan precipitate was dissolved in 150 μL of DMSO, and the absorbance was measured with an ELISA reader at 570 nm.

Results

Figure 3A:
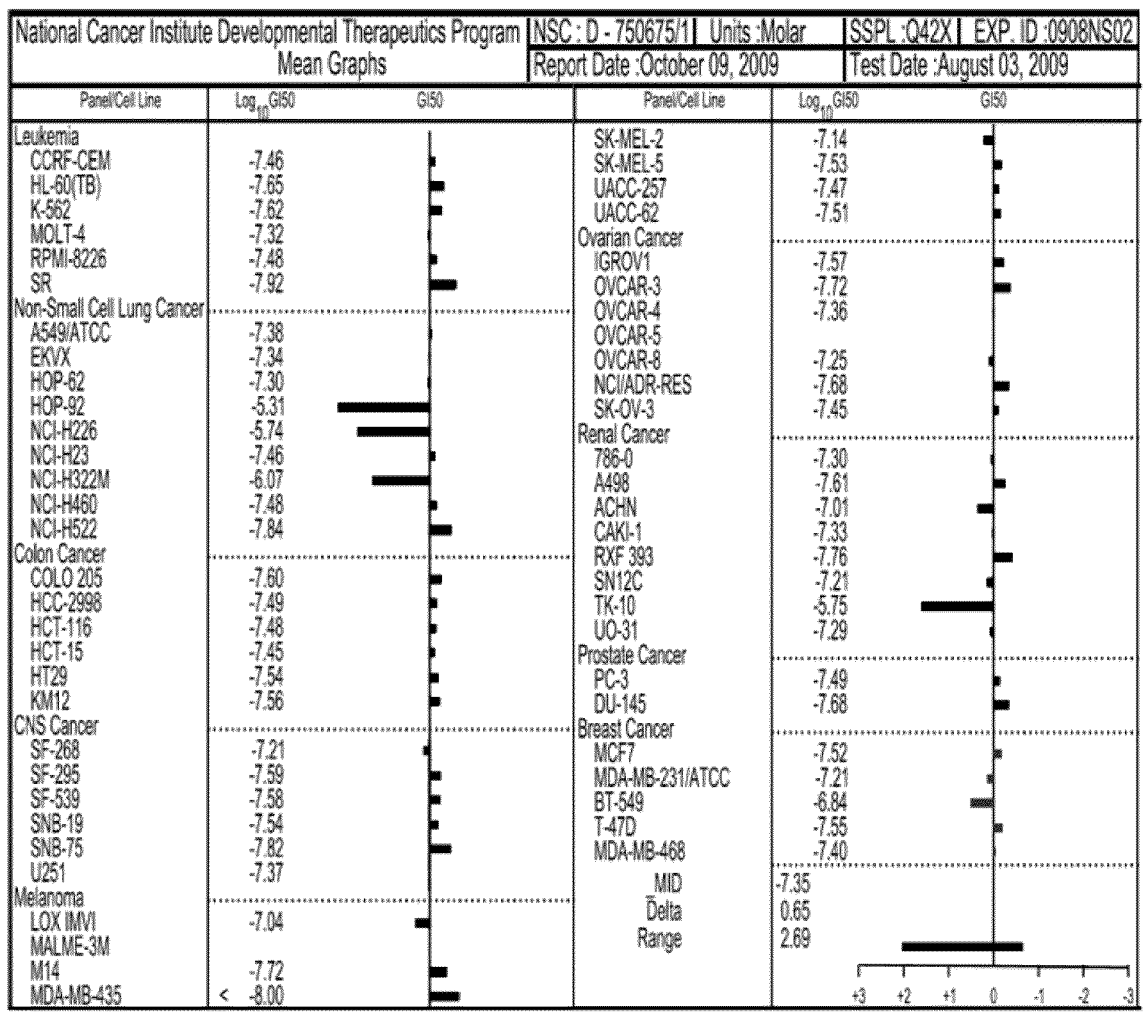
FIGS. 3A-3C show differential activity patterns for 2-3-Fluorophenyl)-5-hydroxy-6-methoxyquinolin-4-one (compound 38) against 60 human cancer cell lines. MG-MID: mean of log X values (X=GI$_{50}$, TGI, and LC$_{50}$). Delta; logarithm of the difference between the MG-MID and the log X of the most sensitive cell line. Range: logarithm of the difference between the log X of the most resistant cell line and the log X of the most sensitive cell line.
Figure 3B:
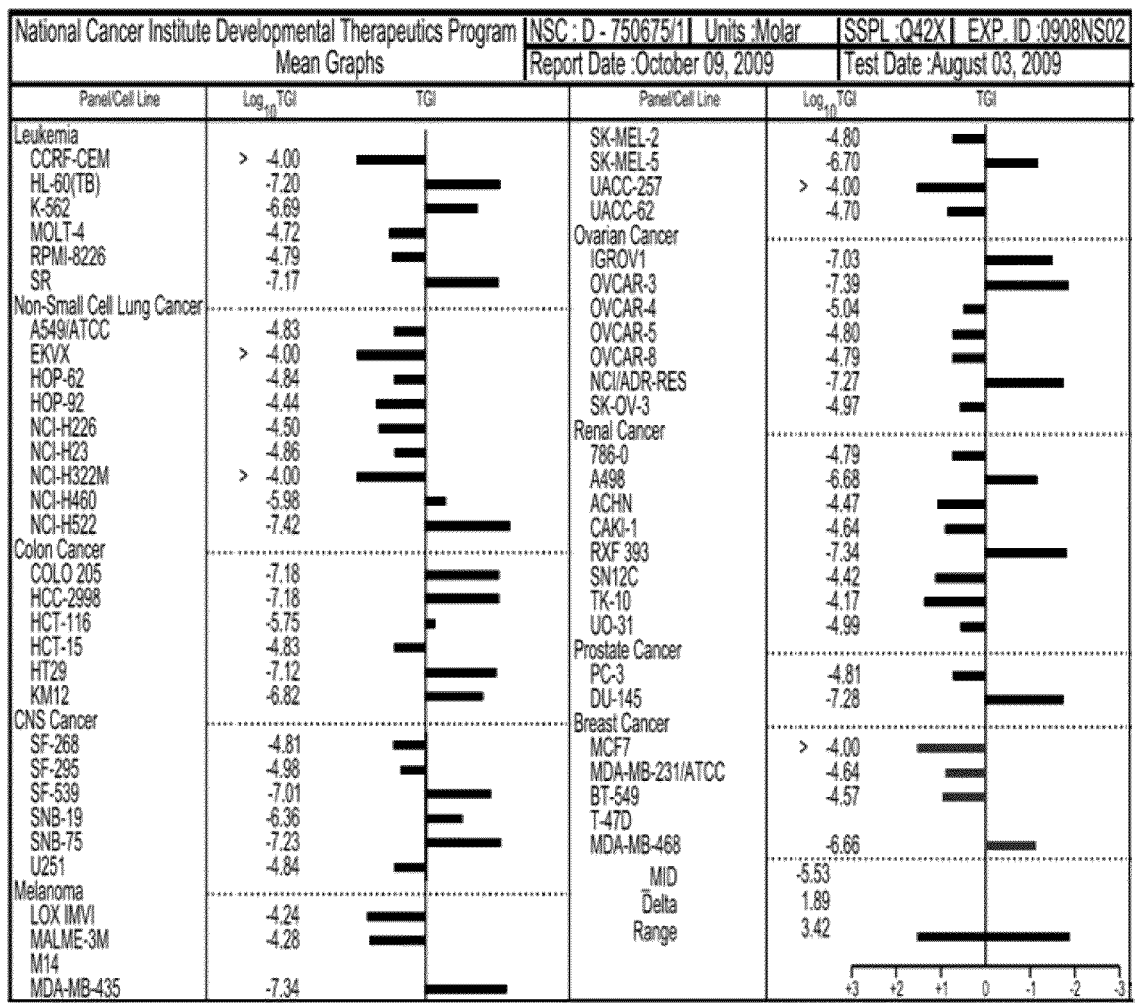
Figure 3C:
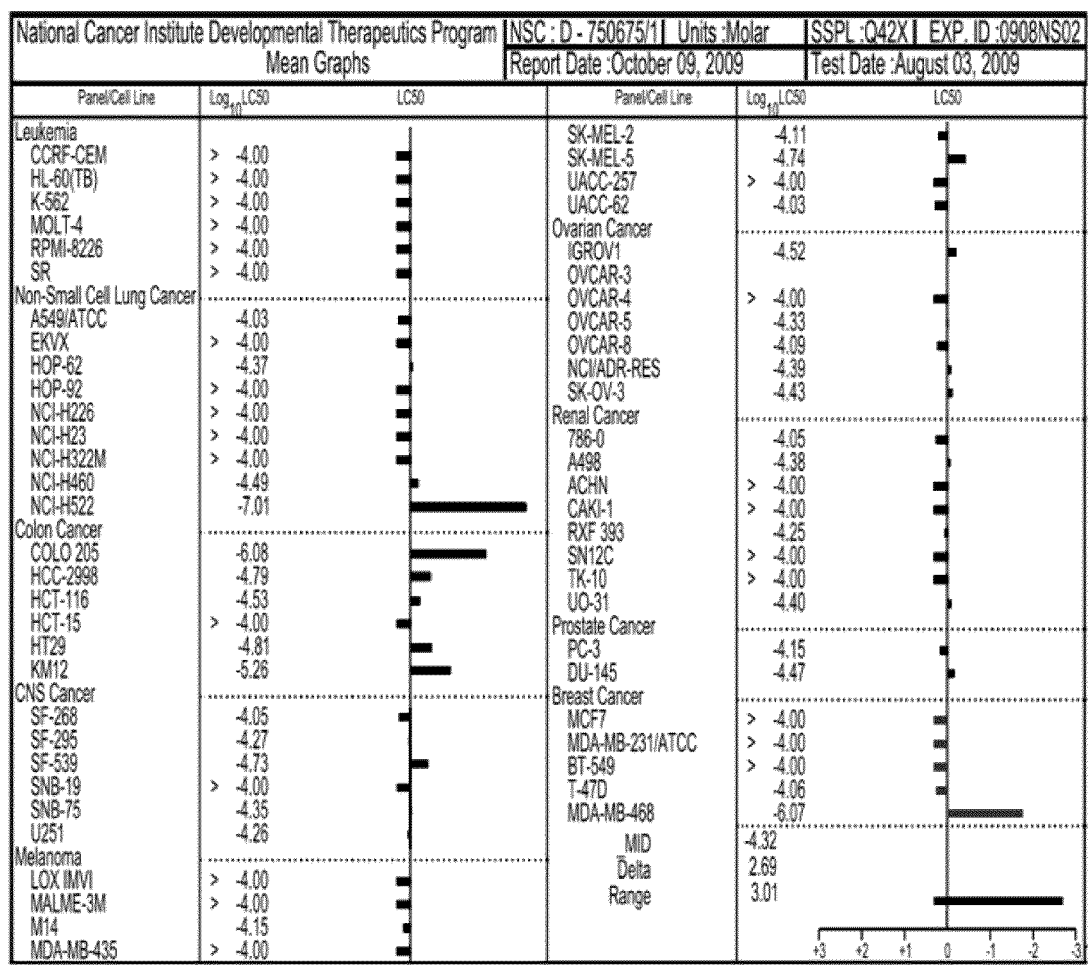

The cytotoxicity of 5,6-(6,7-) disubstituted 2-(fluorophenyl)quinolin-4-ones (16-21,37-45) and CHM-2133, were screened against HL-60, HCT-116, Hep3B, H-460 and Detroit 551 normal human cell, and the results were summarized in Table 1. Among 5,6-dimethoxy derivatives (16-18), the 3-fluoro derivative (17) exhibited the strongest cytotoxicity, though relatively weaker than that of our positive control CHM-2133. Meanwhile, both compounds 19 and 20, having methylenedioxy entity bridging the 5,6-position of their quinoline ring, demonstrated significant cytotoxicity, although weaker than CHM-2133. Then, while all of the three 5-hydroxy-6-methoxy derivatives (37-39) showed significant cytotoxicity, compounds 37 and 38, with 2'- or 3'-fluorosubstituent on 2-phenyl group, demonstrated greater cytotoxicity, but lower toxicity toward Detroit 551 normal human cell than CHM-2133. Following the same trend, it was found that, among 5,6-dihydroxy (40-42) and 7-hydroxy-6-methoxy (43-45) derivatives, those with 2'-fluoro (40,43) and 3'-fluoro group (41, 44) demonstrated greater cytotoxicity. In general, the cytotoxicity of 4'-fluorophenyi derivatives (18, 21, 39, 42 and 45) was found to be weaker than 2'-fluorophenyl derivatives (16, 19, 37, 40 and 43) and 3'-fluorophenyl derivatives (17, 20, 38, 41 and 44). Among them, compounds 37 and 38 are considered the most promising anticancer agents. None of the tested compounds showed noticeable cytotoxicity toward the Detroit 551 normal human cells. Below and Table 1 shows structures and cytotoxicities of CHM-2133 and target compounds 16-21 and 37-45. FIGS. 3A-3C show differential activity patterns for 2-(3-Fluorophenyl)-5-hydroxy-6-methoxyquinolin-4-one (compound 38) against 60 human cancer cell lines.

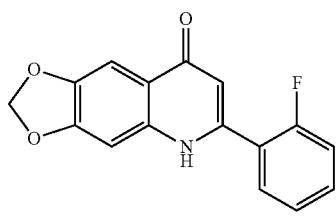

CHM-2133

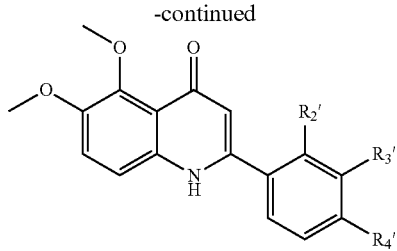

16-18

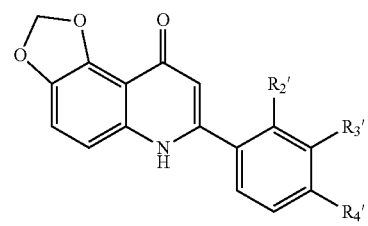

19-21

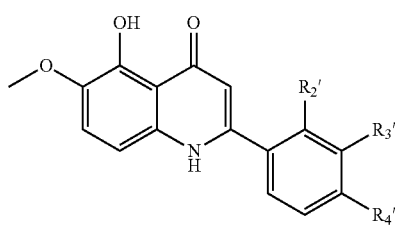

37-39

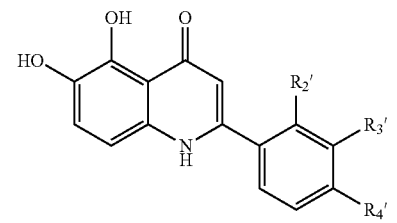

40-42

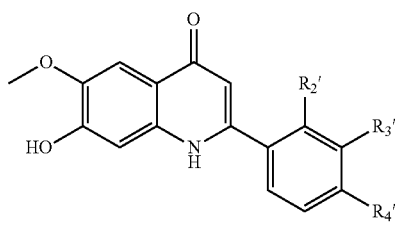

43-45

TABLE 1

| Comp'd | R₂ | R₃ | R₄ | HL-60 | HCT116 | Hep3B | H460 | Detroit 551 | HT29/5FuR |
|---|---|---|---|---|---|---|---|---|---|
| | | | | | | IC₅₀ [a](μM) | | | |
| CHM-2133 | — | — | — | 0.08 | 0.15 | 0.13 | 0.14 | 8.2 | — |
| 16 | F | H | H | 3.7 | >20 | >20 | >20 | >20 | 2.03 |
| 17 | H | F | H | 1.3 | 1.2 | 2.6 | 3.5 | 100 | 1.96 |
| 18 | H | H | F | 2.0 | >20 | >20 | >20 | >20 | 2.02 |
| 19 | F | H | H | 1.0 | 2.1 | 1.9 | 4.5 | >10 | 0.69 |
| 20 | H | F | H | 0.7 | 2.5 | 2.4 | 3.2 | >5 | 0.82 |

TABLE 1-continued

| Comp'd | $R_2$ | $R_3$ | $R_4$ | HL-60 | HCT116 | Hep3B | H460 | Detroit 551 | HT29/5FuR |
|---|---|---|---|---|---|---|---|---|---|
| 21 | H | H | F | >10 | >10 | >10 | >10 | >10 | 0.53 |
| 37 | F | H | H | 0.067 | 0.05 | 0.05 | 0.11 | 10 | 0.20 |
| 38 | H | F | H | 0.039 | 0.073 | 0.078 | 0.088 | >50 | 0.26 |
| 39 | H | H | F | 1.8 | 2.4 | 11.0 | 8.8 | >25 | 0.33 |
| 40 | F | H | H | 0.5 | 0.6 | 3.9 | 4.1 | >100 | 1.63 |
| 41 | H | F | H | 0.3 | 8.2 | 6.9 | 6.1 | >100 | 0.53 |
| 42 | H | H | F | 38.6 | >100 | 100 | 100 | >100 | NA[b] |
| 43 | F | H | H | 1.3 | 5.8 | 5.3 | 4.4 | 29.7 | 0.29 |
| 44 | H | F | H | 0.9 | 1.1 | 5.3 | 4.8 | 10 | 0.30 |
| 45 | H | H | F | 38.2 | >100 | >100 | >100 | >100 | 0.37 |

Human tumor cells were treated with different concentrations of samples for 48 h.
[a]Data was presented as $IC_{50}$ (μM, the concentration of 50% proliferation-inhibitory effect).
[b]NA = Not assayed.

In Vivo Antitumor Activity Assay.

The Hep-3B tumor cell line was purchased from American Type Culture Collection (ATCC™HB-8064, human hepatocellular carcinoma cells). The culture medium contained DMEM, 90%; Fetal Bovine Serum, 10% and 1% penicillin-streptomycin. The tumor cells were incubated in an atmosphere containing 5% $CO_2$ at 37° C.

Balb/c Nude mice used in this study were male, 4-6 weeks age, weighing 18-20 g and provided by National Animal Center. All animals were housed in Individually Ventilated Cages Racks (IVC Racks, 36 Mini Isolator system) under Specific Pathogen-Free (SPF) condition throughout the experiment. Each cage (in cm, 26.7 length×20.7 width×14.0 height) was sterilized with autoclave and contained 8 mice, and then the animals were maintained in a hygienic environment under controlled temperature (20-24° C.) and humidity (40%-70%) with 12 hour light/dark cycle. The animals were given free access to sterilized lab chow and sterilized distilled water ad libitum. All aspects of this work, i.e., housing, experimentation and disposal of animals were performed in general accordance with the Guide for the Care and Use of Laboratory Animals (National Academy Press, Washington, D.C., 1996).

In the xenotraft tumor model of human hepatocellular carcinoma cell lines (Hep-3B, ATCC HB-8064) in male Balb/c Nude mice, the compounds 49 at doses at 7.5, 15 and 30 mg/kg (i.v. or p.o., bid) was administered five days per week for four consecutive weeks by p.o, or i.v. and ceased at Day 28. The compounds 52 at doses at 7.5, 15 and 30 mg/kg (i.v. or p.o., qd) was administered five days per week for four consecutive weeks and ceased at Day 28. The tumor size, body weight was monitored and recorded for 28 days. Human hepatocellular carcinoma cells (HEP-3B ATCC HB-8064) with $2\times10^6$ cells in 0.1 ml were injected subcutaneously into the right flank of the mice. When the tumor growth reached >100 $mm^3$ in volume (assumed as day 0), the tumor-bearing animals were assigned into several groups (8 animals in each group) for study.

The body weight and tumor size were measured and recorded every 7 days during the experimental periods of 28 days. Tumor volume ($mm^3$) was estimated according to the formula of length×(width)×0.5 in $mm^3$. Tumor growth inhibition was calculated as T/C (treatment/control) by the following formula: $T/C=(Tn-T_0)/(Cn-C_0)\times100\%$ ($T_0$: Tumor volume of treated group in Day 0; Tn: Tumor volume of treated group in Day n; $C_0$: Tumor volume of control group in Day 0; Cn: Tumor volume of control group in Day n).

Results

Figure 4A:
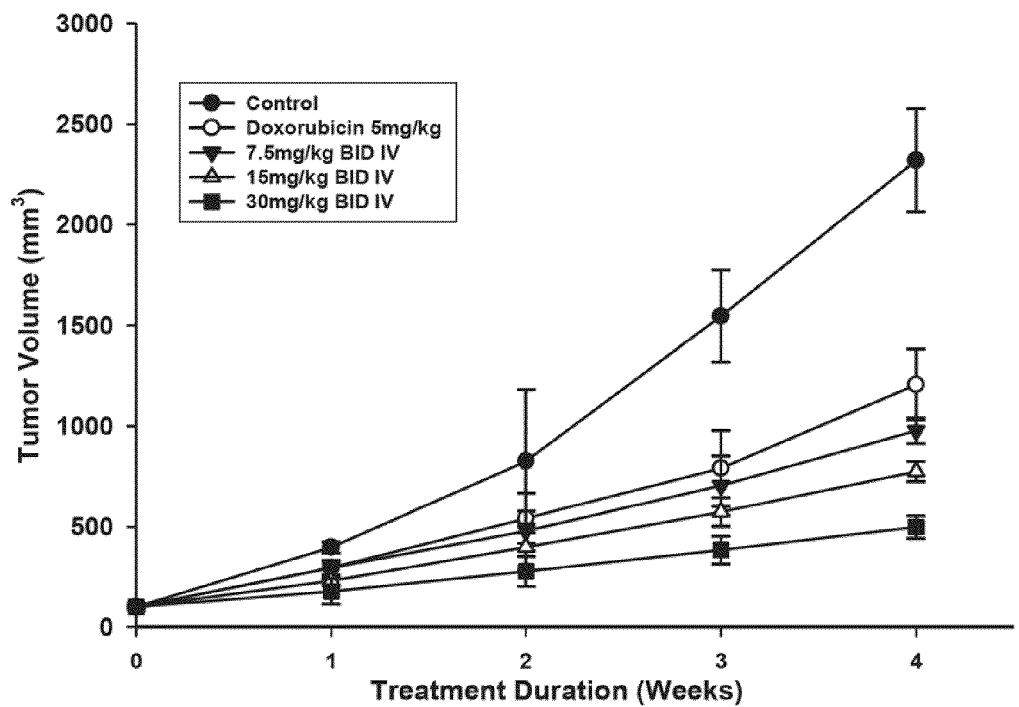
FIGS. 4A-4F show (A) Mean tumor volume-time profiles, (B) Mean tumor weight-time profiles and (C) Mean body weight-time profiles in Hep3B xenograft nude mice (n=11) following iv dosing of doxorubicin at 5 mg/kg (qd) and compound 49 at 7.5, 15, and 30 mg/kg (bid) five days per week for four consecutive weeks; (D) Mean tumor volume-time profiles, (E) Mean tumor weight-time profiles and (F) Mean body weight-time profiles in Hep3B xenograft nude mice (n=11) following oral dosing of doxorubicinat 10 mg/kg (qd) and compound 49 at 7.5, 15, and 30 mg/kg (bid) five days per week for four consecutive weeks.
Figure 4B:
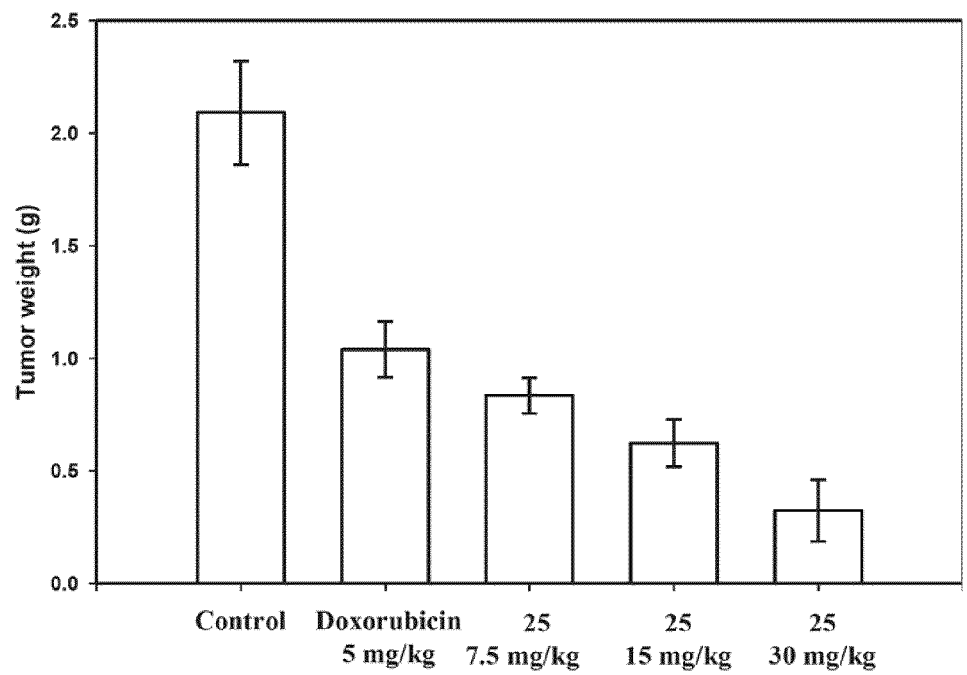
Figure 4C:
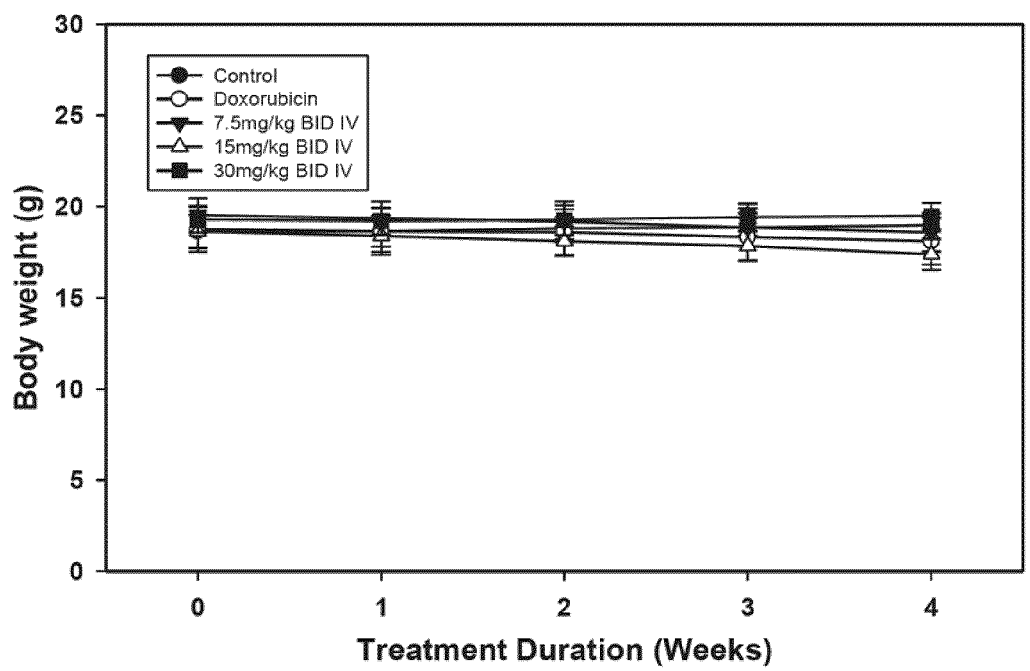
Figure 4D:
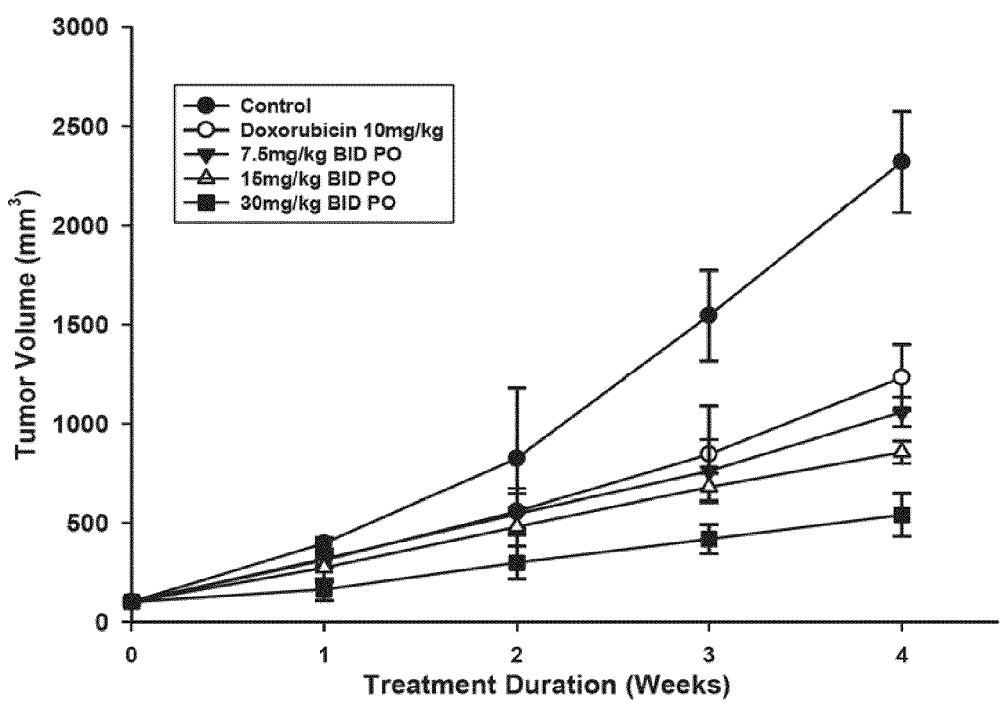
Figure 4E:
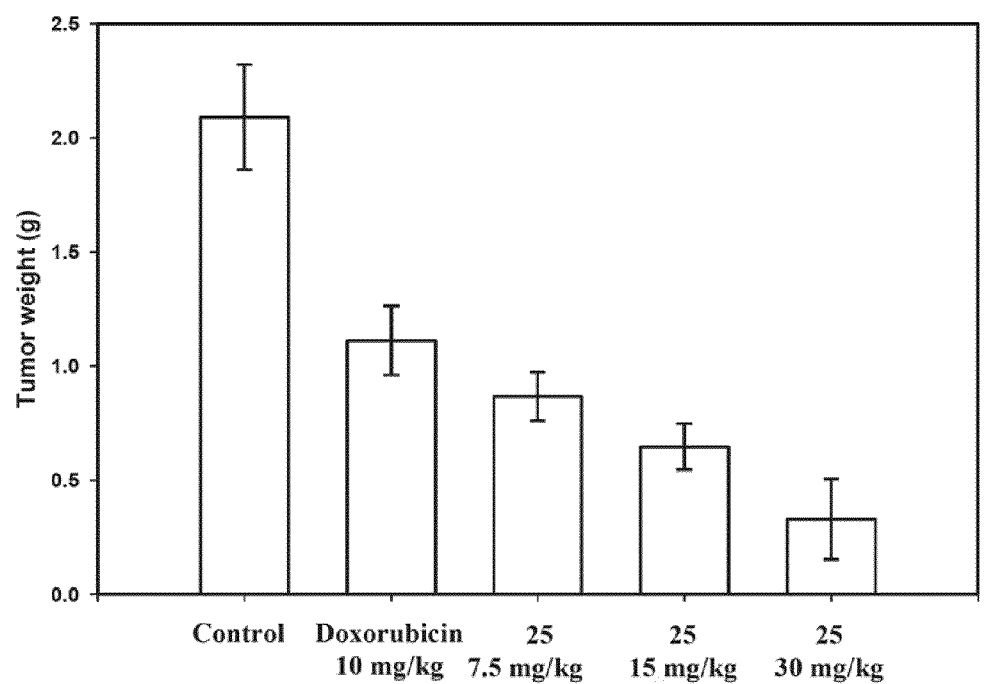
Figure 4F:
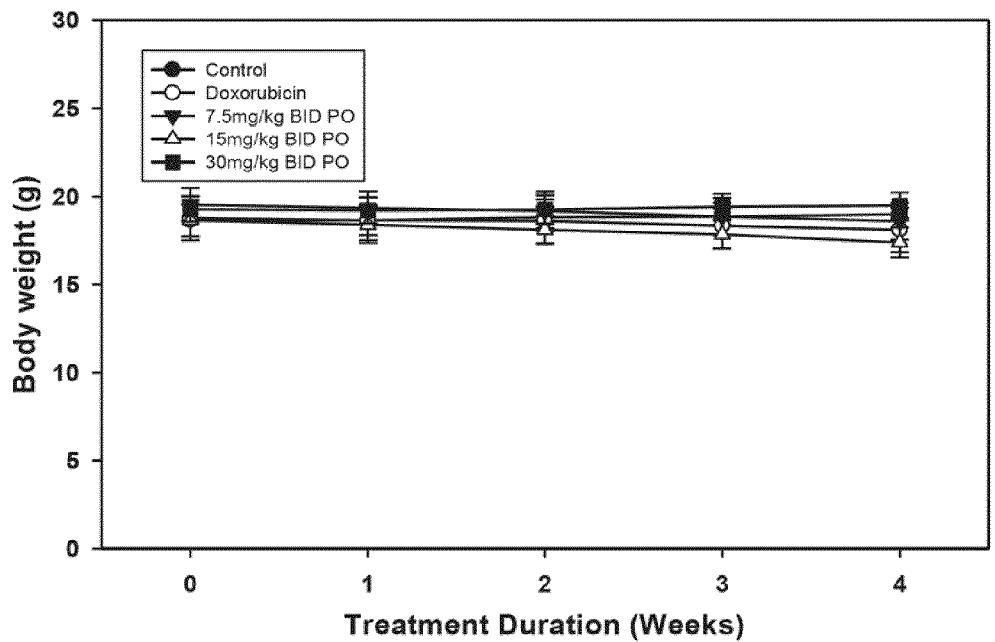
Figure 5A:
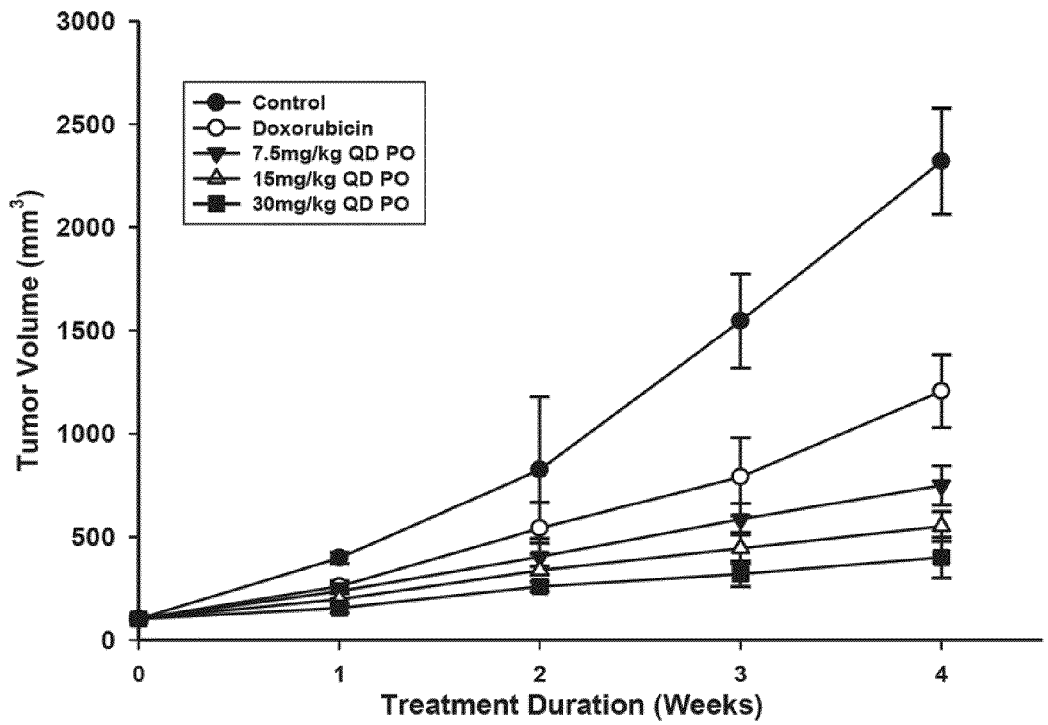
FIGS. 5A-5F show (A) Mean tumor volume-time profiles (B) Mean tumor weight-time profiles (C) Mean body weight-time profiles in Hep3B xenograft nude mice (n=11) following oral dosing of doxonibicin at 5 mg/kg (qd) and 52 at 7.5, 15, and 30 mg/kg (qd) five days per week for four consecutive weeks; (D) Mean tumor volume-time profiles (E) Mean tumor weight-time profiles (F) Mean body weight-time profiles in Hep3B xenograft nude mice (n=11) following intravenous dosing of doxorubicin at 10 mg/kg (qd) and 52 at 7.5, 15, and 30 mg/kg (qd) five days per week for four consecutive weeks.
Figure 5B:
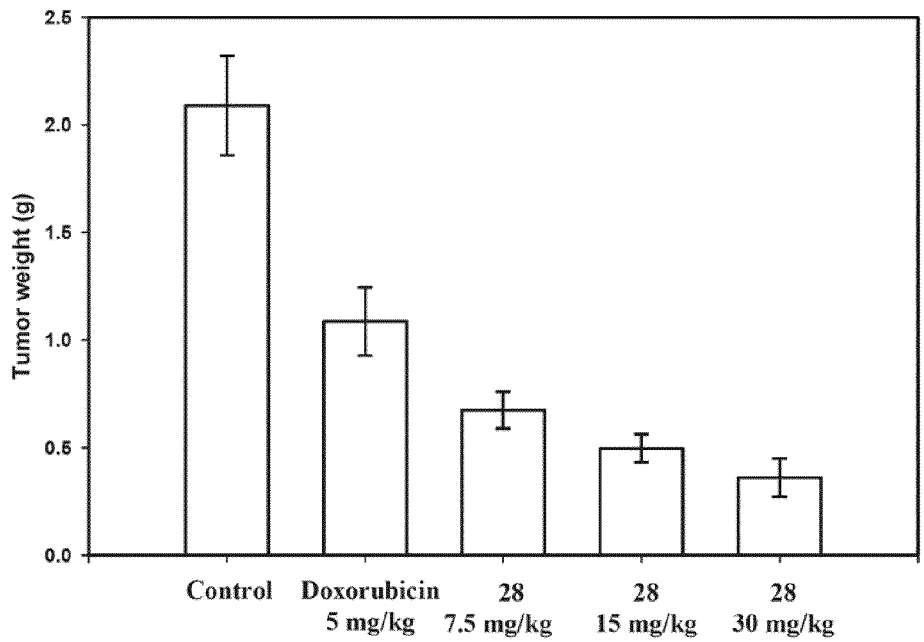
Figure 5C:
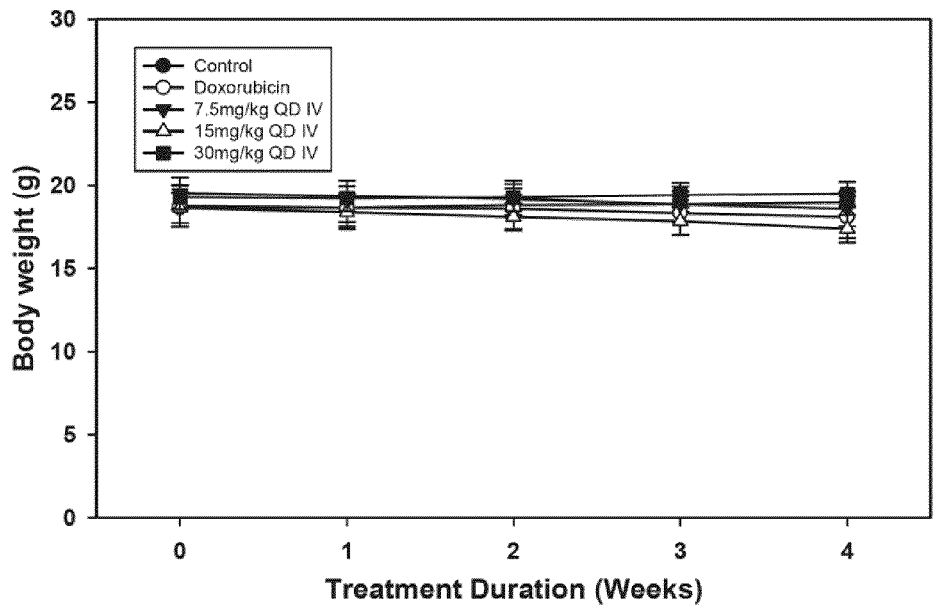
Figure 5D:
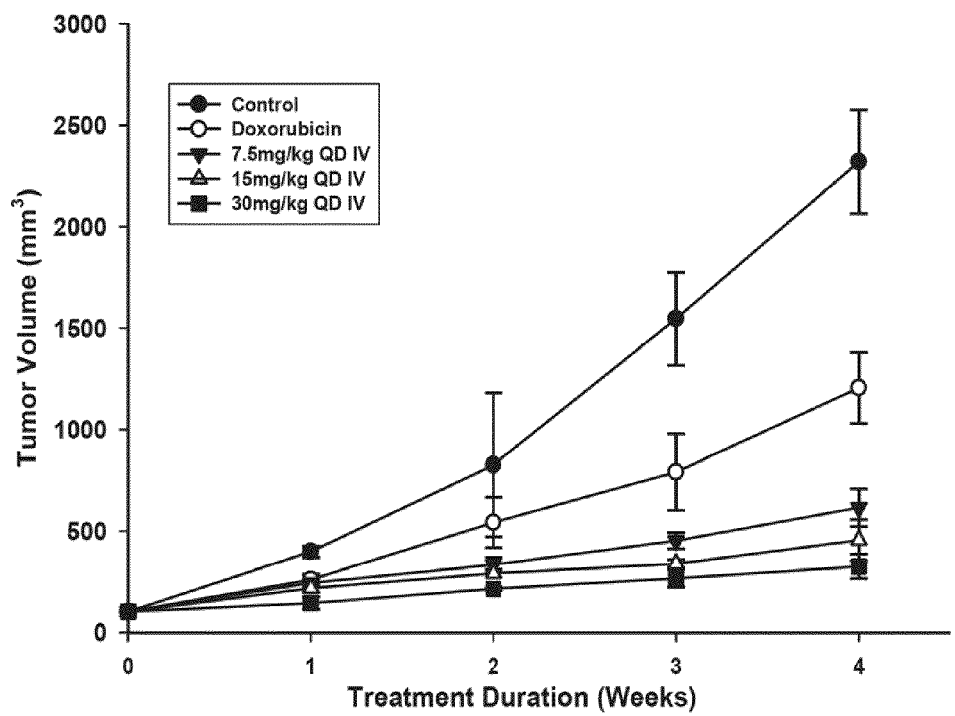
Figure 5E:
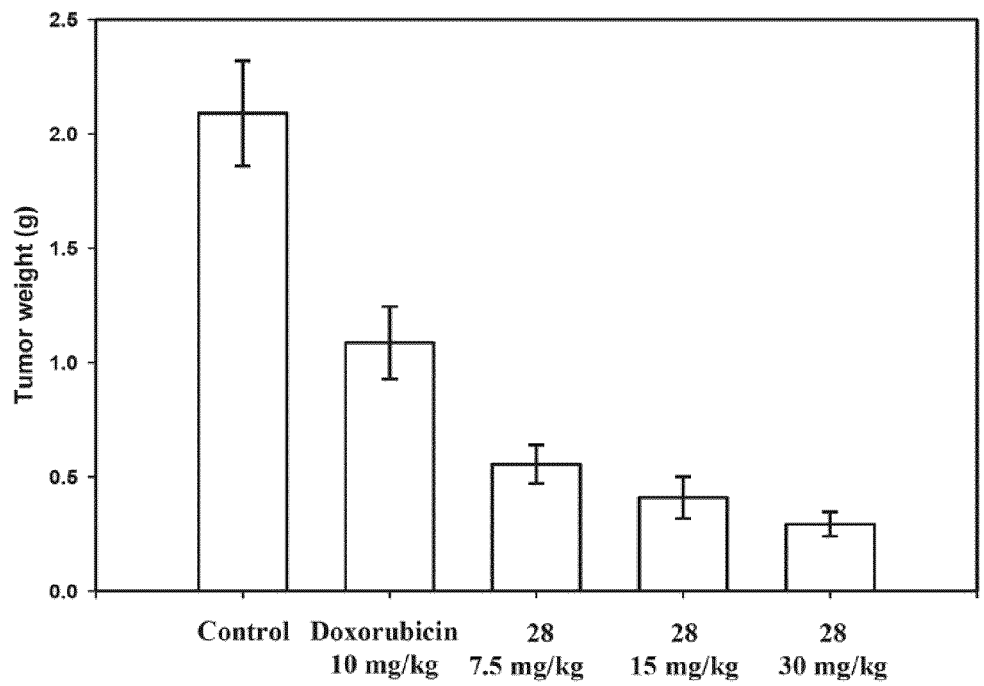
Figure 5F:
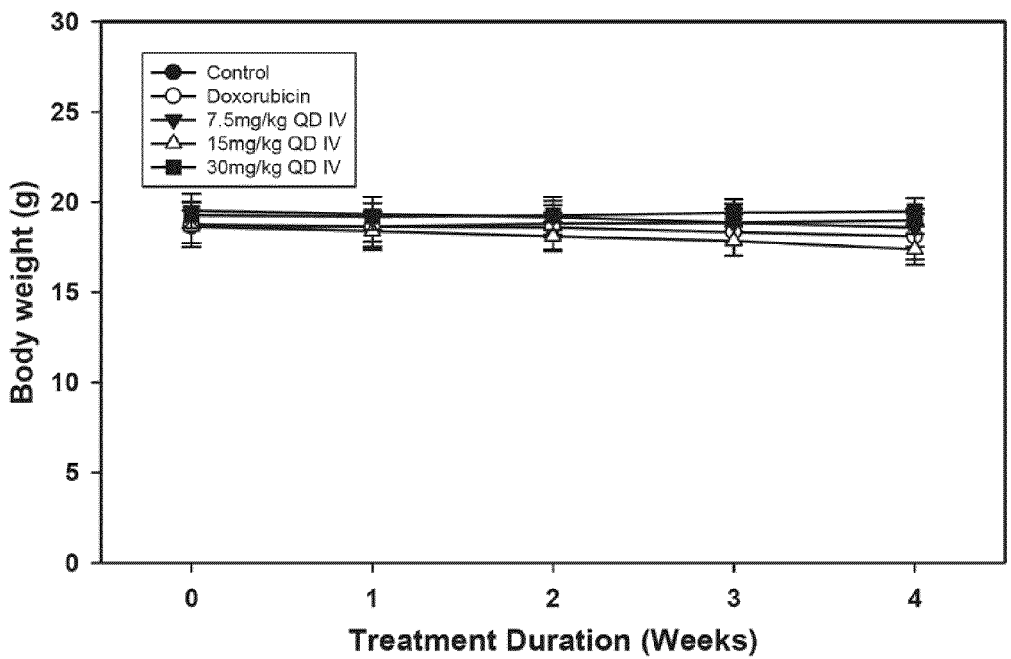

In vivo antitumor activity of compounds 49 and 52. The water soluble diphosphate of 38 49 was evaluated in Hep3B xenograft nude mice model administrated by p.o. and i.v. routes, Results in FIG. 4 (A-F) indicated that the antitumor activity of compound 49 followed dose- and time-dependent manner, and at 7.5 mg/kg (i.v. or p.o., bid) its antitumor activity exceeded that of doxorubicin (5 mg/kg, iv., qd; 10 mg/kg, p.o., qd). During the course of antitumor evaluation, no significant body weight changes were detected either in tested or control mice (FIGS. 4C and 4F). At the same time, the antitumor activity of monophosphate derivative of compound 38 (52) was evaluated with the same animal model by oral route at the dose of 7.5, 15, 30 mg/kg/day FIGS. 5A-5F). As shown by the results in FIG, 5A, compound 52 induced dose- and time-dependent inhibition of Hep3B tumor growth. Significant tumor growth suppression, at an extent exceeding that observed after 10 mg/kg/day oral dosing of doxorubicin, was detected after 7.5 mg/kg/day oral dosing of compound 52. Near complete tumor suppression was observed after 30 mg/kg/day oral dosing.

Again during the course of antitumor evaluation no significant body weight changes were detected in either the tested or the control mice. Similarly, the dose- and time-dependent antitumor test result by i.v. administration, summarized in FIG. 5B, resembled that administrated through p.o. route, and showed slight better antitumor activity in general.

II B Series
Chemical Synthesis

The intermediates, 5-alkylamino-2-aminoacetophenones (60-62) were prepared according to the methods reported before. As shown in Scheme 6, the starting 3-chloroacetophenone (54) was first nitrated with $HNO_3/H_2SO_4$ to form the 5-chloro-2-nitroacetophenone (55) and 5-chloro-4-nitroacetophenone (56). Compound 55 was reacted separately with various alkylamines to yield the corresponding 5-alkylamino-2-nitroacetophenones (57-59). Catalytic hydrogenation of compounds 57-59 yielded the corresponding 5-alkylamino-2-aminoacetophenones (60-62). L. Ll, K. K. Wang, S. C. Kuo, T. S. Wu, D. Lednicer, C. M. Lin, E. Hamel and K. H. Lee, J. Med. Chem., 37, 1126-35. (1994), which is herein incorporated by reference in its entirety.

The synthesis of other intermediated, substituted benzoyl chlorides (83-91) is illustrated in Scheme 7 and Scheme 8. Esterification of substituted benzoic acids (63-67) yielded the corresponding ester (68-72). Compounds 68-71 were treated with benzyl bromide to yield the corresponding benzyloxy derivatives (73-76). On the other hand, compound 72 was treated with diiodomethane to afford ethyl 5,6-methylenedioxobenzoate (77). When compounds 73-77 were hydrolyzed with NaOH to yield the corresponding acids (78-82) which were allowed to react with SOCl$_2$ to afford the corresponding acid chlorides (83-87).

Finally, as shown in Scheme 8, 5-alkylamino-2-aminoacetophenones (60-62) were reacted separately with substituted benzoyl chlorides (83-91) to yield the corresponding amides (92-112), which were subsequently cyclized in dioxane in the presence of NaOH, to afford the target compounds ((113-133).

The compound 138 was derived into a phosphate (147) following the synthetic method in Scheme 10. As illustrated, compound 138 was first reacted with tetrabenzylpyrophosphate 46 in THF, in the presence of NaH, to give bis(dibenzylphosphate) (145) which, without further purification, was subsequently dissolved in MeOH and stirred at 25° C. to yield a monophosphate (146). The structure of compound 146 was confirmed by the chemical shift of its proton on the 3-position (δ 6.39) in the $^1$H-NMR spectrum. Subsequently, compound 146 was debenzylated catalytically to afford a stable monophosphoric acid (147).

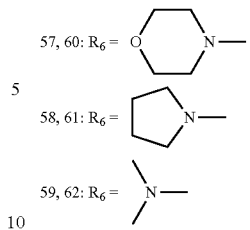

57, 60: R$_6$ =
58, 61: R$_6$ =
59, 62: R$_6$ =

Scheme 6

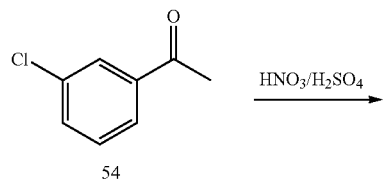

54

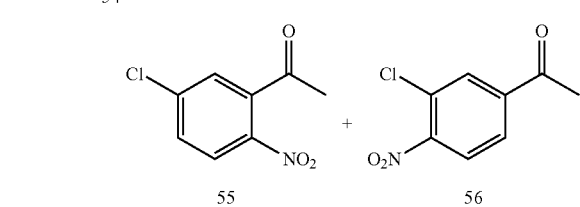

55     56

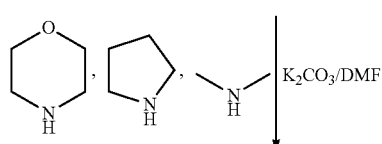

K$_2$CO$_3$/DMF

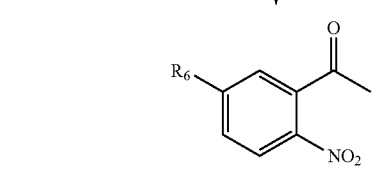

57-59

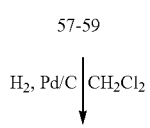

H$_2$, Pd/C | CH$_2$Cl$_2$

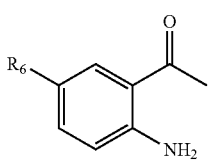

60-62

Scheme 7

A
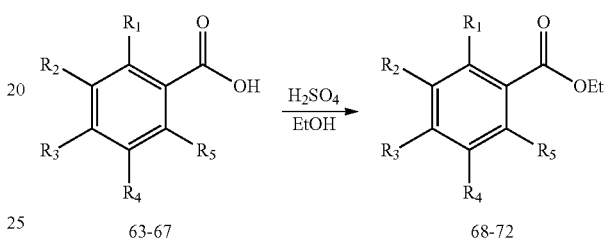

63-67     68-72

B
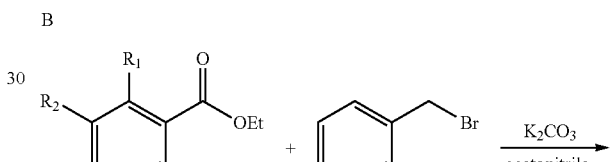

68-71

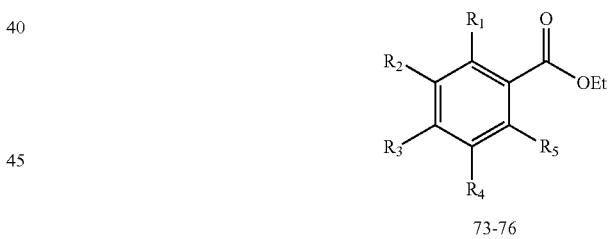

73-76

C
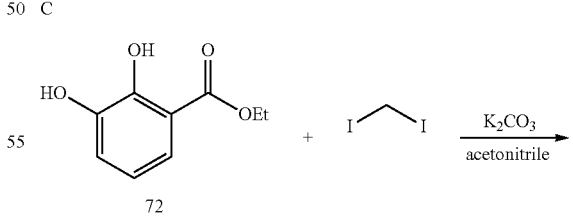

72

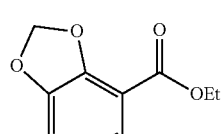

77

-continued

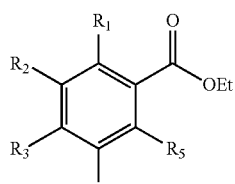
73-77

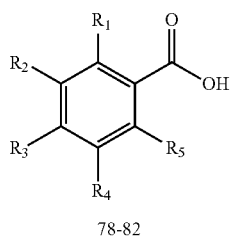
78-82

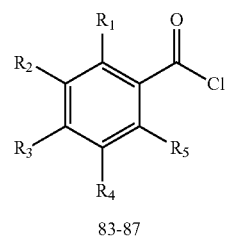
83-87

63, 68: R₁ = OH; R₂, R₃, R₄, R₅ = H
64, 69: R₂ = OH; R₁, R₃, R₄, R₅ = H
65, 70: R₃ = OH; R₁, R₂, R₄, R₅ = H
66, 71: R₂ = OCH₃; R₃ = OH; R₁, R₄, R₅ = H
67, 72: R₁, R₂ = OH; R₃, R₄, R₅ = H
73, 78, 83: R₁ = OBn; R₂, R₃, R₄, R₅ = H
74, 79, 84: R₂ = OBn; R₁, R₃, R₄, R₅ = H
75, 80, 85: R₃ = OBn; R₁, R₂, R₄, R₅ = H
76, 81, 86: R₂ = OCH₃; R₃ = OBn; R₁, R₄, R₅ = H
77, 82, 87: R₁, R₂ = OCH₂O; R₃, R₄, R₅ = H

Scheme 8

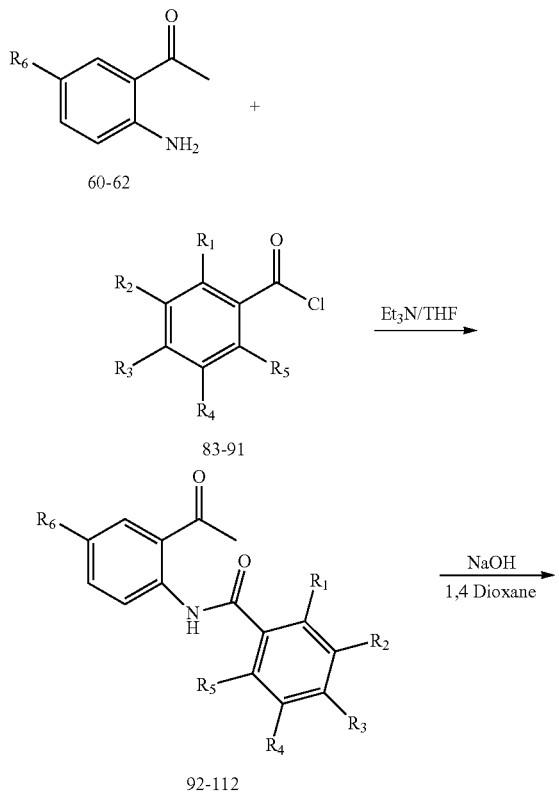

-continued

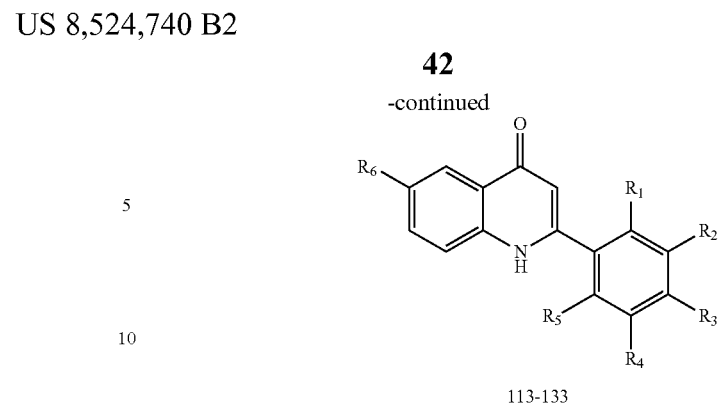
113-133

83, 92-94, 113-115: R₁ = OBn; R₂, R₃, R₄, R₅ = H
84, 95-97, 116-118: R₂ = OBn; R₁, R₃, R₄, R₅ = H
85, 98-100, 119-121: R₃ = OBn; R₁, R₂, R₄, R₅ = H
86, 101, 102, 122, 123: R₂ = OCH₃; R₃ = OBn; R₁, R₄, R₅ = H
87, 103, 104, 124, 125: R₁, R₂ = OCH₂O; R₃, R₄, R₅ = H
88, 105, 106, 126, 127: R₁, R₂ = OCH₃; R₃, R₄, R₅ = H
89, 107, 108, 128, 129: R₁, R₄ = OCH₃; R₂, R₃, R₅ = H
90, 109, 110, 130, 131: R₁ = OCH₃; R₂, R₃, R₄, R₅ = H
91, 111, 112, 132, 133: R₃ = OCH₃; R₁, R₂, R₄, R₅ = H

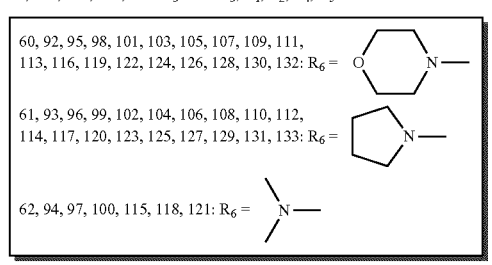

Scheme 9

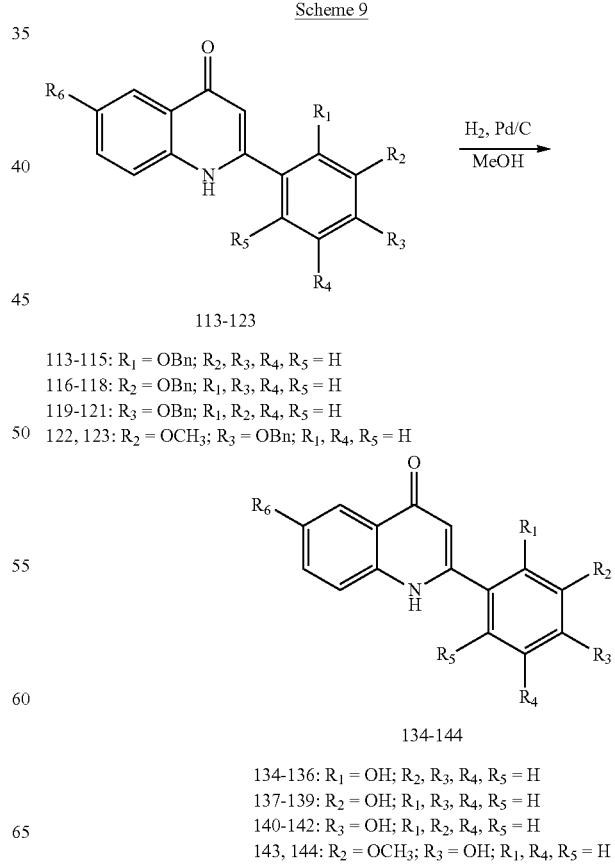
113-123

113-115: R₁ = OBn; R₂, R₃, R₄, R₅ = H
116-118: R₂ = OBn; R₁, R₃, R₄, R₅ = H
119-121: R₃ = OBn; R₁, R₂, R₄, R₅ = H
122, 123: R₂ = OCH₃; R₃ = OBn; R₁, R₄, R₅ = H 134-144

134-136: R₁ = OH; R₂, R₃, R₄, R₅ = H
137-139: R₂ = OH; R₁, R₃, R₄, R₅ = H
140-142: R₃ = OH; R₁, R₂, R₄, R₅ = H
143, 144: R₂ = OCH₃; R₃ = OH; R₁, R₄, R₅ = H

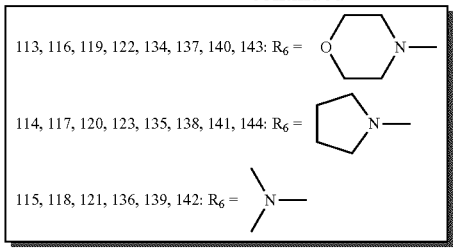

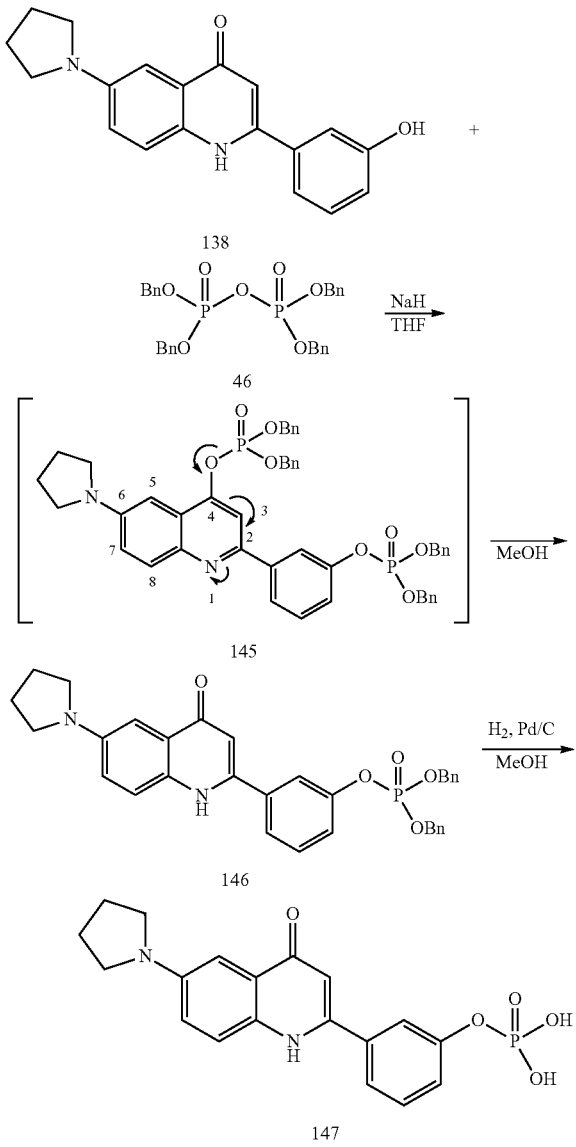

Scheme 10

EXAMPLES

General Experimental Procedures. All of the solvents and reagents were obtained commercially and used without further purification. The progress of all reactions was monitored by TLC on 2×6 cm pre-coated silica gel 60 $F_{254}$ plates of thickness 0.25 mm (Merck). The chromatograms were visualized under UV 254-366 nm. The following adsorbent was used for column chromatography: silica gel 60 (Merck, particle size 0.040-0.063 mm). Melting points were determined with a Yanaco MP-500D melting point apparatus and are uncorrected. IR spectra were recorded on Shimadzu IR-Prestige-21 spectrophotometers as KBr pellets. NMR spectra were obtained on a Bruker Avance DPX-200 FT-NMR spectrometer in $CDCl_3$ or DMSO. The following abbreviations are used: s, singlet; d, doublet; t, triplet; q, quartet; dd, double doublet; and m, multiplet. MS spectra were measured with an HP 5995 GC-MS instrument. Elemental analyses (C, H, and N) were carried out at the instruments center of National Chung Hsing University, Taichung, Taiwan and performed on a Perkin-Elmer 2400 Series II CHNS/O analyzer or Elementar vario EL III Heraeus CHNOS Rapid F002 and the results were within ±0.4% of the calculated values.

5-Chloro-2-nitroacetophenone (55). 65% $HNO_3$ (80 ml) was stirred at −5° C.±1° C. and 98% $H_2SO_4$ (10 mix 10) was added dropwise. To the stirring solution of $HNO_3/H_2SO_4$ was added 3-chloroacetophenone (54) (12.0 g, 77.6 mmol). The mixture was stirred at −5□±1□ for 3 h and poured into crushed ice, and extracted with $CH_2Cl_2$. The extract was dried over $MgSO_4$ and evaporated. The crude product was purified by column chromatography (silica gel, n-hexane/EtOAc=15:1) to give 55 as yellow solid (9.3 g, 46.6 mmol). Yield: 55.8%; mp 47-49° C.; $^1$H-NMR ($CDCl_3$, 200 MHz): δ 2.48 (s, 3H), 7.32 (d, J=2.4 Hz, 1H), 7.49 (dd, J=8.8, 2.2 Hz, 1H), 8.00 (d, J=8.8 Hz, 1H); $^{13}$C-NMR ($CDCl_3$, 50 MHz) δ: 198.27, 143.78, 141.05, 139.44, 130.55, 127.36, 125.91, 30.06; Anal. Calcd for $C_8H_6ClNO_3$: C, 48.14; H, 3.03; N, 7.02.

5-Morpholino-2-nitroacetophenone (57). To a solution of 55 (3.0 g, 15.0 mmol) in DMF (25 ml) were added $K_2CO_3$ (8.3 g, 60.1 mmol) and morpholine (3.2 g, 37.5 mmol). The mixture was refluxed for 3 h and then poured into crushed ice. The precipitate was collected and washed with $H_2O$. The crude product was purified by column chromatography (silica gel, $CH_2Cl_2$: n-hexane=2:1) to give 57 as yellow solid (3.4 g, 13.6 mmol). Yield: 90.4%; mp 124-126° C.; $^1$H-NMR ($CDCl_3$, 200 MHz): δ 2.45 (s, 3H), 3.33-3.38 (m, 4H), 3.78-3.82 (m, 4H), 6.53 (d, J=2.8 Hz, 1H), 6.78 (dd, J=9.4, 2.8 Hz, 1H), 8.02 (d, J=9.4 Hz, 1H); $^{13}$C-NMR ($CDCl_3$, 50 MHz) δ: 201.30, 154.60, 141.53, 134.90, 127.04, 112.88, 109.83, 66.20, 46.84, 30.52; Anal. Calcd for $C_{12}H_{14}N_2O_4$: C, 57.59; H, 5.64; N, 11.19.

5-Pyrrolidino-2-nitroacetophenone (58) was obtained from 30 and pyrrolidine, using the same synthetic procedure as for 57 to give 58 as yellow solid (3.2 g, 13.7 mmol); yield 90.9%; mp 119-121° C.; $^1$H-NMR ($CDCl_3$, 200 MHz): δ 2.04 (m, 4H), 2.45 (s, 3H), 3.37 (m, 4H), 6.19 (d, J=2.6 Hz, 1H), 6.44 (dd, J=9.4, 2.6 Hz, 1H), 8.02 (d, J=9.4 Hz, 1H); $^{13}$C-NMR ($CDCl_3$, 200 MHz) δ: 201.80, 151.61, 142.16, 132.54, 127.37, 111.08, 107.87, 48.07, 30.58, 25.37; Anal. Calcd for $C_{12}H_{14}N_2O_3$: C, 61.53; H, 6.02; N, 11.96.

5-Dimethylamino-2-nitroacetophenone (59) was obtained from 30 and dimethylamine hydrochloride, using the same synthetic procedure as for 57 to give 59 as yellow solid (2.3 g, 11.0 mmol); yield 88.2%; mp 125-127° C.; $^1$H-NMR ($CDCl_3$, 200 MHz): δ 2.45 (s, 3H), 3.08 (s, 6H), 6.31 (d, J=2.8 Hz, 1H), 6.58 (dd, J=9.4, 2.8 Hz, 1H), 8.02 (d, J=9.4 Hz, 1H); $^{13}$C-NMR ($CDCl_3$, 50 MHz) δ: 201.76, 153.98, 141.88, 133.02, 127.19, 110.83, 107.66, 40.30, 30.56

5-Morpholino-2-aminoacetophenone (60). A solution of 57 (1.5 g, 5.9 mmol) in $CH_2Cl_2$ (30 ml) was hydrogenated in the presence of 10% Pd/C (0.4 g) at 25° C. for 8 h. The catalyst was filtered off and the filtrate was evaporated to give 60 as yellow solid. (1.25 g, 5.68 mmol); yield 94.6%; $^1$H-NMR (CDCl₃, 200 MHz): δδ 2.45 (s, 3H), 2.9 (m, 4H), 3.68 (m, 4H), 6.67 (d, J=8.8 Hz, 1H), 6.78 (br, 2H), 7.02-7.11 (m, 2H); ¹³C-NMR (CDCl₃, 50 MHz) δ: 200.44, 145.61, 141.51, 126.37, 119.26, 118.40, 118.22, 66.96, 51.57, 27.93; Anal. Calcd for $C_{12}H_{16}N_2O_2$: C, 65.43; H, 7.32; N, 12.72.

5-Pyrrolidino-2-aminoacetophenone (61) was obtained from 58, using the same synthetic procedure as for 60 to give 61 as orange solid (1.2 g, 5.9 mmol); yield 91.8%; ¹H-NMR (CDCl₃-d₆, 200 MHz): δ 1.86 (m, 4H), 2.45 (s, 3H), 3.10 (m, 4H), 6.42 (br, 2H), 6.62-6.77 (m, 3H); ¹³C-NMR (CDCl₃, 50 MHz) δ: 200.56, 143.11, 139.23, 121.91, 118.59, 117.86, 113.03, 48.57, 28.47, 25.9; Anal. Calcd for $C_{12}H_{16}N_2O$: C, 70.56; H, 7.90; N, 13.71.

5-Dimethylamino-2-aminoacetophenone (62) was obtained from 59, using the same synthetic procedure as for 60 to give 62 as orange solid (1.8 g, 10.1 mmol); yield 91.5%; ¹H-NMR (DMSO-d₆, 200 MHz): δ 2.45 (s, 3H), 2.71 (s, 6H), 6.64-6.69 (m, 2H), 6.96-7.00 (m, 3H); ¹³C-NMR (DMSO-d₆, 50 MHz) δ: 200.49, 144.66, 141.42, 124.49, 118.46, 117.37, 115.79, 42.34, 28.42

Ethyl 2-hydroxybenzoate (68). To a solution of 2-hydroxybenzoic acid (63) (5.0 g, 36.2 mmol) in anhydrous EtOH (150 ml) was added 98% H₂SO₄ (4 ml). The mixture was refluxed for 4 h and concentrated. The residue was extracted with CH₂Cl₂ dried over MgSO₄ and evaporated. The crude was purified by distillation to give 68 as colorless liquid. (5.85 g, 35.21 mmol). Yield: 97.25%; MS (EI, 70 eV): m/z 166.2 (M⁺); ¹H-NMR (CDCl₃, 200 MHz): δ 1.39 (t, J=7.2 Hz, 3H), 4.37 (q, J=7.2, 7.0 Hz, 2H), 6.81 (t, J=6.6 Hz, 1H), 6.89 (d, J=8.0 Hz, 1H), 7.42 (t, J=7.2 Hz, 1H), 7.82 (dd, J₁=8.0, 1.8 Hz, 1H), 10.83 (s, 1H); ¹³C-NMR (CDCl₃, 50 MHz) δ: 170.20, 161.64, 135.56, 129.89, 119.06, 117.53, 61.40, 14.18; Anal. Calcd for $C_9H_{10}O_3$: C, 65.05; H, 6.07.

Ethyl 3-hydroxybenzoate (69) was obtained from 64, using the same synthetic procedure as for 38 to give 39 as white solid. (3.4 g, 20.5 mmol); yield 94.2%; mp 60-62° C.; MS (EI, 70 eV): m/z 166.2 (M⁺); ¹H-NMR (CDCl₃, 200 MHz): δ 1.36 (t, J=7.2 Hz, 3H), 4.35 (q, J=7.2, 7.0 Hz, 2H), 5.55 (s, 1H), 7.07 (dd, J=2.6, 1.2 Hz, 1H), 7.27 (d, J=7.8 Hz, 1H), 7.55-7.62 (m, 2H); ¹³C-NMR (CDCl₃, 50 MHz) δ: 167.15, 156.07, 131.50, 129.69, 121.36, 120.36, 116.36, 61.43, 14.23; Anal. Calcd for $C_9H_{10}O_3$: C, 65.05; H, 6.07.

Ethyl 4-hydroxybenzoate (70) was obtained from 65, using the same synthetic procedure as for 68 to give 70 as white solid. (5.3 g, 31.9 mmol); yield 88.2%; mp 105-107° C.; MS (EI, 70 eV): m/z 166.2 (M⁺); ¹H-NMR (CDCl₃, 200 MHz): δ 1.36 (t, J=7.2 Hz, 3H), 4.33 (q, J=7.2, 7.0 Hz, 2H), 6.84 (d, J=1.8 Hz, 1H), 6.88 (d, J=1.8 Hz, 1H), 7.90 (d, J=1.8 Hz, 1H), 7.95 (d, J=1.8 Hz, 1H); ¹³C-NMR (CDCl₃, 50 MHz) δ: 167.13, 160.38, 131.91, 122.44, 115.26, 61.01, 14.30; Anal. Calcd for $C_9H_{10}O_3$: C, 65.05; H, 6.07.

Ethyl 3-methoxy-4-hydroxybenzoate (71) was obtained from 66, using the same synthetic procedure as for 68 to give 71 as brown liquid. (6.3 g, 32.1 mmol); yield 90.9%; MS (EI, 70 eV): m/z 196.2 (M⁺); ¹H-NMR (CDCl₃, 200 MHz): δ 1.35 (t, J=7.2 Hz, 3H), 3.93 (s, 3H), 4.32 (q, J=7.2, 7.0 Hz, 2H), 6.90 (d, J=8.2 Hz, 1H), 7.53 (d, J=1.8 Hz, 1H), 7.62 (dd, J=8.2, 1.8 Hz, 1H); ¹³C-NMR (CDCl₃, 50 MHz) δ: 166.44, 149.91, 146.13, 124.10, 122.62, 113.99, 111.70, 60.79, 56.09, 14.37; Anal. Calcd for $C_{10}H_{12}O_4$: C, 61.22; H, 6.16.

Ethyl 2,3-dihydroxybenzoate (72) was obtained from 67, using the same synthetic procedure as for 68 to give 72 as white solid. (5.4 g, 29.6 mmol); yield 91.4%; mp 92-94° C.; MS (EI, 70 eV): m/z 182.2 (M⁺); ¹H-NMR (CDCl₃, 200 MHz): δ 1.40 (t, J=7.2 Hz, 3H), 4.38 (q, J=7.2, 7.0 Hz, 2H), 5.18 (br, 1H), 6.70-7.40 (m, 3H), 10.97 (br, 1H); ¹³C-NMR (CDCl₃, 50 MHz) δ: 170.38, 148.90, 145.00, 120.55, 119.71, 119.45, 119.10, 112.63, 61.61, 14.13; Anal. Calcd for $C_{10}H_{12}O_4$: C, 59.34; H, 5.53.

Ethyl 2-(benzyloxy)benzoate (73). To a solution of 68 (5.8 g, 34.9 mmol) in CH₃CN (150 ml) was added K₂CO₃ (10.6 g, 76.8 mmol). The mixture was added benzyl bromide (6.57 g, 38.39 mmol) and refluxed for 8 h under N₂ atmosphere. The reaction mixture was cooled to 25° and poured into H₂O (500 ml), and then extracted with CH₂Cl₂. The organic layer was washed with H₂O, dried over MgSO₄ and evaporated. The crude products were purified by distillation to give 73 as colorless liquid. (8.5 g, 33.2 mmol). Yield: 94.71%; MS (EI, 70 eV): m/z 256.3 (M⁺); ¹H-NMR (CDCl₃, 200 MHz): δ 1.33=(t, J=7.2 Hz, 3H), 4.35 (q, =7.2, 7.0 Hz, 2H), 5.15 (s, 2H), 7.00 (d, =8.0 Hz, 2H), 7.32-7.45 (m, 5H), 7.49 (d, J=8.2 Hz, 1H), 7.82 (dd, J=8.2, 1.8 Hz, 1H); ¹³C-NMR (CDCl₃, 50 MHz) δ: 166.60, 158.01, 136.77, 133.25, 131.69, 128.49, 127.80, 126.99, 121.20, 120.56, 113.75, 70.57, 60.93, 14.29; Anal. Calcd for $C_{16}H_{16}O_3$: C, 74.98; H, 6.29.

Ethyl 3-(benzyloxy)benzoate (74) was obtained from 69, using the same synthetic procedure as for 73 to give 74 as colorless liquid. (4.05 g, 15.80 mmol); yield 77.3%; MS (EI, 70 eV): m/z 256.3 (M⁺); ¹H-NMR (CDCl₃, 200 MHz): δ 1.39 (t, J=7.2 Hz, 3H), 4.37 (q, 7.2, 7.0 Hz, 2H), 5.08 (s, 2H), 7.17-7.72 (m, 9H); ¹³C-NMR (CDCl₃, 200 MHz) δ: 166.42, 158.76, 136.66, 131.90, 129.48, 128.67, 128.14, 127.62, 122.24, 119.96, 115.26, 70.14, 61.09, 14.38; Anal. Calcd for $C_{16}H_{16}O_3$: C, 74.98; H, 6.29.

Ethyl 4-(benzyloxy)benzoate (75) was obtained from 70, using the same synthetic procedure as for 73 to give 75 as colorless liquid. (7.6 g, 29.6 mmol); yield 92.5%; MS (EI, 70 eV): m/z 256.3 (M⁺); ¹H-NMR (CDCl₃, 200 MHz): δ 1.35 (t, J=7.2 Hz, 3H), 4.32 (q, J=7.2, 7.0 Hz, 2H), 5.09 (s, 2H), 6.95 (d, J=2.0 Hz, 1H), 6.98 (d, J=2.0 Hz, 1H), 7.31-7.41 (m, 5H), 7.95 (d, J=2.0 Hz, 1H), 7.99 (d, J=2.0 Hz, 1H); ¹³C-NMR (CDCl₃, 50 MHz) δ: 166.36, 162.39, 136.28, 131.55, 129.02, 128.67, 128.19, 127.48, 123.18, 114.41, 70.08, 60.65, 14.37; Anal. Calcd for $C_{16}H_{16}O_3$: C, 74.98; H, 6.29.

Ethyl 4-(benzyloxy)-3-methoxybenzoate (76) was obtained from 71, using the same synthetic procedure as for 73 to give 76 as brown solid. (8.5 g, 29.7 mmol); yield 91.5%; mp 73-75° C.; MS (EI, 70 eV): 286.4 (NC); ¹H-NMR (CDCl₃, 200 MHz): δδ 1.35 (t, J=7.2 Hz, 3H), 3.91 (s, 3H), 4.32 (q, J17.2, 7.0 Hz, 2H), 5.18 (s, 2H), 6.85 (d, J=8.4 Hz, 1H), 7.27-7.62 (m, 7H); ¹³C-NMR (CDCl₃, 50 MHz) δ: 166.38, 152.01, 149.12, 136.40, 128.64, 128.05, 127.22, 123.29, 112.46, 70.77, 60.79, 56.07, 14.39; Anal. Calcd for $C_{17}H_{18}O_4$: C, 71.31; H, 6.34.

Ethyl 2,3-methylenedioxybenzoate (77) was obtained from 72 and diiodomethane, using the same synthetic procedure as for 73 to give 77 as colorless liquid. (2.8 g, 14.4 mmol); yield 87.6%; mp 90-92° C.; MS (EI, 70 eV): ml: 194.1 (M⁺); ¹H-NMR (CDCl₃, 200 MHz): δ 1.35 (t, J=7.2 Hz, 3H), 4.34 (q, J=7.2, 7.0 Hz, 2H), 6.04 (s, 2H), 6.80 (t, J=7.8 Hz, 3H), 6.92 (dd, J=7.8, 1.4 Hz, 1H), 7.37 (dd, J=7.8, 1.4 Hz, 1H); ¹³C-NMR (CDCl₃, 50 MHz) δ: 164.42, 148.68, 148.41, 122.66, 121.10, 113.28, 112.12, 101.83, 60.98, 14.30; Anal. Calcd for $C_{10}H_{10}O_4$: C, 61.85; H, 5.19.

2-(Benzyloxy)benzoic acid (78). To a suspension of 73 (4.0 g, 15.6 mmol) in H₂O (150 ml) were added NaOH (3.1 g, 78.0 mmol) and EtOH (5 ml). The mixture was reflux for 12 h, and cooled to 25° C. The solid was filtered out and the filtrate was acidified with 2N HCl. The precipitate was collected and washed with H₂O. The crude product was recrystallized from to give 78 as white solid. (3.0 g, 13.2 mmol). Yield: 84.6%; mp 73-75° C.; MS (EI, 70 eV): m/z 228.3 (M⁺); ¹H-NMR (CDCl₃, 200 MHz): δ 5.27 (s, 2H), 7.08-7.54 (m, 8H), 6.93

(dd, J=8.0, 1.8 Hz, 1H); $^{13}$C-NMR (CDCl$_3$, 50 MHz) δ: 165.43, 157.40, 135.02, 134.34, 133.88, 129.16, 127.92, 122.44, 118.09, 113.11, 72.23; Anal. Calcd for C$_{14}$H$_{12}$O$_3$: C, 73.67; H, 5.30.

3-(Benzyloxy)benzoic acid (79) was obtained from 74, using the same synthetic procedure as for 48 to give 49 as white solid. (3.1 g, 13.6 mmol). Yield: 87.4%; mp 120-122° C.; MS (EI, 70 eV): m/z 228.3 (M$^+$); $^1$H-NMR (DMSO-d$_6$, 200 MHz): δ 3.37 (br, 1H), 5.12 (s, 2H), 7.19-7.50 (m, 9H); $^{13}$C-NMR (DMSO-d$_6$, 50 MHz) δ: 167.55, 18.77, 137.26, 132.69, 130.19, 128.90, 128.33, 128.10, 122.25, 120.15, 115.36; Anal. Calcd for C$_{14}$H$_2$O$_3$: C, 73.67; H, 5.30.

4-(Benzyloxy)benzoic acid (80) was obtained from 75, using the same synthetic procedure as for 78 to give 80 as white solid. (6.2 g, 27.2 mmol). Yield: 92.0%; mp 195-197° C.; MS (EI, 70 eV): m/z 228.3 (M$^+$); $^1$H-NMR (DMSO-d$_6$, 200 MHz): δ 5.10 (s, 2H), 6.96 (d, J=2.0 Hz, 1H), 7.00 (d, J=2.0 Hz, 1H), 7.28-7.44 (m, 5H), 7.82 (d, J=2.0 Hz, 1H), 7.86 (d, J=2.0 Hz, 1H); $^{13}$C-NMR (DMSO-d$_6$, 50 MHz) δ: 168.50, 161.37, 137.20, 131.53, 128.91, 128.37, 128.21, 127.00, 114.55, 69.78; Anal. Calcd for C$_{14}$H$_{12}$O$_3$: C, 73.67; H, 5.30.

4-(Benzyloxy)-3-methoxybenzoic acid (81) was obtained from 76, using the same synthetic procedure as for 78 to give 81 as white solid. (7.6 g, 29.4 mmol). Yield: 99.5%; mp 159-162° C.; MS (EI, 70 eV): m/z 258.3 (M$^+$); $^1$H-NMR (DMSO-d$_6$, 200 MHz): δ 3.76 (s, 3H), 5.11 (s, 2H), 7.10 (d, J=8.4 Hz, 1H), 7.29-7.43 (m, 6H), 7.50 (dd, J=8.4, 1.8 Hz, 1H); $^{13}$C-NMR (DMSO-d$_6$, 50 MHz) δ: 167.53, 152.03, 149.01, 136.99, 128.92, 128.38, 123.68, 123.47, 112.86, 112.58, 70.30, 55.94; Anal. Calcd for C$_{15}$H$_{14}$O$_4$: C, 69.76; H, 5.46.

2,3-Methylenedioxybenzoic acid (82) was obtained from 77, using the same synthetic procedure as for 78 to give 82 as white solid. (2.3 g, 13.8 mmol). Yield: 96.0%; mp 188-190° C.; MS (EI, 70 eV): m/z 166.2 (M$^+$); $^1$H-NMR (DMSO-d$_6$, 200 MHz): δ 6.07 (s, 2H), 7.05 (d, J=8.2 Hz, 1H), 7.25 (t, J=7.6 Hz, 1H), 7.06 (dd, J=7.6, 1.2 Hz, 1H), 7.23 (dd, J=7.6, 1.2 Hz, 1H), 12.95 (br, 1H); $^{13}$C-NMR (DMSO-d$_6$, 50 MHz) δ: 165.56, 148.91, 148.51, 122.94, 121.58, 113.80, 112.46, 102.11; Anal. Calcd for C$_8$H$_6$O$_4$: C, 57.84; H, 3.64.

2-Benzyloxybenzoyl chloride (83). To a suspension of 78 (3.1 g, 13.6 mmol) in dry toluene (150 ml) was added SOCl$_2$ (12.9 g, 109.1 mmol). The mixture was reflux for 8 h and evaporated to give 83 as yellow liquid to use directly in the next step. (2.55 g, 10.3 mmol). Yield: 79.07%.

3-Benzyloxybenzoyl chloride (84) was obtained from 79, using the same synthetic procedure as for 53 to give 54 as yellow liquid to use directly in the next step. (2.5 g, 10.1 mmol). Yield: 74.2%.

4-Benzyloxybenzoyl chloride (85) was obtained from 80, using the same synthetic procedure as for 53 to give 55 as yellow liquid to use directly in the next step. (2.4 g, 9.7 mmol). Yield: 79.5%.

4-Benzyloxy-3-methoxybenzoyl chloride (86) was obtained from 81, using the same synthetic procedure as for 83 to give 86 as brown liquid to use directly in the next step. (4.5 g, 16.3 mmol). Yield: 84.6%.

2,3-Methylenedioxybenzoyl chloride (87) was obtained from 82, using the same synthetic procedure as for 83 to give 87 as white solid to use directly in the next step. (1.7 g, 9.2 mmol). Yield: 76.5%.

2,3-Dimethoxybenzoyl chloride (88) was obtained from 83, using the same synthetic procedure as for 53 to give 58 as yellow liquid to use directly in the next step. (2.8 g, 14.0 mmol). Yield: 84.8%.

2,5-Dimethoxybenzoyl chloride (89) was obtained from 84, using the same synthetic procedure as for 55 to give 59 as yellow liquid to use directly in the next step. (2.3 g, 11.5 mmol). Yield: 83.5%.

N-(2-Acetyl-4-morpholinophenyl)-2-benzyloxybenzamide (92). To a solution of 60 (1.3 g, 5.9 mmol) in THF (150 ml) was added Et$_3$N (8 ml). The mixture was stirred at 0° C. and 83 (1.7 g, 7.1 mmol) was added dropwise. The reaction mixture was stirred at 25° C. for 2 h and poured into crushed ice and extracted with CH$_2$Cl$_2$. The extract was washed with H$_2$O, dried over MgSO$_4$ and evaporated. The crude product was purified by column chromatography (silica gel, CH$_2$Cl$_2$) to give 92 as yellow solid. (2.1 g, 4.9 mmol). Yield: 83.3%; mp 144-146° C.; MS (EI, 70 eV): m/z 430.2 (M$^+$); $^1$H-NMR (CDCl$_3$, 200 MHz): δ 2.51 (s, 3H), 3.14 (m, 4H), 3.87 (m, 4H), 5.46 (s, 2H), 6.95-7.05 (m, 2H), 7.15 (dd, J=9.2, 3.0 Hz, 1H), 7.22-7.44 (m, 7H), 8.10 (dd, J=7.6, 1.8 Hz, 1H), 8.37 (d, J=9.2 Hz, 1H), 12.25 (s, 1H); $^{13}$C-NMR (CDCl$_3$, 50 MHz) δ: 201.16, 164.61, 156.37, 136.77, 132.69, 132.11, 128.54, 127.79, 126.98, 125.30, 123.69, 122.22, 121.16, 117.82, 113.28, 70.46, 66.78, 49.94, 28.58; Anal. Calcd for C$_{26}$H$_{26}$N$_2$O$_4$; C, 72.54; H, 6.09; N, 6.51.

N-(2-Acetyl-4-pyrrolidinophenyl)-2-benzyloxybenzamide (93) was obtained from 61 and 83, using the same synthetic procedure as for 92. The crude product was purified by column chromatography (silica gel, CHCl$_3$/n-hexane=10:1) to give 93 as yellow solid. (1.6 g, 3.9 mmol); yield 76.4%; mp 160-161° C.; MS (EI, 70 eV): m/z 414.2 (M$^+$); $^1$H-NMR (CDCl$_3$, 200 MHz): δ 2.02 (m, 4H), 2.51 (s, 3H), 3.30 (m, 4H), 5.45 (s, 2H), 6.85-7.45 (m, 10H), 8.1 (dd, J=7.8, 1.6 Hz, 1H), 8.67 (d, J=9.2 Hz, 1H), 12.07 (s, 1H); $^{13}$C-NMR (CDCl$_3$, 50 MHz) δ: 201.71, 164.15, 156.31, 143.73, 136.68, 132.02, 128.52, 127.74, 12.700, 125.89, 124.04, 121.10, 117.30, 113.25, 112.63, 70.45, 47.89, 28.62, 25.44; Anal. Calcd for C$_{26}$H$_{26}$N$_2$O$_3$; C, 75.34; H, 6.32; N, 6.76.

N-(2-Acetyl-4-dimethylaminophenyl)-2-benzyloxybenzamide (94) was obtained from 62 and 53, using the same synthetic procedure as for 92. The crude product was purified by column chromatography (silica gel, CHCl$_2$) to give 94 as yellow solid. (2.2 g, 5.7 mmol); yield 77.7%; mp 132-134° C.; MS (EI, 70 eV): m/z 388.2 (M$^+$); $^1$H-NMR (CDCl$_3$, 200 MHz): δ 2.51 (s, 3H), 2.95 (s, 6H), 5.46 (s, 2H), 7.00 (dd, J=9.2, 2.6 Hz, 1H), 7.05-7.45 (m, 9H), 8.10 (dd, J=7.8, 1.8 Hz, 1H), 8.71 (d, J=9.2 Hz, 1H), 12.13 (s, 1H); $^{13}$C-NMR (CDCl$_3$, 50 MHz) δ: 201.55, 164.34, 156.34, 146.04, 136.83, 132.49, 132.05, 130.31, 128.53, 127.77, 127.01, 125.03, 123.95, 123.85, 121.12, 118.81, 114.34, 113.28, 70.47, 41.03, 28.59; Anal. Calcd for C$_{24}$H$_{24}$N$_2$O$_3$; C, 74.21; H, 6.23; N, 7.21.

N-(2-Acetyl-4-morpholinophenyl)-3-benzyloxybenzamide (95) was obtained from 60 and 84, using the same synthetic procedure as for 92. The crude product was purified by column chromatography (silica gel, CHCl$_3$/n-hexane=8:1) to give 95 as yellow solid. (1.15 g, 2.67 mmol); yield 84.1%; mp 140-142° C.; MS (EI, 70 eV): m/z 430.2 (M$^+$); $^1$H-NMR (CDCl$_3$, 200 MHz): δ 2.67 (s, 3H), 3.13 (m, 4H), 3.9 (m, 4H), 5.13 (s, 2H), 6.95 (m, 1H), 7.05 (m, 1H), 7.22 (m, 1H), 7.23-7.41 (m, 7H), 8.10 (m, 1H), 8.37 (d, J=9.2 Hz, 1H), 12.35 (s, 1H); $^{13}$C-NMR (CDCl$_3$, 50 MHz) δ: 203.05, 165.46, 159.14, 136.66, 136.48, 134.56, 129.82, 128.60, 128.06, 127.61, 123.38, 122.94, 122.04, 119.47, 119.09, 118.41, 113.44, 70.14, 66.75, 49.87, 28.58; Anal. Calcd for C$_{26}$H$_{26}$N$_2$O$_4$; C, 72.54; H, 6.09; N, 6.51.

N-(2-Acetyl-4-pyrrolidinophenyl)-3-benzyloxybenzamide (96) was obtained from 61 and 84, using the same synthetic procedure as for 92. The crude product was purified by column chromatography (silica gel, CH$_2$Cl$_2$/n-hexane=5:

1) to give 96 as yellow solid. (1.05 g, 2.53 mmol); yield 74.1%; mp 131-133° C.; MS (EI, 70 eV): m/z 414.2 (M$^+$); $^1$H-NMR (CDCl$_3$, 200 MHz): δ 2.02 (m, 4H), 2.67 (s, 3H), 3.30 (m, 4H), 5.14 (s, 2H), 6.83-7.67 (m, 11H), 8.78 (d, J=9.2 Hz, 1H), 12.20 (s, 1H); $^{13}$C-NMR (CDCl$_3$, 50 MHz) δ: 203.51, 165.07, 159.12, 143.54, 136.88, 136.75, 129.71, 128.59, 128.02, 127.62, 123.32, 122.33, 119.41, 118.85, 118.54, 113.34, 110.89, 70.13, 47.99, 28.57, 25.42; Anal. Calcd for C$_{26}$H$_{26}$N$_2$O$_3$; C, 75.34; H, 6.32; N, 6.76.

N-(2-acetyl-4-dimethylaminophenyl)-3-(benzyloxy)benzamide (97) was obtained from 62 and 84, using the same synthetic procedure as for 92. The crude product was purified by column chromatography (silica gel, CH$_2$Cl$_2$) to give 97 as yellow solid. (1.6 g, 4.1 mmol); yield 73.4%; mp 147-149° C.; MS (EI, 70 eV): m/z 388.2 (M$^+$); $^1$H-NMR (CDCl$_3$, 200 MHz): δ 2.66 (s, 3H), 2.94 (s, 6H), 5.14 (s, 2H), 6.83 (d, 6.4 Hz, 1H), 7.13-7.69 (m, 10H), 7.57-7.67 (m, 2H), 8.80 (d, J=9.2 Hz, 1H), 12.26 (s, 1H); $^{13}$C-NMR (CDCl$_3$, 50 MHz) δ: 203.43, 165.18, 159.12, 146.03, 136.74, 131.68, 129.75, 128.60, 128.04, 127.63, 123.11, 122.11, 119.78, 119.43, 118.90, 114.71, 113.38, 70.12, 40.88, 28.57; Anal. Calcd for C$_{24}$H$_{24}$N$_2$O$_3$; C, 74.21; H, 6.23; N, 7.21.

N-(2-Acetyl-4-morpholinophenyl)-4-benzyloxybenzamide (98) was obtained from 60 and 85, using the same synthetic procedure as for 92. The crude product was purified by column chromatography (silica gel, EtOAc/CH$_2$Cl$_2$=1:2) to give 98 as yellow solid. (1.5 g, 3.5 mmol); yield 64.0%; mp 172-175° C.; MS (EI, 70 eV): m/z 430.2 (M$^+$); $^1$H-NMR (CDCl$_3$, 200 MHz): δ 2.67 (s, 3H), 3.14 (m, 4H), 3.88 (m, 4H), 5.05 (s, 2H), 6.99-7.43 (m, 9H), 7.97 (d, J=2.0 Hz, 1H), 8.00 (d, J=2.0 Hz, 1H), 8.86 (d, J=9.2 Hz, 1H), 12.30 (s, 1H); $^{13}$C-NMR (CDCl$_3$, 50 MHz) δ: 203.13, 165.27, 163.55, 161.66, 146.00, 136.37, 135.19, 132.83, 129.28, 128.67, 128.17, 127.48, 123.68, 122.71, 122.01, 118.62, 114.86, 70.13, 66.70, 50.09, 28.63; Anal. Calcd for C$_{26}$H$_{26}$N$_2$O$_4$; C, 72.54; H, 6.09; N, 6.51.

N-(2-Acetyl-4-pyrrolidinophenyl)-4-benzyloxybenzamide (99) was obtained from 61 and 85, using the same synthetic procedure as for 92. The crude product was purified by column chromatography (silica gel, EtOAc/CH$_2$Cl$_2$=1:4) to give 99 as yellow solid. (1.6 g, 3.9 mmol); yield 71.7%; mp 175-178° C.; MS (EI, 70 eV): m/z 414.2 (M$^+$); $^1$H-NMR (CDCl$_3$, 200 MHz): δ 2.03 (m, 4H), 2.66 (s, 3H), 3.29 (m, 4H), 5.12 (s, 2H), 6.84 (d, J=9.2 Hz, 1H), 7.07-6.97 (m, 3H), 7.40-7.33 (m, 5H), 7.98 (d, J=7.6 Hz, 1H), 8.01 (d, J=3.2 Hz, 1H), 8.78 (d, J=9.2 Hz, 1H), 12.15 (s, 1H); $^{13}$C-NMR (CDCl$_3$, 50 MHz) 203.62, 164.90, 162.20, 161.40, 143.38, 136.46, 130.93, 129.14, 128.66, 128.13, 127.92, 127.49, 123.11, 122.27, 118.68, 114.76, 113.23, 70.10, 47.95, 28.63, 25.42; Anal. Calcd for C$_{26}$H$_{26}$N$_2$O$_3$; C, 75.34; H, 6.32; N, 6.76, N-(2-Acetyl-4-dimethylaminophenyl)-4-(benzyloxy)benzamide (100) was obtained from 62 and 85, using the same synthetic procedure as for 92. The crude product was purified by column chromatography (silica gel, CH$_2$Cl$_2$) to give 100 as yellow solid. (1.7 g, 4.4 mmol); yield 65.0%; mp 139-140° C.; MS (EI, 70 eV): m/z 388.2 (M$^+$); $^1$H-NMR (CDCl$_3$, 200 MHz): δ 2.66 (s, 3H), 2.94 (s, 6H), 5.10 (s, 2H), 7.00-7.06 (m, 3H), 7.17 (d, J=2.8 Hz, 1H), 7.33-7.44 (m, 5H), 7.97 (d, J=1.6 Hz, 1H), 8.00 (d, J=1.6 Hz, 1H), 8.80 (d, J=9.2 Hz, 1H), 12.19 (s, 1H); $^{13}$C-NMR (CDCl$_3$, 50 MHz) δ: 203.50, 165.00, 161.49, 145.80, 136.44, 132.21, 129.19, 128.66, 128.14, 127.78, 127.49, 122.91, 122.06, 120.06, 114.80, 70.11, 40.97, 28.60; Anal. Calcd for C$_{24}$H$_{24}$N$_2$O$_3$; C, 74.21; H, 6.23; N, 7.21.

N-(2-Acetyl-4-morpholinophenyl)-4-(benzyloxy)-3-methoxybenzamide (101) was obtained from 60 and 86, using the same synthetic procedure as for 92. The crude product was purified by column chromatography (silica gel, CH$_2$Cl$_2$/n-hexane=5:1) to give 101 as yellow solid. (1.9 g, 4.1 mmol); yield 82.6%; mp 192-194° C.; MS (EI, 70 eV): m/z 460.2 (M$^+$); $^1$H-NMR (CDCl$_3$, 200 MHz): δ 2.67 (s, 3H), 3.13 (m, 4H), 3.86 (m, 4H), 5.22 (s, 2H), 6.93 (d, J=8.4 Hz, 1H), 7.54 (dd, J=9.2, 2.8 Hz, 1H), 7.30-7.45 (m, 6H), 7.54 (dd, J=8.4, 2.0 Hz, 1H), 7.61 (d, J=2.0 Hz, 1H), 8.84 (d, J=9.2 Hz, 1H), 12.15 (s, 1H); $^{13}$C-NMR (CDCl$_3$, 50 MHz) δ: 203.09, 165.26, 151.16, 149.59, 136.52, 134.94, 128.65, 128.02, 127.90, 127.21, 123.58, 122.72, 121.90, 120.03, 118.43, 112.91, 111.14, 70.88, 66.77, 56.08, 49.95, 28.59; Anal. Calcd for C$_{22}$H$_{28}$N$_2$O$_5$; C, 70.42; H, 6.13; N, 6.08.

N-(2-Acetyl-4-pyrrolidinophenyl)-4-(benzyloxy)-3-methoxybenzamide (102) was obtained from 61 and 86, using the same synthetic procedure as for 92. The crude product was purified by column chromatography (silica gel, CH$_2$Cl$_2$/n-hexane=3:1) to give 102 as yellow solid. (2.0 g, 4.5 mmol); yield 83.6%; mp 152-154° C.; MS (EI, 70 eV): m/z 444.6 (M$^+$); $^1$H-NMR (CDCl$_3$, 200 MHz): δ 2.04 (m, 4H), 2.66 (s, 3H), 3.30 (m, 4H), 3.98 (s, 3H), 5.22 (s, 2H), 6.84 (dd, J=9.2, 2.8 Hz, 1H), 6.92 (d, J=8.4 Hz, 1H), 7.97 (m, 1H), 7.24-7.45 (m, 5H), 7.53 (dd, J=8.4, 2.0 Hz, 1H), 7.63 (d, J=2.0 Hz, 1H), 8.77 (d, J=9.2 Hz, 1H), 12.17 (s, 1H); $^{13}$C-NMR (CDCl$_3$, 50 MHz)δ: 203.09, 165.26, 151.16, 149.59, 136.52, 134.94, 128.65, 128.02, 127.90, 127.21, 123.58, 122.72, 121.90, 120.03, 118.43, 112.91, 111.14, 70.88, 66.77, 56.08, 49.95, 28.59; Anal. Calcd for C$_{27}$H$_{28}$N$_2$O$_4$; C, 72.95; H, 6.35; N, 6.30.

N-(2-Acetyl-4-morpholinophenyl)benzo[d][1,3]dioxole-4-carboxamide (103) was obtained from 60 and 87, using the same synthetic procedure as for 92. The crude product was purified by column chromatography (silica gel, CHCl$_3$/n-hexane=10:1) to give 103 as yellow solid. (1.06 g, 2.88 mmol); yield 79.3%; mp 150-152° C.; MS (EI, 70 eV): m/z 368.5 (M$^+$); $^1$H-NMR (CDCl$_3$, 200 MHz): δ 2.62 (s, 3H), 3.15 (m, 4H), 3.89 (m, 4H), 6.17 (s, 2H), 6.90-6.96 (m, 2H), 7.50 (dd, J=9.2, 2.8 Hz, 1H), 7.50 (dd, J=6.6, 2.8 Hz, 1H), 7.38 (m, 1H), 8.70 (d, J=9.2 Hz, 1H), 11.87 (s, 1H); $^{13}$C-NMR (CDCl$_3$, 50 MHz) δ: 2201.77, 162.60, 148.12, 145.80, 133.50, 124.69, 123.63, 122.57, 121.95, 121.78, 118.29, 116.95, 111.51, 101.79, 66.60, 50.07, 28.59; Anal. Calcd for C$_{20}$H$_{20}$N$_2$O$_5$; C, 65.21; H, 5.47; N, 7.60.

N-(2-Acetyl-4-pyrrolidinophenyl)benzo[d][1,3]dioxole-4-carboxamide (104) was obtained from 61 and 87, using the same synthetic procedure as for 92. The crude product was purified by column chromatography (silica gel, CH$_2$Cl$_2$/n-hexane=8:1) to give 104 as yellow solid. (0.8 g, 2.3 mmol); yield 57.9%; mp 139-141° C.; MS (EI, 70 eV): m/z 352.1 (M$^+$); $^1$H-NMR (CDCl$_3$, 200 MHz): δ 2.01 (m, 4H), 2.61 (s, 3H), 3.31 (m, 4H), 6.17 (s, 2H), 6.81-7.01 (m, 4H), 7.50 (dd, J=6.2, 3.2 Hz, 1H), 8.60 (d, J=9.2 Hz, 1H), 11.87 (s, 1H); $^{13}$C-NMR (CDCl$_3$, 50 MHz) δ 202.25, 162.21, 148.06, 145.67, 125.24, 124.01, 121.98, 121.68, 117.32, 111.22, 101.70, 48.37, 48.56, 25.38; Anal. Calcd for C$_{20}$H$_{20}$N$_2$O$_4$; C, 68.17; H, 5.72; N, 7.95.

N-(2-Acetyl-4-morpholinophenyl)-2,3-dimethoxybenzamide (105) was obtained from 60 and 88, using the same synthetic procedure as for 92. The crude product was purified by column chromatography (silica gel, CHCl$_3$/n-hexane=10:1) to give 105 as yellow solid. (1.5 g, 3.9 mmol); yield 78.2%; mp 146-148° C.; MS (EI, 70 eV): ml: 384.5 (M$^+$); $^1$H-NMR (CDCl$_3$, 200 MHz): δ 2.61 (s, 3H), 3.15 (m, 4H), 3.87 (m, 4H), 3.99 (s, 3H), 4.05 (s, 3H), 6.99-7.62 (m, 5H), 8.78 (d, J=9.2 Hz, 1H), 12.15 (s, 1H); $^{13}$C-NMR (CDCl$_3$, 200 MHz) δ 201.30, 164.52, 152.94, 147.73, 146.29, 133.20, 128.39, 125.43, 124.01, 123.71, 122.50, 122.19, 117.98, 115.51, 66.67, 61.61, 56.09, 50.03, 28.58; Anal. Calcd for $C_{21}H_{24}N_2O_5$; C, 65.61; H, 6.29; N, 7.29.

N-(2-Acetyl-4-pyrrolidinophenyl)-2,3-dimethoxybenzamide (106) was obtained from 61 and 88, using the same synthetic procedure as for 92. The crude product was purified by column chromatography (silica gel, $CH_2Cl_2$/n-hexane=10:1) to give 106 as yellow solid. (1.4 g, 3.8 mmol); yield 77.6%; mp 137-140° C.; MS (EI, 70 eV): m/z 368.5 (M$^+$); $^1$H-NMR (CDCl$_3$, 200 MHz): δ 2.00 (m, 4H), 2.59 (s, 3H), 3.28 (m, 4H), 3.86 (s, 3H), 3.98 (s, 3H), 6.74 (m, 4H), 7.14-6.92 (m, 3H), 7.59 (dd, J=7.6, 1.8 Hz, 1H), 8.63 (d, J=9.0 Hz, 1H), 11.96 (s, 1H); $^{13}$C-NMR (CDCl$_3$, 50 MHz) δ: 201.83, 164.07, 152.92, 147.66, 143.71, 128.76, 125.96, 124.00, 123.94, 122.46, 117.32, 115.24, 112.79, 61.58, 56.08, 48.03, 28.59, 25.39; Anal. Calcd for $C_{21}H_{24}N_2O_4$; C, 68.46; H, 6.57; N, 7.60.

N-(2-Acetyl-4-morpholinophenyl)-2,5-dimethoxybenzamide (107) was obtained from 60 and 89, using the same synthetic procedure as for 92. The crude product was purified by column chromatography (silica gel, CHCl$_3$/EtOAc=8:1) to give 107 as yellow solid. (1.67 g, 4.3 mmol); yield 79.7%; mp 172-174° C.; MS (EI, 70 eV): ink: 384.5 (M$^+$); $^1$H-NMR (CDCl$_3$, 200 MHz): δ 2.61 (s, 3H), 3.15 (m, 4H), 3.80 (s, 3H), 3.87 (m, 4H), 4.07 (s, 3H), 6.95-7.32 (m, 4H), 7.73 (d, J=2.8 Hz, 1H), 8.78 (d, J=9.2 Hz, 1H), 12.25 (s, 1H); $^{13}$C-NMR (CDCl$_3$, 50 MHz) δ 201.21, 164.05, 153.63, 151.95, 146.52, 132.80, 125.75, 123.96, 122.95, 122.01, 119.69, 117.66, 115.69, 112.79, 66.79, 56.12, 55.83, 49.86, 28.76; Anal. Calcd for $C_{21}H_{24}N_2O_5$; C, 65.61; H, 6.29; N, 7.29.

N-(2-Acetyl-4-pyrrolidinophenyl)-2,5-dimethoxybenzamide (108) was obtained from 61 and 89, using the same synthetic procedure as for 92. The crude product was purified by column chromatography (silica gel, $CH_2Cl_2$/n-hexane=8:1) to give 108 as yellow solid. (1.6 g, 4.3 mmol); yield 73.8%; mp 137-140° C.; MS (EI, 70 eV): m/z 368.5 (M"); $^1$H-NMR (CDCl$_3$, 200 MHz): δ 2.01 (m, 4H), 2.60 (s, 3H), 3.29 (m, 4H), 3.80 (s, 3H), 4.06 (s, 3H), 6.77 (dd, J=9.2, 3.0 Hz, 1H), 6.89-6.97 (m, 3H), 7.74 (d, J=2.8 Hz, 1H), 8.64 (d, J=9.2 Hz, 1H), 12.08 (s, 1H); $^{13}$C-NMR (CDCl$_3$, 200 MHz) δ 201.75, 163.61, 153.61, 151.91, 143.69, 128.64, 126.30, 124.32, 123.30, 119.36, 117.20, 115.62, 112.78, 56.15, 55.83, 47.94, 28.77, 25.42; Anal. Calcd for $C_{21}H_{24}N_2O_4$; C, 68.46; H, 6.57; N, 7.60.

N-(2-Acetyl-4-morpholinophenyl)-2-methoxybenzamide (109) was obtained from 60 and 90, using the same synthetic procedure as for 92. The crude product was purified by column chromatography (silica gel, $CH_2Cl_2$/n-hexane=10:1) to give 109 as yellow solid. (1.4 g, 3.9 mmol); yield 72.6%; mp 158-160° C.; MS (EI, 70 eV): m/z 354.5 (M$^+$); $^1$H-NMR (CDCl$_3$, 200 MHz): δ 2.60 (s, 3H), 3.12 (m, 4H), 3.85 (m, 4H), 4.09 (s, 3H), 6.96-7.07 (m, 2H), 7.13 (dd, J=9.2, 3:0 Hz, 1H), 7.34-7.43 (m, 2H), 8.14 (dd, J=7.6, 1.8 Hz, 1H), 8.80 (d, J=9.2 Hz, 1H), 12.23 (s, 1H); $^{13}$C-NMR (CDCl$_3$, 50 MHz) δ 201.25, 164.33, 157.56, 146.18, 133.01, 132.25, 125.46, 123.83, 122.63, 122.18, 120.89, 117.92, 111.31, 66.69, 55.58, 49.98, 28.76; Anal. Calcd for $C_{20}H_{22}N_2O_4$; C, 67.78; H, 6.26; N, 7.90.

N-(2-Acetyl-4-pyrrolidinophenyl)-2-methoxybenzamide (110) was obtained from 61 and 90, using the same synthetic procedure as for 92. The crude product was purified by column chromatography (silica gel, $CH_2Cl_2$) to give 110 as yellow solid. (1.1 g, 3.3 mmol); yield 83.1%; mp 168-170° C.; MS (EI, 70 eV): m/z. 338.5 (M$^+$); $^1$H-NMR (CDCl$_3$, 200 MHz): δ 1.96 (m, 4H), 2.64 (s, 3H), 3.27 (m, 4H), 4.05 (s, 3H), 6.81 (dd, J=9.0, 2.6 Hz, 1H), 7.00-7.53 (m, 4H), 7.96 (dd, J=7.8, 1.8 Hz, 1H), 8.50 (d, J=9.0 Hz, 1H), 11.87 (s, 1H); $^{13}$C-NMR (CDCl$_3$, 50 MHz) δ 202.81, 163.21, 157.44, 144.08, 133.51, 131.70, 127.89, 126.64, 123.70, 122.76, 121.13, 117.04, 113.42, 112.51, 56.17, 47.94, 29.37, 25.38; Anal. Calcd for $C_{20}H_{22}N_2O_3$; C, 70.99; H, 6.55; N, 8.28.

N-(2-Acetyl-4-morpholinophenyl)-2-methoxybenzamide (111) was obtained from 60 and 91, using the same synthetic procedure as for 92. The crude product was purified by column chromatography (silica gel, $CH_2Cl_2$/EtOAc=15:1) to give 111 as yellow solid. (1.1 g, 3.1 mmol); yield 76.0%; mp 185-187° C.; MS (EI, 70 eV): m/z 354.5 (M$^+$); $^1$H-NMR (CDCl$_3$, 200 MHz): δ 2.67 (s, 3H), 3.13 (m, 4H), 3.84 (s, 3H), 3.86 (m, 4H), 6.95 (d, J=2.0 Hz, 1H), 6.98 (d, J=2.0 Hz, 1H), 7.21 (dd, J=9.2, 2.8 Hz, 1H), 7.38 (d, J=2.8 Hz, 1H), 7.97 (d, J=2.0 Hz, 1H), 8.00 (d, J=2.0 Hz, 1H), 8.85 (d, J=9.2 Hz, 1H), 12.29 (s, 1H); $^{13}$C-NMR (CDCl$_3$, 50 MHz) δ 203.11, 165.30, 162.48, 146.21, 135.01, 1229.24, 127.29, 123.61, 122.72, 121.99, 118.39, 113.95, 66.78, 55.42, 49.95, 28.61; Anal. Calcd for $C_{20}H_{22}N_2O_4$; C, 67.78; H, 6.26; N, 7.90.

N-(2-Acetyl-4-pyrrolidinophenyl)-4-methoxybenzamide (112) was obtained from 61 and 91, using the same synthetic procedure as for 92. The crude product was purified by column chromatography (silica gel, $CH_2Cl_2$/n-hexane=10:1) to give 112 as yellow solid. (1.2 g, 3.5 mmol); yield 72.5%; mp 174-175° C.; MS (EI, 70 eV): m/z 338.5 (M$^+$); $^1$H-NMR (CDCl$_3$, 200 MHz): $CH_2Cl_2$/n-hexane=10:1; NMR (CDCl$_3$, 50 MHz) δ 203.60, 164.95, 162.25, 143.27, 132.19, 129.12, 127.67, 123.10, 122.24, 118.74, 113.87, 55.39, 48.02, 28.60, 25.38; Anal. Calcd for $C_{20}H_{22}N_2O_3$; C, 70.99; H, 6.55; N, 8.28.

2-(2-Benzyloxyphenyl)-6-morpholinoquinolin-4-one (113). To a solution of 92 (1.2 g, 2.7 mmol) in 1,4 dioxane (150 ml) was added NaOH (0.9 g, 21.4 mmol). The mixture was refluxed for 5 h, concentrated and added 10% $NH_4Cl$ (100 ml). The precipitate was collected and washed with $H_2O$ and acetone. The crude product was purified by column chromatography (silica gel, CHCl$_3$:MeOH=25:1) to give 113 as yellow solid (1.3 g, 3.2 mmol). Yield: 65.4%; mp 281-283° C.; MS (EI, 70 eV): m/z 412.4 (M$^+$); $^1$H-NMR (DMSO-d$_6$. 200 MHz): δ 3.15 (m, 4H), 3.77 (m, 4H), 5.12 (s, 2H), 6.30 (s, 1H), 7.36-7.50 (m, 11H), 7.66 (d, J=9.2 Hz, 1H), 11.57 (s, 1H); Anal. Calcd for $C_{26}H_{24}N_2O_3$; C, 75.71; H, 5.86; N, 6.79.

2-(2-Benzyloxyphenyl)-6-pyrrolidinoquinolin-4-one (114) was obtained from 93, using the same synthetic procedure as for 113. The crude product was purified by column chromatography (silica gel, CHCl$_3$:MeOH=25:1) to give 114 as yellow solid. (0.7 g, 1.8 mmol). Yield: 61.1%; mp 293-295° C.; MS (EI, 70 eV): m/z 396.4 (M$^+$); $^1$H-NMR (DMSO-d$_6$, 200 MHz): δ 1.99 (m, 4H), 3.34 (m, 4H), 5.21 (s, 2H), 6.33 (s, 1H), 7.00-7.50 (m, 1H), 7.68 (d, J=9.0 Hz, 1H), 11.63 (s, 1H); Anal. Calcd for $C_{26}H_{24}N_2O_2$; C, 78.76; H, 6.10; N, 7.07.

2-(2-Benzyloxyphenyl)-6-dimethylaminoquinolin-4-one (115) was obtained from 94, using the same synthetic procedure as for 113. The crude product was purified by column chromatography (silica gel, CHCl$_3$:MeOH=25:1) to give 115 as yellow solid. (1.2 g, 1.8 mmol). Yield: 61.1%; mp 210-212° C.; MS (EI, 70 eV): m/z 370.2 (M$^+$); $^1$H-NMR (DMSO-d$_6$, 200 MHz): δ 2.91 (s, 6H), 5.13 (s, 2H), 6.02 (s, 1H), 7.07 (t, J=7.4 Hz, 1H), 7.17 (d, J=2.6 Hz, 1H), 7.22-7.48 (m, 9H), 7.53 (d, J=9.2 Hz, 1H), 11.67 (s, 1H); Anal. Calcd for $C_{24}H_{22}N_2O_2$; C, 77.81; H, 5.99; N, 7.56.

2-(3-Benzyloxyphenyl)-6-morpholinoquinolin-4-one (116) was obtained from 95, using the same synthetic procedure as for 113. The crude product was purified by column chromatography (silica gel, CHCl$_3$:MeOH=25:1) to give 116 as yellow solid. (0.8 g, 1.9 mmol). Yield: 61.1%; mp 283-285° C.; MS (EI, 70 eV): m/z 412.4 (M$^+$); $^1$H-NMR (DMSO-d$_6$, 200 MHz): δ 3.15 (m, 4H), 3.77 (m, 4H), 5.12 (s, 2H), 6.30 (s, 1H), 7.36-7.50 (m, 11H), 7.66 (d, J=9.2 Hz, 1H), 11.57 (s, 1H); Anal. Calcd for $C_{26}H_{24}N_2O_3$; C, 75.71; H, 5.86; N, 6.79.

2-(3-Benzyloxyphenyl)-6-pyrrolidinoquinolin-4-one (117) was obtained from 96, using the same synthetic procedure as for 113. The crude product was purified by column chromatography (silica gel, $CHCl_3$:MeOH=25:1) to give 117 as yellow solid. (0.38 g, 0.95 mmol). Yield: 66.3%; mp 320-322° C.; MS (EI, 70 eV): m/z 396.4 ($M^+$); $^1$H-NMR (DMSO-$d_6$, 200 MHz): δ 2.07 (m, 4H), 3.34 (m, 4H), 5.21 (s, 2H), 6.35 (s, 1H), 6.87-7.49 (m, 10H), 7.70 (d, J=9.0 Hz, 1H), 7.78 (d, J=8.6 Hz, 1H), 11.50 (s, 1H); Anal. Calcd for $C_{26}H_{24}N_2O_2$; C, 78.76; H, 6.10; N, 7.07.

2-(3-Benzyloxyphenyl)-6-dimethylaminoquinolin-4-one (118) was obtained from 97, using the same synthetic procedure as for 113. The crude product was purified by column chromatography (silica gel, $CHCl_3$:MeOH=25:1) to give 118 as yellow solid. (1.3 g, 3.5 mmol). Yield: 65.6%; mp 307-308° C.; MS (EI, 70 eV): m/z 370.2 ($M^+$); $^1$H-NMR (DMSO-$d_6$, 200 MHz): δ 2.91 (s, 6H), 5.13 (s, 2H), 6.02 (s, 1H), 7.07 (t, J=7.4 Hz, 1H), 7.17 (d, J=2.6 Hz, 1H), 7.22-7.48 (m, 9H), 7.53 (d, J=9.2 Hz, 1H), 11.67 (s, 1H); Anal. Calcd for $C_{24}H_{22}N_2O_2$; C, 77.81; H, 5.99; N, 7.56.

2-(4-Benzyloxyphenyl)-6-morpholinoquinolin-4-one (119) was obtained from 98, using the same synthetic procedure as for 113. The crude product was purified by column chromatography (silica gel, $CHCl_3$:MeOH=25:1) to give 119 as yellow solid. (0.5 g, 1.2 mmol). Yield: 52.2%; mp 320-323° C.; MS (EI, 70 eV): m/z 412.4 ($M^+$); $^1$H-NMR (DMSO-$d_6$, 200 MHz): δ 3.14 (m, 4H), 3.77 (m, 4H), 5.21 (s, 2H), 6.24 (s, 1H), 7.16-7.49 (m, 9H), 7.66 (d, J=9.0 Hz, 1H), 7.76 (d, J=8.6 Hz, 1H), 11.48 (s, 1H); Anal. Calcd for $C_{26}H_{24}N_2O_3$; C, 75.71; H, 5.86; N, 6.79.

2-(4-Benzyloxyphenyl)-6-pyrrolidinoquinolin-4-one (120) was obtained from 99, using the same synthetic procedure as for 113. The crude product was purified by column chromatography (silica gel, $CHCl_3$:MeOH=25:1) to give 120 as yellow solid. (0.6 g, 1.5 mmol). Yield: 57.5%; mp 330-332° C.; MS (EI, 70 eV): m/z 396.2 ($M^+$); $^1$H-NMR (DMSO-$d_6$, 200 MHz): δ 1.99 (m, 4H), 3.34 (m, 4H), 5.21 (s, 2H), 6.33 (s, 1H), 7.00-7.50 (m, 11H), 7.68 (d, J=9.0 Hz, 1H), 11.63 (s, 1H); Anal. Calcd for $C_{26}H_{24}N_2O_2$; C, 78.76; H, 6.10; N, 7.07.

2-(4-Benzyloxyphenyl)-6-dimethylaminoquinolin-4-one (121) was obtained from 100, using the same synthetic procedure as for 113. The crude product was purified by column chromatography (silica gel, $CHCl_3$:MeOH=25:1) to give 121 as yellow solid. (1.2 g, 3.2 mmol). Yield: 78.7%; mp 283-285° C.; MS (EI, 70 eV): m/z 370.2 ($M^+$); $^1$H-NMR (DMSO-$d_6$, 200 MHz): δ 2.92 (s, 6H), 5.17 (s, 2H), 6.17 (s, 1H), 7.14 (d, J=8.6 Hz, 2H), 7.24 (dd, J=8.8, 2.4 Hz, 1H), 7.29-7.46 (m, 6H), 7.53 (d, J=9.0 Hz, 1H), 7.73 (d, J=8.6 Hz, 2H), 11.38 (s, 1H); Anal. Calcd for $C_{24}H_{22}N_2O_2$; C, 77.81; N, 7.56.

2-(4-(Benzyloxy)-3-methoxyphenyl)-6-morpholino-quinolin-4-one (122) was obtained from 101, using the same synthetic procedure as for 113. The crude product was purified by column chromatography (silica gel, $CHCl_3$:MeOH=25:1) to give 122 as yellow solid. (0.5 g, 1.1 mmol). Yield: 52.1%; nip 300-301° C.; MS (EI, 70 eV): m/z 442.2 ($M^+$); $^1$H-NMR (DMSO-$d_6$, 200 MHz): δ 3.11 (m, 4H), 3.74 (m, 4H), 5.15 (s, 2H), 6.28 (s, 1H), 7.16 (d, J=8.2 Hz, 2H), 7.25-7.45 (m, 9H), 7.68 (d, J=9.0 Hz, 1H), 11.48 (br, 1H); Anal. Calcd for $C_{27}H_{26}N_2O_4$; C, 72.28; H, 5.92; N, 6.23.

2-(4-(Benzyloxy)-3-methoxyphenyl)-6-pyrrolidinoquino-lin-4-one (123) was obtained from 102, using the same synthetic procedure as for 113. The crude product was purified by column chromatography (silica gel, $CHCl_3$:MeOH=25:1) to give 123 as yellow solid. (1.3 g, 3.1 mmol). Yield: 65.2%; mp 304-306° C.; MS (EI, 70 eV): m/z 426.6 ($M^+$); $^1$H-NMR (DMSO-$d_6$, 200 MHz): δ 1.99 (m, 4H), 3.33 (m, 4H), 3.89 (s, 3H), 5.18 (s, 2H), 6.25 (s, 1H), 7.02-7.09 (m, 2H), 7.19 (d, J=8.2 Hz, 1H), 7.33-7.45 (m, 2H), 7.64 (d, J=8.8 Hz, 1H), 11.34 (s, 1H); Anal. Calcd for $C_{27}H_{26}N_2O_3$; C, 76.03; H, 6.14; N, 6.57.

2-(Benzo[d][1,3]-dioxol-4-yl)-6-morpholinoquinolin-4-one (124) was obtained from 103, using the same synthetic procedure as for 113. The crude product was purified by column chromatography (silica gel, $CHCl_3$:MeOH=25:1) to give 124 as yellow solid. (0.5 g, 1.4 mmol). Yield: 52.6%; mp 350-352° C.; MS (EI, 70 eV): m/z 350.5 ($M^+$); $^1$H-NMR (DMSO-$d_6$, 200 MHz): δ 3.16 (m, 4H), 3.77 (m, 4H), 6.15 (s, 2H), 6.43 (s, 1H), 7.04 (d, J=7.8 Hz, 1H), 7.09 (dd, J=7.8, 1.8 Hz, 1H), 7.28 (d, J=7.0 Hz, 1H), 7.40 (d, J=2.8 Hz, 1H), 7.50 (dd, J=9.2, 2.8 Hz, 1H), 7.67 (d, J=9.2 Hz, 1H), 11.54 (s, 1H); Anal. Calcd for $C_{20}H_{18}N_2O_4$; C, 68.56; H, 5.18; N, 8.00.

2-(Benzo[d][1,3]-dioxol-4-yl)-6-pyrrolidinoquinolin-4-one (125) was obtained from 104, using the same synthetic procedure as for 113. The crude product was purified by column chromatography (silica gel, $CHCl_3$:MeOH=25:1) to give 125 as yellow solid. (0.2 g, 0.6 mmol). Yield: 52.6%; mp 330-332° C.; MS (EI, 70 eV): m/z 334.4 ($M^+$); $^1$H-NMR (DMSO-$d_6$, 200 MHz): δ 1.95 (m, 4H), 3.16 (m, 4H), 6.11 (s, 2H), 6.25 (s, 1H), 6.96-7.06 (m, 2H), 7.19 (d, J=6.8 Hz, 1H), 7.57 (d, J=9.0 Hz, 1H), 11.39 (s, 1H); Anal. Calcd for $C_{20}H_{18}N_2O_3$; C, 71.84; H, 5.43; N, 8.38.

2-(2,3-Dimethoxyphenyl)-6-morpholinoquinolin-4-one (126) was obtained from 105, using the same synthetic procedure as for 113. The crude product was purified by column chromatography (silica gel, $CHCl_3$:MeOH=25:1) to give 126 as yellow solid. (0.5 g, 1.4 mmol). Yield: 52.5%; mp 235-236° C.; MS (EI, 70 eV): ml: 366.5 ($M^+$); $^1$H-NMR (DMSO-$d_6$, 200 MHz): δ 3.11 (m, 4H), 3.60 (s, 3H), 3.83 (m, 4H), 3.96 (s, 3H), 5.98 (s, 1H), 6.96-7.447 (m, 5H), 7.54 (d, J=9.6 Hz, 1H), 11.63 (s, 1H); $^{13}$C-NMR (DMSO-$d_6$, 50 MHz) δ 176.63, 153.13, 147.90, 147.02, 146.66, 134.72, 129.90, 126.00, 124.84, 123.01, 121.98, 119.96, 114.93, 108.72, 107.52, 66.53, 61.13, 56.43, 49.47; Anal. Calcd for $C_{21}H_{22}N_2O_4$; C, 68.84; H, 6.05; N, 7.65.

2-(2,3-Dimethoxyphenyl)-6-pyrrolidinoquinolin-4-one (127) was obtained from 106, using the same synthetic procedure as for 113. The crude product was purified by column chromatography (silica gel, $CHCl_3$:MeOH=25:1) to give 127 as yellow solid. (0.3 g, 0.9 mmol). Yield: 52.5%; mp 258-260° C.; MS (EI, 70 eV): m/z 350.5 ($M^+$); $^1$H-NMR (DMSO-$d_6$, 200 MHz): δ 1.95 (m, 4H), 3.23 (m, 4H), 3.60 (s, 3H), 3.84 (s, 3H), 5.92 (s, 1H), 6.97-7.19 (m, 5H), 7.54 (d, J=8.4 Hz, 1H), 11.48 (s, 1H); $^{13}$C-NMR (DMSO-$d_6$, 50 MHz) δ 176.49, 153.13, 146.67, 146.07, 144.85, 132.16, 126.71, 124.78, 122.02, 119.99, 119.12, 114.77, 107.83, 103.18, 61.10, 56.43, 48.11, 25.44; Anal. Calcd for $C_{21}H_{22}N_2O_3$; C, 71.98; H, 6.33; N, 7.99.

2-(2,5-Dimethoxyphenyl)-6-morpholinoquinolin-4-one (128) was obtained from 107, using the same synthetic procedure as for 113. The crude product was purified by column chromatography (silica gel, $CHCl_3$:MeOH=25:1) to give 128 as yellow solid. (0.7 g, 1.9 mmol). Yield: 61.2%; nip 275-277° C.; MS (EI, 70 eV): m/z 366.2 ($M^+$); $^1$H-NMR (DMSO-$d_6$, 200 MHz): δ 3.14 (m, 4H), 3.75 (m, 10H), 6.03 (s, 1H), 7.03-7.49 (m, 5H), 7.67 (d, J=9.0 Hz, 1H), 11.57 (s, 1H); $^{13}$C-NMR (DMSO-$d_6$, 50 MHz) δ 176.67, 153.49, 150.98, 147.80, 147.00, 134.68, 125.97, 124.87, 122.89, 119.92, 116.57, 113.71, 108.93, 107.46, 66.53, 56.64, 49.45; Anal. Calcd for $C_{21}H_{22}N_2O_4$; C, 68.84; H, 6.05; N, 7.65.

2-(2,5-Dimethoxyphenyl)-6-pyrrolidinoquinolin-4-one (129) was obtained from 108, using the same synthetic procedure as for 113. The crude product was purified by column chromatography (silica gel, CHCl$_3$:MeOH=25:1) to give 129 as yellow solid. (0.9 g, 0.9 mmol). Yield: 59.2%; mp 272-274° C.; MS (EI, 70 eV): m/z 350.2 (10; IR (KBr): 1606.77 (C=O), 2978.22 (—NH) cm$^{-1}$, $^1$H-NMR (DMSO-d$_6$, 200 MHz): δ 1.95 (m, 4H), 3.25 (m, 4H), 3.71 (s, 3H), 3.72 (s, 3H), 5.94 (s, 2H), 6.99-7.11 (m, 5H), 7.49 (d, J=8.6 Hz, 1H), 11.43 (s, 1H); Anal. Calcd for C$_{21}$H$_{22}$N$_2$O$_3$; C, 71.98; H, 6.33; N, 7.99.

2-(2-Methoxyphenyl)-6-morpholinoquinolin-4-one (130) was obtained from 109, using the same synthetic procedure as for 113. The crude product was purified by column chromatography (silica gel, CHCl$_3$:MeOH=25:1) to give 130 as yellow solid. (0.6 g, 1.8 mmol). Yield: 57.5%; mp 262-264° C.; MS (EI, 70 eV): m/z 336.5 (M$^+$); $^1$H-NMR (DMSO-d$_6$, 200 MHz): δ 3.10 (m, 4H), 3.74 (m, 4H), 3.76 (s, 3H), 5.97 (s, 1H); 7.05 (d, J=7.6 Hz, 1H), 7.16 (d, J=8.2 Hz, 1H), 7.40-7.54 (m, 5H), 11.55 (s, 1H); $^{13}$C-NMR (DMSO-d$_6$, 50 MHz) δ 176.61, 156.96, 147.79, 147.42, 134.82, 131.73, 130.69, 125.89, 124.39, 122.89, 121.06, 119.97, 112.34, 108.85, 107.44, 66.54, 56.16, 49.48; Anal. Calcd for C$_{20}$H$_{20}$N$_2$O$_3$; C, 71.41; H, 5.99; N, 8.33.

2-(2-Methoxyphenyl)-6-pyrrolidinoquinolin-4-one (131) was obtained from 110, using the same synthetic procedure as for 113. The crude product was purified by column chromatography (silica gel, CHCl$_3$:MeOH=25:1) to give 131 as yellow solid. (0.7 g, 2.2 mmol). Yield: 62.3%; mp 312-313° C.; MS (EI, 70 eV): m1:320.2 (M$^+$); $^1$H-NMR (DMSO-d$_6$, 200 MHz): δ 1.98 (m, 4H), 3.25 (m, 4H), 3.77 (s, 3H), 5.91 (s, 1H), 7.00-7.51 (m, 7H), 11.43 (s, 1H); $^{13}$C-NMR (DMSO-d$_6$, 50 MHz) δ 176.58, 156.97, 146.43, 144.75, 132.13, 131.60, 130.69, 126.65, 124.53, 121.04, 119.93, 119.05, 112.33, 108.03, 103.16, 56.15, 48.09, 25.45; Anal. Calcd for C$_{20}$H$_{20}$N$_2$O$_2$; C, 74.98; H, 6.29; N, 8.74.

2-(4-Methoxyphenyl)-6-morpholinoquinolin-4-one (132) was obtained from 111, using the same synthetic procedure as for 113. The crude product was purified by column chromatography (silica gel, CHCl$_3$:MeOH=25:1) to give 132 as yellow solid. (0.5 g, 1.8 mmol). Yield: 65.9%; mp 302-304° C.; MS (EI, 70 eV): m/z 336.2 (M); $^1$H-NMR (DMSO-d$_6$, 200 MHz): δ 3.10 (m, 4H), 3.74 (m, 4H), 3.80 (s, 3H), 6.22 (s, 1H), 7.06 (d, J=8.8 Hz, 2H), 7.38 (d, J=2.4 Hz, 1H), 7.43 (dd, J=9.2, 2.8 Hz, 1H), 7.64 (d, J=9.2 Hz, 1H), 7.74 (d, J=8.8 Hz, 2H), 11.45 (s, 1H); Anal. Calcd for C$_{20}$H$_{20}$N$_2$O$_3$; C, 71.41; H, 5.99; N, 8.33.

2-(4-Methoxyphenyl)-6-pyrrolidinoquinolin-4-one (133) was obtained from 112, using the same synthetic procedure as for 113. The crude product was purified by column chromatography (silica gel, CHCl$_3$:MeOH=25:1) to give 133 as yellow solid. (0.4 g, 1.2 mmol). Yield: 74.0%; mp 312-313° C.; MS (EI, 70 eV): m/z 320.2 (M$^+$); Anal. Calcd for C$_{20}$H$_{20}$N$_2$O$_2$; C, 74.98; H, 6.29; N, 8.74.

2-(2-Hydroxyphenyl)-6-morpholinoquinolin-4-one (134). To a suspension of 113 (0.4 g, 1.0 mmol) in MeOH (400 ml) was hydrogenated in the presence of 10% Pd/C (0.1 g) at 25☐ for 3 h. The catalyst was filtered off and the filtrate was evaporated. The crude product was purified by column chromatography (SiO$_2$, CHCl$_3$:MeOH=25:1) to give 134 as yellow solid. (0.3 g, 0.9 mmol). Yield: 81.5%; mp 290-291° C.; MS (EI, 70 eV): m/z 322.2 (M$^+$); IR (KBr): 1612.56 (C=O), 2969.54 (—NH) cm$^{-1}$; $^1$H-NMR (MeOD-d$_4$, 400 MHz) δ 3.30 (m, 4H), 3.87 (m, 4H), 4.48 (s, 4H), 6.64 (s, 1H), 7.02 (d, J=8.8 Hz, 1H), 7.04 (d, J=8.8 Hz, 1H); 7.40 (t, J=8.0 Hz, 1H), 7.60 (d, J=8.8 Hz, 2H), 7.65 (d, J=2.0 Hz, 1H), 7.72 (d, J=9.2 Hz, 1H); Anal. Calcd for C$_{19}$H$_{18}$N$_2$O$_3$; C, 70.79; H, 5.63; N, 8.69.

2-(2-Hydroxyphenyl)-6-pyrrolidinoquinolin-4-one (135) was obtained from 114, using the same synthetic procedure as for 134. The crude product was purified by column chromatography (silica gel, CHCl$_3$:MeOH=25:1) to give 135 as yellow solid. (0.2 g, 0.7 mmol). Yield: 86.6%; mp 304-306° C.; MS (EI, 70 eV): m/z 306.2 (M$^+$); IR (KBr): 1612.56 (C=O), 2969.54 (—NH) cm$^{-1}$; $^1$H-NMR (MeOD-d$_4$. 400 MHz): δ 3.25 (m, 4H), 3.87 (m, 4H), 6.29 (s, 1H), 6.87 (d, J=3.2 Hz, 1H), 6.91 (dd, J=8.8, 3.2 Hz, 1H), 7.03 (d, J=8.8 Hz, 1H), 7.45 (d, J=2.8 Hz, 1H), 7.48 (dd, J=9.2, 2.8 Hz, 1H), 7.61 (d, J=9.2 Hz, 1H), 9.45 (hr, 1H), 11.72 (hr, 1H); Anal. Calcd for C$_{19}$H$_{18}$N$_2$O$_2$; C, 74.49; H, 5.92; N, 9.14.

2-(2-Hydroxyphenyl)-6-dimethylaminoquinolin-4-one (136) was obtained from 115, using the same synthetic procedure as for 134. The crude product was purified by column chromatography (silica gel, CHCl$_3$:MeOH=25:1) to give 136 as yellow solid. Yield: 86.6%; mp 296-298° C.; MS (EI, 70 eV): inlz 280.1 (M$^+$); IR (KBr): 1597.13 (C=O), 2908.78 (—NH) cm$^{-1}$; $^1$H-NMR (MeOD-d$_4$, 200 MHz) δ 3.02 (s, 6H), 6.56 (s, 1H), 6.92-6.99 (m, 2H), 7.27-7.38 (m, 3H), 7.50 (dd, J=8.2, 1.8 Hz, 1H), 7.60 (d, J=8.2 Hz, 1H); Anal. Calcd for C$_{17}$H$_{16}$N$_2$O$_2$; C, 72.84; H, 5.75; N, 9.99.

2-(3-Hydroxyphenyl)-6-morpholinoquinolin-4-one (137) was obtained from 116, using the same synthetic procedure as for 134. The crude product was purified by column chromatography (silica gel, CHCl$_3$:MeOH=25:1) to give 81a as yellow solid. (0.3 g, 0.9 mmol). Yield: 89.7%; mp 357-360° C.; MS (EI, 70 eV): m/z 322.2 (M$^+$); $^1$H-NMR (DMSO-d$_6$, 200 MHz) δ 3.13 (m, 4H), 3.75 (m, 4H), 6.20 (s, 1H), 6.81 (d, J=7.8 Hz, 1H), 7.15-7.22 (m, 2H), 7.33 (d, J=7.8 Hz, 1H), 7.43 (d, J=2.6 Hz, 1H), 7.48 (dd, J=9.0, 2.6 Hz, 1H), 7.69 (d, J=9.0 Hz, 1H), 9.86 (s, 1H), 11.56 (s, 1H); $^{13}$C-NMR (DMSO-d$_6$, 50 MHz) δ 176.78, 158.20, 149.47, 147.95, 136.28, 134.96, 130.59, 125.97, 122.95, 120.39, 118.36, 117.63, 114.38, 107.24, 106.22, 66.52, 49.32, 43.47; Anal. Calcd for C$_{19}$H$_{18}$N$_2$O$_3$; C, 70.79; H, 5.63; N, 8.69.

2-(3-Hydroxyphenyl)-6-pyrrolidinoquinolin-4-one (138) was obtained from 117, using the same synthetic procedure as for 134. The crude product was purified by column chromatography (silica gel, CHCl$_3$:MeOH=25:1) to give 138 as yellow solid. (0.14 g, 0.45 mmol). Yield: 90.9%; mp 364-367° C.; MS (EI, 70 eV): rnlz 306.3 (M$^+$); $^1$H-NMR (DMSO-d$_6$, 200 MHz) δ 1.80 (m, 4H), 3.29 (m, 4H), 6.14 (s, 1H), 6.92 (d, J=7.0 Hz, 1H), 7.02 (d, J=7.0 Hz, 1H), 7.09 (dd, J=9.2, 2.4 Hz, 1H), 7.15-7.21 (m, 2H), 7.34 (t, J=7.8 Hz, 1H), 7.65 (d, J=9.2 Hz, 1H), 9.84 (s, 1H), 11.46 (s, 1H); $^{13}$C-NMR (DMSO-d$_6$, 50 MHz) δ 176.78, 158.20, 149.47, 147.95, 136.28, 134.96, 130.59, 125.97, 122.95, 120.39, 118.36, 117.63, 114.38, 107.24, 106.22, 66.52, 49.32, 43.47; Anal. Calcd for C$_{19}$H$_{18}$N$_2$O$_2$; C, 74.49; H, 5.92; N, 9.14.

2-(3-Hydroxyphenyl)-6-dimethylaminoquinolin-4-one (139) was obtained from 118, using the same synthetic procedure as for 134. The crude product was purified by column chromatography (silica gel, CHCl$_3$:MeOH=25:1) to give 139 as yellow solid. (0.4 g, 1.4 mmol). Yield: 75.6%; mp 342-344° C.; MS (EI, 70 eV): ink: 280.1 (M); $^1$H-NMR (DMSO-d$_6$, 200 MHz) δ 2.93 (s, 6H), 6.23 (s, 1H), 6.92 (d, J=8.0 Hz, 1H), 7.16-7.35 (m, 4H), 7.70 (d, J=9.2 Hz, 1H), 9.93 (s, 1H), 11.46 (s, 1H); $^{13}$C-NMR (DMSO-d$_6$, 50 MHz) δ 175.86, 158.25, 148.99, 147.63, 136.34, 133.33, 130.52, 126.09, 120.64, 120.22, 118.32, 117.58, 114.39, 105.55, 103.94, 38.69; Anal. Calcd for C$_{17}$H$_{16}$N$_2$O$_2$; C, 72.84; H, 5.75; N, 9.99.

2-(4-Hydroxyphenyl)-6-morpholinoquinolin-4-one (140) was obtained from 119, using the same synthetic procedure as for 134. The crude product was purified by column chromatography (silica gel, CHCl$_3$:MeOH=25:1) to give 140 as yellow solid. (0.1 g, 0.3 mmol). Yield: 64.5%; mp 340-342° C.; MS (EI, 70 eV): m/z 322.2 (M$^+$); $^1$H-NMR (DMSO-d$_6$, 200 MHz) δ 3.16 (m, 4H), 3.74 (m, 4H), 6.24 (s, 1H), 6.95 (d, J=8.6 Hz, 2H), 7.40 (d, J=2.6 Hz, 1H), 7.45 (dd, J=9.0, 2.6 Hz, 1H), 7.69 (d, J=9.0 Hz, 3H), 10.05 (s, 1H), 11.50 (br s, 1H); $^{13}$C-NMR (DMSO-d$_6$, 50 MHz) δ 176.38, 159.90, 149.38, 147.81, 135.04, 129.15, 125.76, 125.31, 122.78, 120.23, 116.18, 107.35, 105.34, 66.54, 49.37; Anal. Calcd for C$_{19}$H$_{18}$N$_2$O$_3$; C, 70.79; H, 5.63; N, 8.69.

2-(4-Hydroxyphenyl)-6-pyrrolidinoquinolin-4-one (141) was obtained from 120, using the same synthetic procedure as for 134. The crude product was purified by column chromatography (silica gel, CHCl$_3$:MeOH=25:1) to give 141 as yellow solid. (0.1 g, 0.7 mmol). Yield: 64.9%; mp 304-306° C.; MS (EI, 70 eV): m/z 306.3 (M$^+$); IR (KBr): 1613.52 (C=O), 3132.53 (—NH), 3438.26 (—OH) cm$^{-1}$; $^1$H-NMR (DMSO-d$_o$, 400 MHz) δ 2.02 (m, 4H), 3.37 (m, 4H), 6.93 (s, 1H), 7.04 (d, J=8.4 Hz, 2H), 7.42 (dd, J=9.2, 2.0 Hz, 1H), 7.76 (d, J=8.4 Hz, 1H), 7.83 (d, J=8.4 Hz, 2H), 8.14 (d, J=9.2 Hz, 1H), 10.48 (s, 1H); Anal. Calcd for C$_{19}$H$_{18}$N$_2$O$_2$; C, 74.49; H, 5.92; N, 9.14.

2-(4-Hydroxyphenyl)-6-dimethylaminoquinolin-4-one (142) was obtained from 121, using the same synthetic procedure as for 134. The crude product was purified by column chromatography (silica gel, CHCl$_3$:MeOH=25:1) to give 142 as yellow solid. Yield: 74.2%; mp 321-323° C.; MS (EI, 70 eV): m/z 280.1 (M$^+$); IR (KBr): 1617.38 (C=O), 3132.53 (—NH) cm$^{-1}$; $^1$H-NMR (DMSO-d$_6$, 200 MHz) δ 3.03 (s, 6H), 7.01 (d, J=8.6 Hz, 2H), 7.08 (d, J=2.8 Hz, 1H), 7.40 (d, J=6.0 Hz, 1H), 7.64 (dd, J=9.4, 2.6 Hz, 1H), 7.84 (d, J=8.8 Hz, 2H), 8.22 (d, J=9.4 Hz, 1H), 11.30 (hr, 1H), 14.35 (br, 1H); Anal. Calcd for C$_{17}$H$_{16}$N$_2$O$_2$; C, 72.84; H, 5.75; N, 9.99.

2-(4-Hydroxy-3-methoxyphenyl)-6-morpholinoquinolin-4-one (143) was obtained from 122, using the same synthetic procedure as for 134. The crude product was purified by column chromatography (silica gel, CHCl$_3$:MeOH=25:1) to give 143 as yellow solid. (0.15 g, 0.3 mmol). Yield: 63.0%; mp 297-299° C.; MS (EI, 70 eV): m/z 352.1 (M$^+$); $^1$H-NMR (DMSO-d$_6$, 200 MHz) δ 3.15 (m, 4H), 3.77 (m, 4H), 3.88 (s, 3H), 6.28 (s, 1H), 6.92 (d, J=8.2 Hz, 1H), 7.27 (dd, J=8.2, 1.8 Hz, 1H), 7.33 (d, J=1.8 Hz, 1H), 7.43 (d, J=2.6 Hz, 1H), 7.47 (dd, J=8.8, 2.6 Hz, 1H), 7.67 (d, J=8.8 Hz, 1H), 9.60 (s, 1H), 11.40 (s, 1H); $^{13}$C-NMR (DMSO-d$_6$, 50 MHz) δ 176.85, 149.22, 148.29, 147.75, 137.15, 134.84, 125.98, 125.64, 122.71, 120.63, 120.00, 116.13, 111.65, 107.50, 105.68, 66.55, 56.31, 49.37; Anal. Calcd for C$_{20}$H$_{20}$N$_2$O$_4$; C, 68.17; H, 5.72; N, 7.95.

2-(4-Hydroxy-3-methoxyphenyl)-6-pyrrolidinoquinolin-4-one (144) was obtained from 123, using the same synthetic procedure as for 134. The crude product was purified by column chromatography (silica gel, CHCl$_3$:MeOH=25:1) to give 144 as yellow solid. Yield: 63.7%; mp 310-312° C.; MS (EI, 70 eV): m/z 336.2 (M$^+$); IR (KBr): 1605.81 (C=O), 3163.39 (—NH) cm$^{-1}$; $^1$H-NMR (DMSO-d$_6$ 200 MHz) δ 2.04 (m, 4H), 3.25 (m, 4H), 3.85 (s, 3H), 6.19 (s, 1H), 6.89 (d, J=8.2 Hz, 1H), 6.98 (d, J=2.6 Hz, 1H), 7.03 (dd, J=8.2, 2.6 Hz, 1H), 7.22 (dd, J=8.8, 2.6 Hz, 1H), 7.30 (d, J=2.6 Hz, 1H), 7.61 (d, J=8.8 Hz, 1H), 9.53 (s, 1H), 11.27 (s, 1H); Anal. Calcd for C$_{20}$H$_{20}$N$_2$O$_3$; C, 71.41; H, 5.99; N, 8.33.

Dibenzyl 3-(4-oxo-6-(pyrrolidin-1-yl)-1,4-dihydroquinolin-2-yl)phenyl phosphate (146). To a stirred solution of 138 (0.61 g, 2.0 mmol) in dry THF (20 mL) was added NaH (500 mg, 12.5 mmol) at 0±1° C. After the mixture was stirred for 1 h, tetrabenzyl pyrophosphate (46) (2.15 g, 4.0 mmol) was added and stirring was continued for 30 min. The reaction mixture was filtered and washed with CH$_2$Cl$_2$. The filtrate was concentrated under vacuum at a temperature below 30° C. to give crude product (145). Then, the crude product in anhydrous MeOH (50 mL) was stirred at 25° C. for 24 h. The precipitates were collected and purified by column chromatography (SiO$_2$, CH$_2$Cl$_2$: EtOAc=3:7) to give 146 (0.37 g, 0.65 mmol). Yellow solid; yield: 32.7%; mp 169-171° C.; MS (ESI): m/z 567.4 (M+H)$^+$; $^1$H-NMR (CDCl$_3$, 200 MHz): δ 1.97 (m, 4H), 3.27 (m, 4H), 5.04 (s, 2H), 5.09 (s, 2H), 6.39 (s, 1H), 6.93 (dd, J=9.0, 2.6 Hz, 1H), 7.05 (d, J=7.8 Hz, 1H), 7.19-7.46 (m, 14H), 7.52 (d, J=8.8 Hz, 1H); Anal. (C$_{33}$H$_{31}$N$_2$O$_5$P)C, H, N.

3-(4-Oxo-6-(pyrrolidin-1-yl)-1,4-dihydroquinolin-2-yl) phenyl dihydrogen phosphate (147). A suspension of 146 (200 mg, 0.36 mmol) in anhydrous MeOH (10 mL) was hydrogenated in the presence of 10% Pd/C (100 mg) at 25° C. for 20 min. The catalyst and precipitate were collected and dissolved in 10% NaHCO$_3$ solution and then filtered. The filtrate was acidified with dil aq HCl and the precipitate was then collected and washed with acetone to give 147 (97 mg, 0.25 mmol). Yellow solid; yield: 69.8%; mp>300° C.; MS (ESI): m/z 387.1 (M+H)$^+$; $^1$H-NMR (D$_2$O+NaOD, 200 MHz): δ 1.78 (m, 4H), 3.08 (m, 4H), 6.70 (s, 1H), 7.12-7.20 (m, 3H), 7.28 (t, J=7.8 Hz, 1H), 7.40 (d, J=7.6 Hz, 1H), 7.49 (s, 1H), 7.61 (d, J=9.8 Hz, 1H); Anal. (C$_{19}$H$_{19}$N$_2$O$_5$P) C, H, N.

II-2. Anticancer Activity

In Vitro Test

HL-60, Hep 3B, H460, MES-SA, MES-SAID x5 and Detroit 551 cells were treated with vehicle or test compounds for 48 h. The cell growth rate was determined by MTT (3-(4,5-dimethyl-thiazol-2-yl)-2,5-diphenyltetrazoliun bromide) reduction assay. After 48 h incabution, the cell growth rate was measured by scanning with an ELISA reader with a 570 nm filter and the IC$_{50}$ values of test compounds were calculated.

Results

The B-1 series of compounds has the following formula:

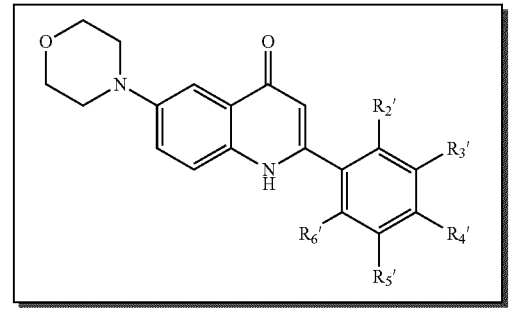

Table 2 shows the B-1 series of compounds inhibited proliferation of human cancer cells.

TABLE 2

| Cpd | R$_2$' | R$_3$' | R$_4$' | R$_5$' | IC$_{50}$(μM) HL-60 | Hep 3B | H460 | MES-SA | MES-SA/Dx5 | Ratio Of SA/Dx5 | Detroit 551 |
|---|---|---|---|---|---|---|---|---|---|---|---|
| 124 | OCH$_2$O | | H | H | 0.72 | 1.5 | 2.13 | 2.35 | 2.1 | 0.89 | >2.5 |
| 126 | OCH$_3$ | OCH$_3$ | H | H | 5.22 | 9.8 | 17.45 | 5.0 | 17.465 | 3.49 | >50 |
| 128 | OCH$_3$ | H | H | OCH$_3$ | 1.2 | 3.11 | 3.47 | 2.03 | 8.205 | 4.04 | 16.6 |
| 130 | OCH$_3$ | H | H | H | 2.48 | NA | 7.36 | 2.5 | 9.708 | 3.88 | >20 |
| 132 | H | H | OCH$_3$ | H | >2.5 | >2.5 | >2.5 | NA | NA | NA | >2.5 |
| 134 | OH | H | H | H | 2.1 | 8.78 | 8.3 | 2.38 | 10.419 | 4.38 | >100 |
| 137 | H | OH | H | H | 0.23 | 11.5 | 24.8 | 3.61 | 7.3 | 2.02 | 10 |
| 140 | H | H | OH | H | 1.64 | >10 | >10 | NA | NA | NA | >10 |
| 143 | H | OCH$_3$ | OH | H | 3.9 | 50 | 50 | NA | NA | NA | 50 |
| 143a | OCH$_3$ | H | H | OH | 93.8 | >100 | 84.8 | NA | NA | NA | >100 |
| 143b | OH | H | H | OH | 56.2 | 59.32 | >100 | NA | NA | NA | >100 |

*: Cancer cell were treated with test compound for 48 hrs.

The B-2 series of compounds has following formula:

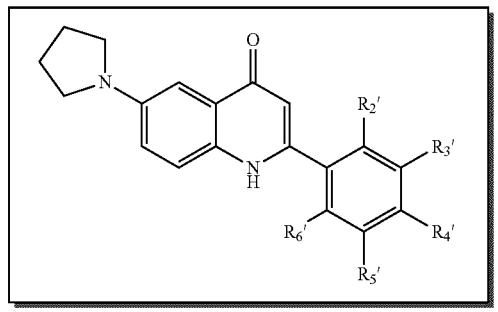

Table 3 shows a the B-2 series of compounds inhibited proliferation of human cancer cells.

TABLE 3

| Cpd. | R$_2$' | R$_3$' | R$_4$' | R$_5$' | IC$_{50}$(μM) HL-60 | Hep 3B | H460 | MES-SA | MES-SA/Dx5 | Ratio Of SA/Dx5 | Detroit 551 |
|---|---|---|---|---|---|---|---|---|---|---|---|
| 125 | OCH$_2$O | | H | H | 0.08 | 0.2 | 0.2 | 0.1 | 0.183 | 1.83 | >2.5 |
| 127 | OCH$_3$ | OCH$_3$ | H | H | 0.53 | 1.2 | 1.78 | 0.802 | 1.71 | 2.13 | >20 |
| 129 | OCH$_3$ | H | H | OCH$_3$ | 0.006 | 0.22 | 0.19 | 0.229 | 0.216 | 0.94 | 5.0 |
| 131 | OCH$_3$ | H | H | H | 0.13 | 0.3 | 0.57 | 0.445 | 0.451 | 1.01 | >10 |
| 133 | H | H | OCH$_3$ | H | >1.0 | >1.0 | >1.0 | NA | NA | NA | >1.0 |
| 135 | OH | H | H | H | 0.36 | 1.31 | 0.86 | 0.846 | 1.0 | 1.18 | 25 |
| 138 | H | OH | H | H | 0.009 | 0.28 | 0.4 | 0.734 | 0.32 | 0.23 | 1.39 |
| 141 | H | H | OH | H | 0.04 | 1.1 | 1.56 | NA | NA | NA | >25 |
| 144 | H | OCH$_3$ | OH | H | 0.038 | 0.38 | 0.56 | NA | NA | NA | >2.5 |
| 144a | OCH$_3$ | H | H | OH | 1.62 | 7.38 | 6.5 | 3.69 | 25 | 6.78 | 9.1 |
| 144b | OH | H | H | OH | NA | NA | NA | NA | NA | NA | NA |

*: Cancer cell were treated with test compound for 48 hrs.

The B-3 series of compounds has the following formula:

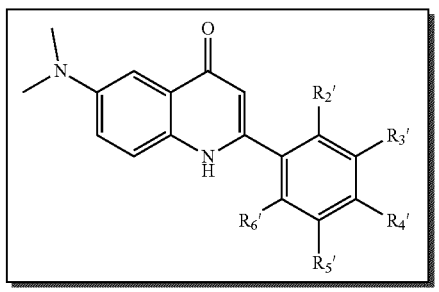

Table 4 shows the B-3 series of compounds inhibited proliferation of human cancer cells.

TABLE 4

| | | | | | | | IC$_{50}$(μM) | | | |
|---|---|---|---|---|---|---|---|---|---|---|
| Cpd. | R$_2$' | R$_3$' | R$_4$' | R$_5$' | HL-60 | Hep 3B | H460 | MES-SA | MES-SA/Dx5 | Ratio Of SA/Dx5 | Detroit 551 |
| 136 | OH | H | H | H | 3.02 | 7.1 | 5.4 | NA | NA | NA | 100 |
| 139 | H | OH | H | H | 0.06 | 1.0 | 6.2 | 0.931 | 0.852 | 0.92 | 10 |
| 142 | H | H | OH | H | 0.64 | 9.0 | 0.56 | NA | NA | NA | 75 |

*: Cancer cell were treated with test compound for 48 hrs.

In vivo antitumor activity assay

The Hep-3D tumor cell line was purchased from American Type Culture Collection (ATCC HB-8064, human hepatocellular carcinoma cells). A culture medium of 90% DMEM, 10% Fetal Bovine Serum, supplemented with 1% penicillin-streptomycin, was used. The tumor cells were incubated in an atmosphere containing 5% CO$_2$ at 37° C.

In vivo antitumor activity assay

The Hep-3B tumor cell line was purchased from American Type Culture Collection (ATCC HB-8064, human hepatocellular carcinoma cells). A culture medium of 90% DMEM, 10% Fetal Bovine Serum, supplemented with 1% penicillin-streptomycin, was used. The tumor cells were incubated in an atmosphere containing 5% CO$_2$ at 37° C.

Balb/c Nude mice used in this stud were male, 4-6 weeks age, weighing 18-20 g and provided by National Animal Center. All animals were housed in individually ventilated cages racks (IVC Racks, 36 Mini Isolator system) under specific pathogen-free (SPF) conditions throughout the experiment. Each cage (in cm, 26.7 length×20.7 width×14.0 height) was sterilized with autoclave and contained eight mice. The animals were maintained in a hygienic environment under controlled temperature (20-24° C.) and humidity (40% -70%) with a 12 hour light/dark cycle. The animals were given free access to sterilized lab chow and sterilized distilled water ad libitum. All aspects of this work, i.e., housing, experimentation and disposal of animals, were performed in general accordance with the Guide for the Care and Use of Laboratory Animals (National Academy Press, Washington, D.C., 1996).

In the xenograft tumor model of human hepatocellular carcinoma cell lines (Hep-3B, ATCC HB-8064) in male Balb/c Nude mice, compound 147 prepared in 9% (w/v) NaHCO$_3$ solution at doses of 7.5, 15 and 30 mg/kg -i.v.or p.o., qd) was administered five days per week for four consecutive weeks and ceased at Day 28. The tumor size and body weight were monitored and recorded for 28 days. Human hepatocellular carcinoma cells (HEP-3, ATCC HB-8064) with 2 ×10$^6$ cells in 0.1 mL were injected subcutaneously into the right flank of the mice. When the tumor growth reached >100 mm$^3$ in volume (assumed as day 0), the tumor-bearing animals were assigned into several groups (six animals in each group) for study.

The body weight and tumor size were measured and recorded every seven days during the experiment periods of 28 days. Tumor volume (mm$^3$) was estimated according to the formula of length ×(width)$^2$×0.5 in mm$^3$. Tumor growth inhibition was calculated as T/C (treatment/control) by the following formula: T/C=(Tn—To)/(Cn—Co)×100% (To: Tumor volume of treated group in Day 0; Tn: Tumor volume of treated group in Day n; Co: Tumor volume of control group in Day 0; Cn: Tumor volume of control group in Day n).

Results

Figure 6A:
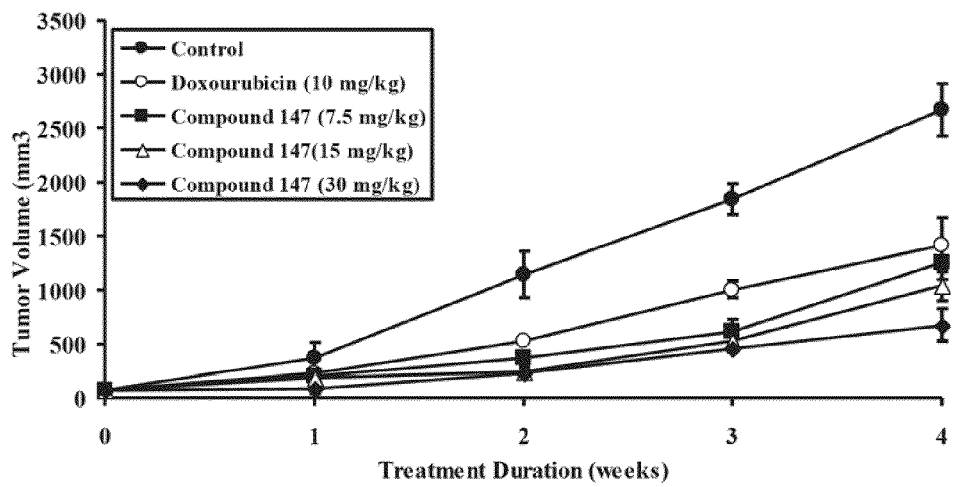
FIGS. 6A-6C show (A) Mean tumor volume-time profiles (B) Mean tumor weight-time profiles (C) Mean body weight-time profiles in Hep3B xenograft nude mice (n=6) following po dosing of doxorubicin at 10 mg/kg and 147 at 7.5, 15, and 30 mg/kg five days per week for four consecutive weeks.
Figure 6B:
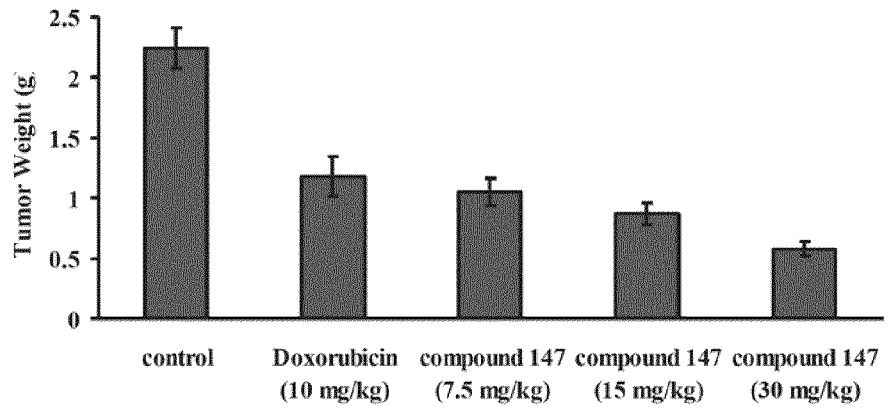
Figure 6C:
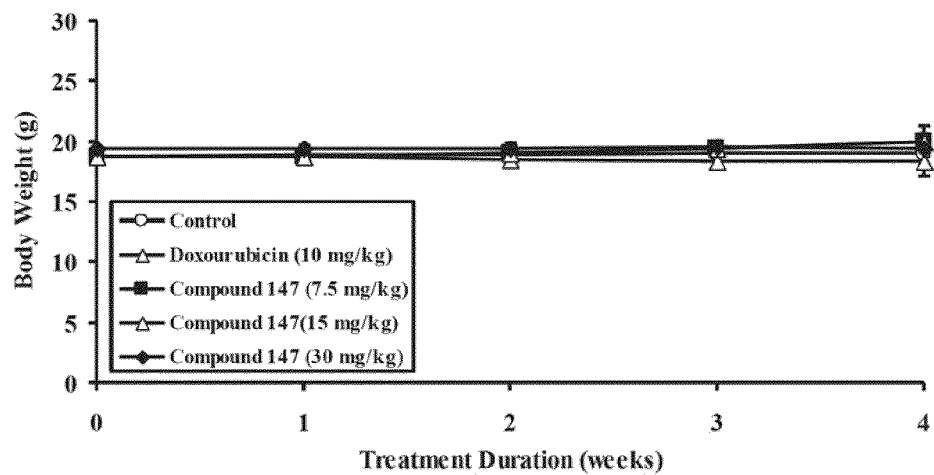
Figure 7A:
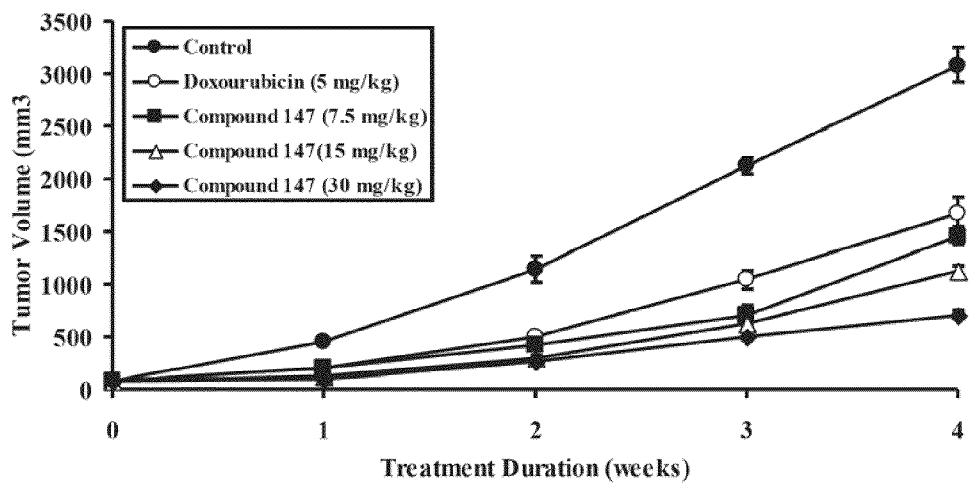
FIGS. 7A-7C show (A) Mean tumor volume-time profiles (B) Mean tumor weight-time profiles (C) Mean body weight-time profiles in Hep3B xenograft nude mice (n=6) following iv dosing of doxorubicin at 10 mg/kg and 147 at 7.5, 15, and 30 mg/kg five days per week for four consecutive weeks.
Figure 7B:
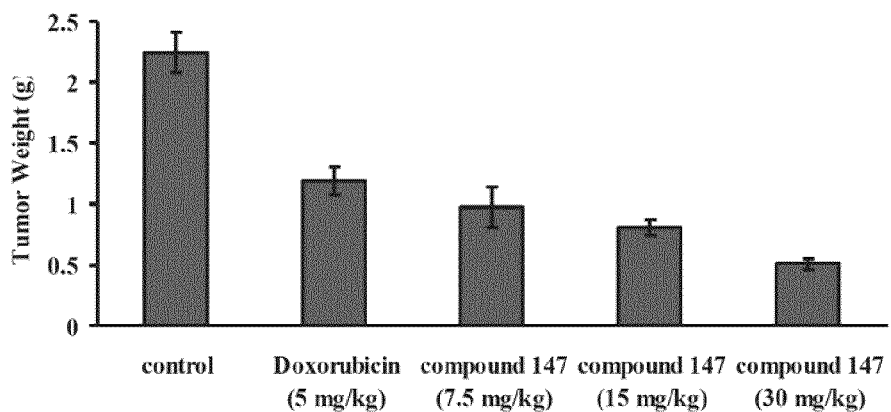
Figure 7C:
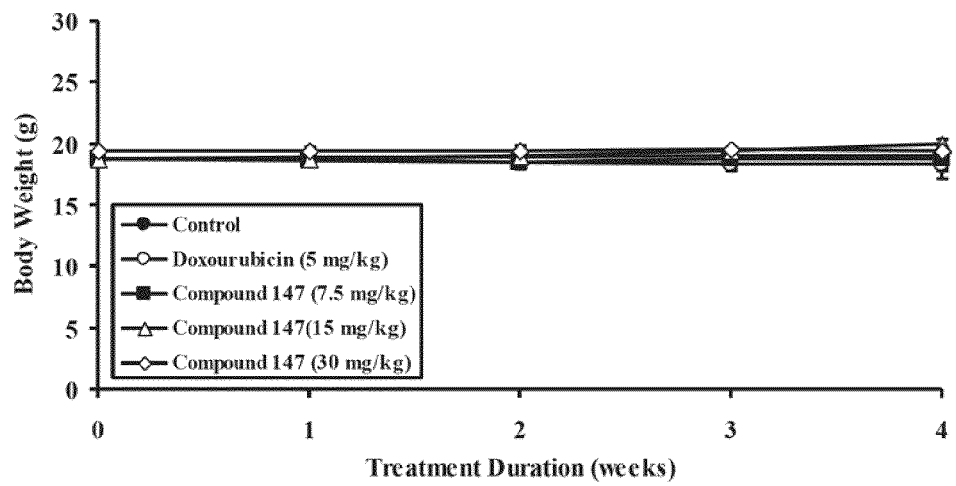

The monophosphate (147) of 138 was evaluated in the Hep3B xenograft nude mice model by oral route (p.o.),at dosages of 7.5, 15 and 30 mg/kg/day. As shown by the results in FIG. 6 (A-C), compound 147 induced dose- and time-dependent inhibition of Hep3B tumor growth. At the 7.5 mg/kg dose, the Hep3B inhibitory activity of 147 was found to exceed that of 10 mg/kg doxorubicin, and at the 30 mg/kg dose of 147, the weight of Hep3B tumor was reduced to 26.3% of that of the control (FIG. 6B). During the course of antitumor evaluation, no significant body weight changes were detected in either the tested or the control group (FIG. 6C). Comparison of the antitumor activity of 147 administered through two different routes showed that the i.v route yielded slightly greater activity than the p.o. route (FIGS. 7A-7C).

III. C Series

Chemical Synthesis

The synthetic procedure of target compounds 153 is illustrated in Scheme 11. The starting 2-amino-4,5-methylenedioxy-acetophenone (148) was first reacted with naphthalene-1-carbonyl chloride (149) to give N-(6-Acetyl-1,3-benzodioxol-5-yl)naphthalene-1-carboxamide (150). Then, the intermediate (150) was subjected to cyclization in dioxane, in the presence of NaOH, to afford 2-(1-Naphthalenyl)-6,7-methylenedioxyquinolin-4-one (151). Compound 151 was first reacted with tetrabenzylpyrophosphate in THF, in the presence of NaH, to yield Dibenzyl 2-(1-naphthalenyl)-6,7-methylenedioxyquinolin-4-yl Phosphate (152). Compound 152 was then subjected to catalytic hydrogenation in MeOH to give its diphosphoric acid (153).

The synthetic procedure of target compounds 158 is illustrated in Scheme 12. The starting 2-amino-4,5-methylenedioxy acetophenone (148) was first reacted with benzo[b]furan-3-carbonyl chloride (154) to give N-(6-Acetyl-1,3-benzodioxol-5-yl)-1-benzofuran-3-carboxamide (155). Then, the intermediates (155) was subjected to cyclization in dioxane, in the presence of NaOH, to afford 2-(3-Benzo[b]

furyl)-6,7-methylenedioxyquinolin-4-one (156). Compound 156 was first reacted with tetrabenzylpyrophosphate in THF, in the presence of NaH, to yield dibenzyl 2-(3-benzo[b]furyl)-6,7-methylenedioxyquinolin-4-yl phosphate (157). Compound 157 was then subjected to catalytic hydrogenation in MeOH to give its diphosphoric acid (158).

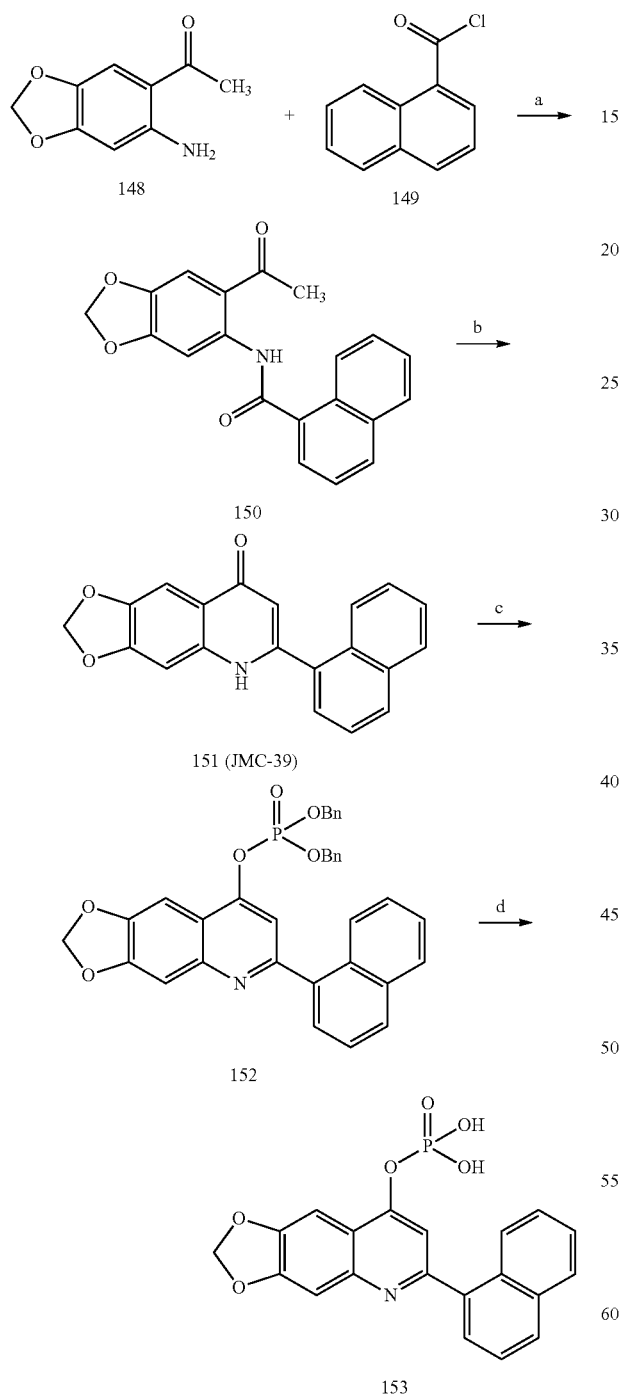

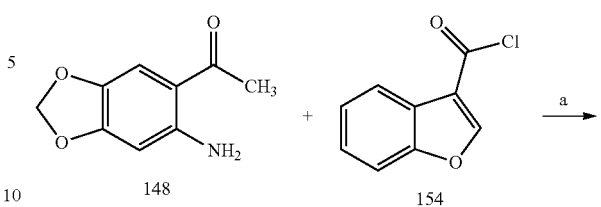

Reagents and conditions: (a) toluene/triethylamine, 22-25° C.; (b) t-BuOK/t-BuOH, reflux; (c) tetrabenzyl pyrophosphate, NaH/THF; (d) H$_2$, Pd/C, MeOH Reagents and conditions: (a) toluene/triethylamine, 22-25° C.; (b) t-BuOK/t-BuOH, reflux; (c) tetrabenzyl pyrophosphate, NaH/THF; (d) H$_2$, Pd/C, MeOH

EXAMPLES

General Experimental Procedures. All of the reagents and solvents were obtained commercially and used without further purification. Reactions were monitored by thin-layer chromatography, using Merck plates with fluorescent indicator (TLC Silica gel 60 F$_{254}$). The following adsorbent was used for column chromatography: silica gel 60 (Merck, particle size 0.063-0.200 mm). Melting points were determined on a Yanaco MP-500D melting point apparatus and were uncorrected. IR spectra were recorded on Shimadzu IRPrestige-21 spectrophotometers as KBr pellets. NMR spectra were obtained on a Bruker Avance DPX-200 FT-NMR spectrometer in $CDCl_3$ or DMSO. The following abbreviations are used: s, singlet; d, doublet; t, triplet; q, quartet; dd, double doublet and m, multiplet. EI-MS spectra were measured with an HP 5995 GC-MS instrument. ESI-MS spectra were measured with a Finnigan LCQ ion-trap mass spectrometer (TSQ Quantum, Thermo Finnigan Corporation, San Jose, Calif.). Elemental analyses (C, H, and N) were performed on a Perkin-Elmer 2400 Series II CHNS/O analyzer, and the results were within ±0.4% of the calculated values.

N-(6-Acetyl-1,3-benzodioxol-5-yl)naphthalene-1-carboxamide (150). Into solutions of 149 (5.0 mmol) in 200 mL of dry toluene were added triethylamine (4 mL) and 2-amino-4,5-methylenedioxy acetophenone (148) (5 mmol). The mixtures were stirred at 20±2° C. for 24 h and then evaporated. The residues were washed with acetone and EtOH and then recrystallized from acetone or EtOH to form 150. Obtained as a grayish-white solid; mp 143-144° C.; ESI-MS (Positive mode): m/z 334 $[M+H]^+$; $^1$H-NMR (400 MHz, DMSO-$d_6$, δ): 2.59 (3H, s), 6.20 (2H, s), 7.60-7.68 (4H, m), 7.87 (1H, d, J=7.2 Hz), 8.05-8.07 (1H, m), 8.15 (1H, d, J=8.0 Hz), 8.33-8.38 (2H, m), 12.52 (1H, s); IR (KBr): 1647, 1672 (C=O) $cm^{-1}$.

2-(1-Naphthalenyl)-6,7-methylenedioxyquinolin-4-one (151). Into a suspension of 150 (2.95 mmol) in t-butyl alcohol (100 mL) was added potassium t-butoxide (1.66 g, 14.7 mmol). The mixture was refluxed under argon for 12 h, cooled, and poured into a 10% ammonium chloride solution (100 mL). The solid precipitate was collected and washed with EtOH. The crude product was purified by flash chromatography (silica gel, $CH_2Cl_2$:EtOH 16:1-10:1). Yield 52% from 150 as a grayish-white solid; mp>350° C.; ESI-MS (Positive mode): m/z 316 $[M+H]^+$; $^1$H-NMR (DMSO-$d_6$, δ): 6.08 (1H, s), 6.15 (2H, s), 7.03 (1H, s), 7.46 (1H, s), 7.56-7.63 (2H, m), 7.63-7.70 (2H, m), 7.83 (1H, d, J=7.6 Hz), 8.06 (1H, d, J=7.6 Hz), 8.11 (1H, d, J=7.6 Hz), 11.90 (1H, s). IR (KBr): 1653 (C=O) $cm^{-1}$; Anal. Calcd for $C_{20}H_{13}NO_3$: C, 76.18; H, 4.16; N, 4.44. Found: C, 75.60; H, 3.94; N, 4.29.

Dibenzyl 2-(1-naphthalenyl)-6,7-methylenedioxyquinolin-4-yl Phosphate (152). A suspension of 151 (1.20 g, 3.81 mmol) in anhydrous MeOH (10 mL) was stirred at 25° C. for 24 h. The precipitates were collected and purified by silica gel column chromatography eluted by n-hexane and EtOAc to give 152. Orange oil; yield: 63.7%; ESI-MS (Positive mode): nil: 576 $[M+H]^+$; $^1$H-NMR ($CDCl_3$. 500 MHz): δ 5.21 (4H, dd, J=8.30, 8.15 Hz), 6.17 (2H, s), 7.23 (1H, s), 7.28-7.37 (9H, m), 7.40-7.60 (7H, m), 7.95 (2H, m), 8.09 (1H, d, J=8.20 Hz).

2-(1-Naphthalenyl)-6,7-methylenedioxyquinolin-4-yl Dihydrogen Phosphate (153). A suspension of 152 (894.8 mg, 1.55 mmol) in anhydrous MeOH (40 mL) was hydrogenated in the presence of 10% Pd/C (456.7 mg) at 25° C. for 15 min. The catalyst and precipitate were collected and dissolved in 10% $NaHCO_3$ solution and then filtered. The filtrate was acidified with dil aq HCl and the precipitate was then collected and washed with acetone to give 153. Yellow solid; yield: 94.1%; ESI-MS (Negative mode): m/z 394 $[M-H]^-$; $^1$H-NMR ($D_2O$+NaOD, 500 MHz): δ 6.13 (2H, s), 7.26 (1H, s), 7.50 (1H, ddd, J=8.23, 7.33, 1.20 Hz), 7.55-7.58 (2H, m), 7.62-7.70 (3H, m), 7.98 (1H, d, J=8.53 Hz), 8.02 (1H, d, J=8.96 Hz); $^{13}$C-NMR ($D_2O$+NaOD, 125 MHz): δ 98.65, 102.15, 103.54, 109.80, 110.00, 118.35, 125.66, 126.37, 126.84, 127.40, 128.34, 128.97, 130.89, 133.50, 138.15, 146.58, 147.34, 151.27, 158.15, 158.23.

N-(6-Acetyl-1,3-benzodioxol-5-yl)-1-benzofuran-3-carboxamide (155). Into solutions of 154 (5.0 mmol) in 200 mL of dry toluene were added triethylamine (4 mL) and 2-amino-4,5-methylenedioxy acetophenone (148) (5 mmol). The mixtures were stirred at 20±2° C. for 24 h and then evaporated. The residues were washed with acetone and EtOH and then recrystallized from acetone or EtOH to form 155. Obtained as a pale-yellow solid; mp 144-145° C.; ESI-MS (Positive mode): m/z 324 $[M+H]^+$; $^1$H-NMR (400 MHz, DMSO-$d_6$): δ 2.63 (3H, s), 6.19 (2H, s), 7.41-7.50 (21-1, m), 7.68 (1H, s), 7.75 (1H, dd, J=1.6, 6.8 Hz), 8.15 (1H, dd, J=2.0, 8.8 Hz), 8.27 (1H, s), 8.71 (1H, s), 12.63 (1H, s); IR (KBr): 1635, 1677 (C=O) $cm^{-1}$.

2-(3-Benzo[b]furyl)-6,7-methylenedioxyquinolin-4-one (156). Into a suspension of 155 (2.95 mmol) in t-butyl alcohol (100 mL) was added potassium t-butoxide (1.66 g, 14.7 mmol). The mixture was refluxed under argon for 12 h, cooled, and poured into a 10% ammonium chloride solution (100 mL). The solid precipitate was collected and washed with EtOH. The crude product was purified by flash chromatography (silica gel, $CH_2Cl_2$: EtOH 16:1-10:1). Obtained as a pale-yellow solid from 155; yield 17%; mp>315° C.; ESI-MS (Positive mode): m/z 306 $[M+H]^+$; $^1$H-NMR (400 MHz, DMSO-$d_6$): δ 6.12 (2H, s), 6.49 (1H, s), 7.13 (1H, s), 7.36-7.45 (3H, m), 7.69 (1H, d, J=8.0 Hz), 8.14 (1H, s), 8.52 (1H, s); IR (KBr): 1626 (C=O) $cm^{-1}$; Anal. Calcd for $C_{18}H_{11}NO_4$: C, 70.82; H, 3.63; N, 4.59. Found: C, 70.52; H, 3.95; N, 4.21.

Dibenzyl 2-(3-benzo[b]furyl)-6,7-methylenedioxyquinolin-4-yl Phosphate (157). To a stirred solution of 151 (0.04 g, 0.13 mmol) in dry tetrahydrofuran (40 mL) was added NaH 60% in mineral oil (48.0 mg, 2.0 mmol) at 0±1° C. After the mixture was stirred for 1 h, tetrabenzyl pyrophosphate (139.8 mg, 0.26 mmol) was added and stirring was continued for 60 min. The reaction mixture was filtered and washed with tetrahydrofuran. The filtrate was concentrated under vacuum at a temperature below 30° C. The residue was purified by column chromatography ($SiO_2$, n-hexane/EtOAc) to give 157. Obtained as a white solid from 156; yield: 86.8%; ESI-MS (Positive mode): m/z 566 $[M+H]^+$; $^1$H-NMR (500 MHz. $CDCl_3$): δ 5.24 (4H, dd, J=9.5, 9.5 Hz), 6.15 (2H, s), 7.16 (1H, s), 7.34-7.42 (12H, m), 7.45 (1H, s), 7.58 (1H, d, J=7.5 Hz), 7.59 (1H, s), 8.02 (1H, s), 8.47 (1H, d, J=7.5 Hz); $^{13}$C-NMR ($D_2O$+NaOD, 125 MHz): δ 70.67, 70.63, 97.30, 100.00, 101.87, 105.93, 106.72, 111.48, 116.94, 121.76, 122.62, 123.51, 124.82, 125.66, 128.20, 128.72, 128.96, 134.98, 144.59, 147.92, 148.43, 150.97, 151.43, 153.47, 156.06.

2-(3-Benzo[b]furyl)-6,7-methylenedioxyquinolin-4-yl Dihydrogen Phosphate (158). A suspension of 157 (80.1 mg, 0.14 mmol) in anhydrous MeOH (40 mL) was hydrogenated in the presence of 10% Pd/C (40.0 mg) at 25° C. for 15 min. The catalyst and precipitate were collected and dissolved in 10% $NaHCO_3$ solution and then filtered. The filtrate was acidified with dil aq HCl and the precipitate was then collected and washed with acetone to give 158. Obtained as white solid; yield: 46.3%; ESI-MS (Positive mode): m/z 386 $[M+H]^+$, 408 $[M+Na]^+$; ESI-MS (Negative mode): m/z 384 $[M-H]^-$; $^1$H-NMR ($D_2O$+NaOD, 500 MHz): δ 6.12 (2H, s), 7.32 (1H, s), 7.42 (2H, m), 7.56 (1H, s), 7.63 (1H, d, J=8.0 Hz), 7.78 (1H, s), 8.29 (1H, d, J=7.0 Hz), 8.40 (1H, s).

III-2. Anticancer Activity
In Vitro Test
MTT (3-(4,5-Dimethylthiazol-2-yl)-2,5-diphenyltetrazolium bromide) assays. HL-60, HCT-116, A549, Hep 3B, KB, Kb-VIN and DU145 cells were treated with tested compounds for the indicated periods. After treatment, cells were washed once with PBS and incubated with MTT (Sigma, St. Louis, Mo., USA) for 2 h. The formazan precipitate was dissolved in 150 μL of DMSO, and the absorbance was measured with an ELISA reader at 570 nm.

Results

TABLE 5

IC$_{50}$ (μM) Values from In Vitro Cytotoxicity Testing of 151 and 156.

151 (JMC-39)

156 (JMC-37)

| Compound | HL-60 | HCT-116 | A549 | Hep 3B | KB | Kb-VIN | DU145 |
|---|---|---|---|---|---|---|---|
| 151 | 0.07 | 0.07 | 0.13 | 0.07 | 0.13 | 0.19 | 0.13 |
| 156 | 0.03 | 0.05 | 2.98 | 0.09 | 1.05 | 0.59 | 1.87 |

* Not assayed

Scheme 13

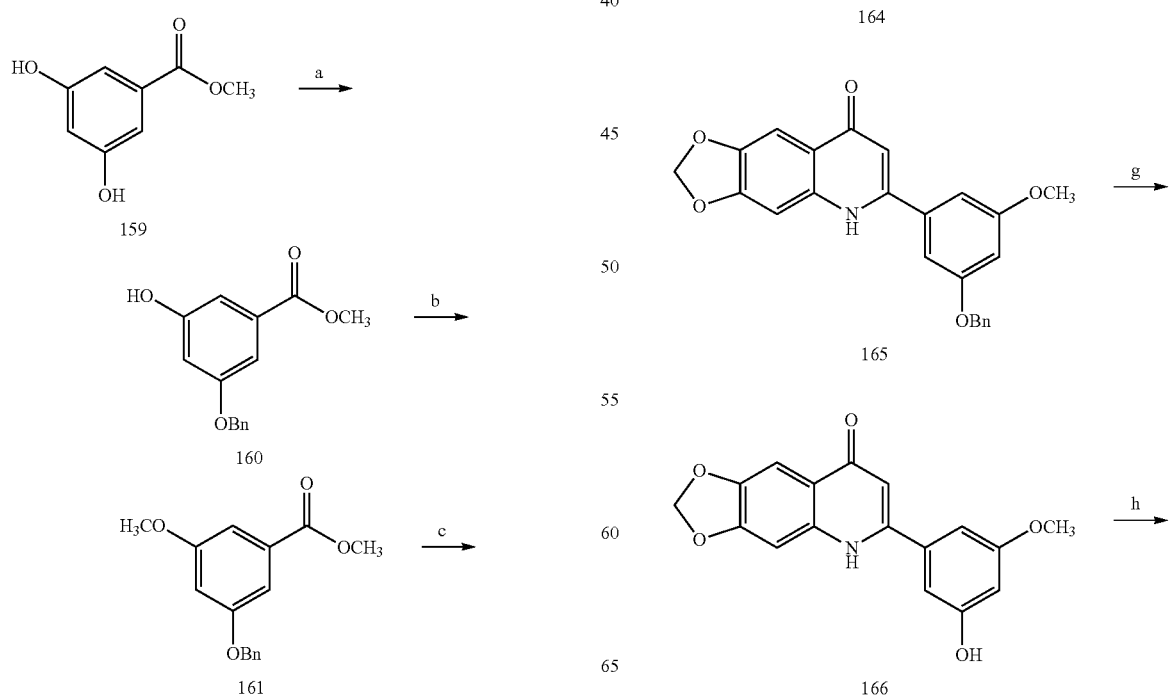

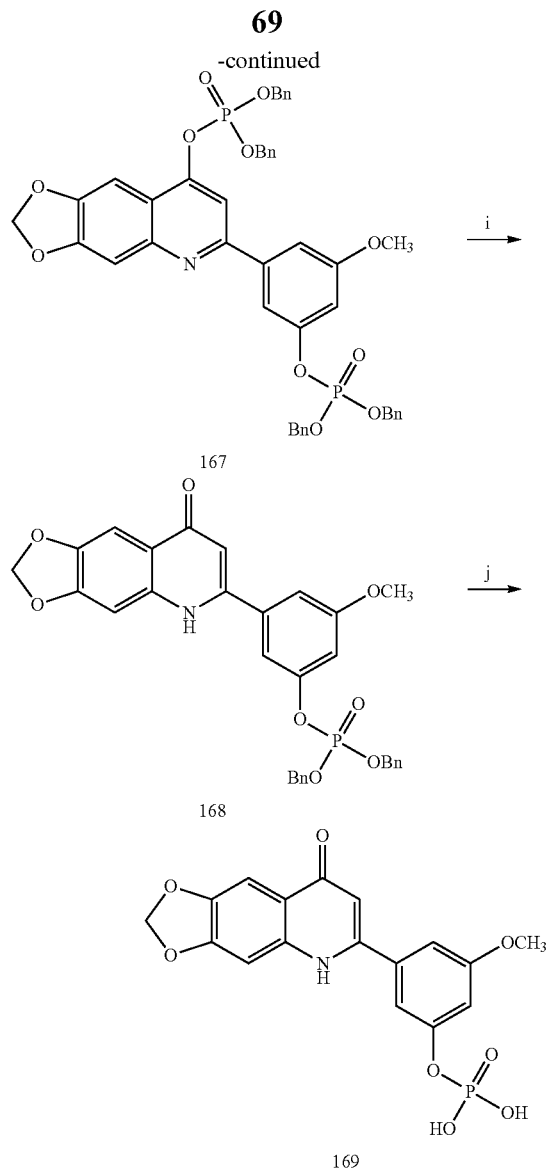

Reagents and conditions: (a) benzyl bromide, K$_2$CO$_3$, acetone; (b) iodomethane, K$_2$CO$_3$, acetone; (c) NaOH, H$_2$O, ethanol; (d) thionyl chloride, dimethyl formamide, toluene; (e) THF/triethylamine, 22-25° C.; (f) NaOH, 1,4-dioxane, reflux; (g) H2, Pd/C, MeOH; (h) tetrabenzyl pyrophosphate, NaH/THF; (i) MeOH, 48 hrs; (j) H2, Pd/C, MeOH IV. D Series
Chemical Synthesis The compound 159 was derived into a phosphate (169) following the synthetic method in Scheme 13. As illustrated, 3-(Benzyloxy)-5-methoxybenzoyl chloride (163) obtained from 159 with steps a-d was reacted with 2-amino-4,5-methylenedioxy acetophenone (148) in THF/triethylamine, to give N-(6-acetylbenzo[d][1,3]dioxol-5-yl)-3-(benzyloxy)-5-methoxybenzamide (164). Compound 164 was further refluxed in NaOH/1,4-dioxane to yield 165. Subsequently, by following the steps g-j, target compound 169 was afforded as white solid.

EXAMPLES

General Experimental Procedures. All of the reagents and solvents were obtained commercially and used without further purification. Reactions were monitored by thin-layer chromatography, using Merck plates with fluorescent indicator (TLC Silica gel 60 F$_{254}$). The following adsorbent was used for column chromatography: silica gel 60 (Merck, particle size 0.063-0.200 mm). Melting points were determined on a Yanaco MP-500D melting point apparatus and were uncorrected. IR spectra were recorded on Shimadzu IRPrestige-21 spectrophotometers as KBr pellets. NMR spectra were obtained on a Bruker Avance DPX-200 FT-NMR spectrometer in CDCl$_3$ or DMSO. The following abbreviations are used: s, singlet; d, doublet; t, triplet; q, quartet; dd, double doublet and m, multiplet. EI-MS spectra were measured with an HP 5995 GC-MS instrument. ESI-MS spectra were measured with a Finnigan LCQ ion-trap mass spectrometer (TSQ Quantum, Thermo Finnigan Corporation, San Jose, Calif.). Elemental analyses (C, H, and N) were performed on a Perkin-Elmer 2400 Series II CHNS/O analyzer, and the results were within ±0.4% of the calculated values.

Methyl 3-(benzyloxy)-5-hydroxybenzoate (160)

A mixture of 8.40 g (0.05 mmol) methyl 3,5-dihydroxybenzoate (159) and 7.60 g (0.055 mmol) of potassium carbonate in 250 mL of acetone was stirred at room temperature for 30 min. Then 8.55 g (0.05 mmol) of benzyl bromide dissolved in 100 mL of acetone was added. The suspension was refluxed for 24 h. The solid was filtered, and the filtrate was evaporated. The residue was purified by column chromatography (SiO$_2$, CH$_2$Cl$_2$/EtOAc=9/1) to give 160.

Obtained as a white solid from methyl 3,5-dihydroxybenzoate (159); yield 34%; $^1$H NMR (400 MHz, CDCl$_3$): δ3.92 (3H, s), 5.05 (2H, s), 6.77 (1H, dd, J=2.35, 2.20 Hz), 7.13 (1H, s), 7.27-7.28 (2H, m), 7.34-7.45 (5H, m); $^{13}$C-NMR (50 MHz, CDCl$_3$): δ 52.34, 70.27, 107.44, 108.08, 109.48, 127.53 (2C), 128.11, 128.60 (2C), 131.99, 136.41, 137.45, 156.80, 160.00.

Methyl 3-(benzyloxy)-5-methoxybenzoate (161)

A suspension of 4.0 g (0.0165 mmol) methyl 3-(benzyloxy)-5-hydroxybenzoate (160), 6.84 g (0.0495 mmol) potassium carbonate, and 11.71 g (0.0825 mmol) iodomethane in the 200 mL of acetone was stirred at room temperature for 24 h. After the mixture was filtered and evaporated, the residue was washed with water. The methyl 3-(benzyloxy)-5-methoxybenzoate (161) was obtained as a white solid.

Obtained as a white solid from methyl 3-(benzyloxy)-5-hydroxybenzoate (160); yield 85%; $^1$H NMR (200 MHz, CDCl$_3$): δ3.83 (3H, s), 3.92 (3H, s), 5.09 (2H, s), 6.74 (1H, t, J=2.45 Hz), 7.21 (1H, dd, J=2.45, 1.22 Hz), 7.29 (1H, dd, J=2.45, 1.22 Hz), 7.34-7.48 (5H, m); $^{13}$C-NMR (50 MHz, CDCl$_3$): δ 52.22, 55.55, 70.24, 106.53, 107.47, 107.98, 127.54, 128.09, 128.59, 131.99, 136.44, 159.75, 160.61.

3-(Benzyloxy)-5-methoxybenzoic acid (162)

4.45 g (0.0174 mmol) of methyl 3-(benzyloxy)-5-methoxybenzoate (161) was suspended in 120 mL of 95% ethanol and 5 mL water. An amount of 2.00 g (0.05 mmol) of sodium hydroxide was added. The mixture was heated at reflux for 1 h. After the mixture was evaporated, the residue was quenched with 150 mL of water. The solution was neutralized with dil aq HCl and then the precipitate was collected and washed with water and acetone to give 162.

Obtained as a white solid from methyl 3-(benzyloxy)-5-methoxybenzoate (161); yield 90%; $^1$H NMR (DMSO-d$_6$, 200 MHz): δ 3.81 (3H, s), 5.09 (2H, s), 6.74 (1H, t, J=2.45 Hz), 7.25 (1H, dd, J=2.45, 1.35 Hz), 7.20-7.46 (6H, m); $^{13}$C-NMR (DMSO-d$_6$, 50 MHz): δ 55.89, 69.94, 106.19, 107.57, 108.17, 128.12, 128.33, 128.90, 133.34, 137.22, 138.78, 159.88, 160.80, 167.36, 176.99.

3-(Benzyloxy)-5-methoxybenzoyl chloride (163)

3-(Benzyloxy)-5-methoxybenzoic acid (162) (2.57 g, 0.01 mmol) and thionyl chloride (4.80 g, 0.04 mmol) were suspended in 200 mL of dry toluene. The reaction mixture was stirred for 30 min and then dimethyl formamide (3 drops) was added. The mixture was stirred for 24 h and then evaporated to dryness. The residue was directly used for the next step without further purification.

N-(6-acetylbenzo[d][1,3]-dioxol-5-yl)-3-(benzyloxy)-5-methoxybenzamide (164)

Into solutions of 163 (2.77 g, 0.01 mmol) in 200 mL of dry tetrahydrofuran were added triethylamine (10 mL) and 2-amino-4,5-methylenedioxy acetophenone (148) (1.79 g, 0.01 mmol). The mixtures were stirred at room temperature for 24 h and then evaporated. The residue was purified by column chromatography ($SiO_2$, $CH_2Cl_2$/EtOAc=3/1) to give 164.

Obtained as a grayish white solid from 3-(benzyloxy)-5-methoxybenzoyl chloride (163) and 2-amino-4,5-methylenedioxy acetophenone (148); yield 75%; ESI-MS (Positive mode): m/z 442 $[M+Na]^+$; $^1$H NMR (DMSO-$d_6$, 500 MHz): δ2.64 (3H, s), 3.84 (3H, s), 5.20 (2H, s), 6.19 (2H, s), 6.87 (1H,$), 7.09 (1H, s), 7.16 (1H, s), 7.37 (1H, d, J=7.43 Hz), 7.43 (1H, t, J=7.43 Hz), 7.49 (1H, d, 7.43 Hz), 7.68 (1H, s), 8.34 (1H, s), 13.06 (1H, s); $^{13}$C-NMR (DMSO-$d_6$, 125 MHz): δ 29.32, 55.99, 70.12, 98.96, 100.77, 102.91, 105.03, 105.67, 106.45, 111.25, 116.53, 128.28, 128.30, 128.95, 136.90, 137.05, 138.27, 143.11, 152.68, 160.28, 161.20, 164.99, 200.00.

2-(3-Benzyloxy-5-methoxyphenyl)-6,7-methylenedioxyquinolin-4-one (165)

Into a suspension of 164 (3.33 g, 0.0079 mmol) in 200 mL of 1,4-dioxane was added sodium hydroxide (2.50 g, 0.0635 mmol). The mixture was refluxed for 24 h. After the reaction mixture was evaporated, 100 mL of 10% ammonium chloride solution was added. The mixture was stirred for 12 h, and then the precipitate was collected and washed with water and acetone.

Obtained as a grayish white solid; yield 75%; mp 235-238° C.; ESI-MS (Positive mode): m/z 402 $[M+H]^+$; ESI-MS (Negative mode): m/z 400 $[M-H]^-$; $^1$H NMR (DMSO-$d_6$, 500 MHz): δ 3.85 (3H, s), 5.22 (2H, s), 6.16 (2H, s), 6.31 (1H, s, br), 6.79 (1H, s), 6.95 (1H, s), 7.04 (1H, s), 7.21 (1H, s), 7.36-7.50 (6H, m), 11.50 (1H, s, br); $^{13}$C-NMR (DMSO-$d_6$, 125 MHz): δ 56.04, 70.10, 97.72, 101.76, 102.40, 103.14, 105.95, 106.60, 107.15, 110.00, 120.46, 128.25, 128.42, 128.96, 137.27, 137.82, 145.66, 151.57, 160.31, 161.23, 175.40.

2-(3-Hydroxy-5-methoxyphenyl)-6,7-methylenedioxyquinolin-4-one (166)

A suspension of 0.5 g (1.245 mmol) of 165 and 0.25 g of palladium (10 wt % on activated carbon) in 60 mL of methanol was stirred at room temperature under hydrogen gas atmosphere for 24 h. The precipitate were collected and dissolved in 10% NaOH solution and then filtered. The filtrate was acidified with dil aq HCl and the precipitate was then collected and washed with acetone and water to give 166.

Obtained as white solid; yield: 77%; mp>300° C.; ESI-MS (Positive mode): m/z 312 $[M+H]^+$, 408 $[M+Na]^+$; ESI-MS (Negative mode): m/z 310 $[M-H]^-$; $^1$H NMR (DMSO-$d_6$, 500 MHz): δ 3.80 (3H, s), 6.16 (2H, s), 6.24 (1H, s, br), 6.52 (1H, s), 6.77 (1H, s), 6.78 (1H, s), 7.22 (1H, s), 7.40 (1H, s), 9.91 (1H, s), 11.56 (1H, s, br); $^{13}$C-NMR (DMSO-$d_6$, 125 MHz): δ 55.77, 97.83, 101.52, 102.39, 103.29, 104.31, 106.74, 107.17, 120.79, 136.78, 137.77, 145.69, 149.27, 151.57, 159.38, 161.24, 175.93.

Dibenzyl 2-(3-([bis-[(benzyl)oxy]]phosphoryl)oxy-5-methoxyphenyl)-6,7-methylenedioxyquinolin-4-yl phosphate (167)

A suspension of 203.9 mg (0.65 mmol) of 166, 131.0 mg of NaH 60% in mineral oil and 705.4 mg (1.31 mmol) of tetrabenzyl pyrophosphate in 20 mL of dry tetrahydrofuran. The mixture was stirred at room temperature for 10 min. The reaction mixture was filtered and washed with tetrahydrofuran. The filtrate was concentrated under vacuum at a temperature below 30° C.

Obtained as a yellow oil; yield: 85%; ESI-MS (Positive mode): m/z 832 $[M+H]^+$; $^1$H-NMR (CDCl$_3$, 200 MHz): δ 3.77 (3H, s), 5.12 (4H, d, J=8.31 Hz), 5.17 (4H, d, J=9.54 Hz), 6.09 (2H, s), 6.78 (1H, m), 7.10 (1H, s), 7.23 (1H, s), 7.27-7.40 (22H, m), 7.52 (1H, d, J=0.98 Hz); $^{13}$C-NMR (CDCl$_3$, 50 MHz): δ 55.64, 70.01, 70.12, 70.53, 70.65, 97.16, 101.90, 106.07, 106.62, 110.04, 111.41, 111.52, 117.39, 117.53, 128.09, 128.14, 128.59, 128.67, 128.90, 134.91, 135.02, 135.38, 135.52, 141.49, 151.49, 151.64, 151.78, 153.74, 153.87, 154.86, 160.82.

2-(3-([bis-[(benzyl)oxy]]phosphoryl)oxy-5-methoxyphenyl)-6,7-methylenedioxyquinolin-4-one (168)

A suspension of 0.92 g (1.11 mmol) of 167 in 100 mL of methanol was stirred at 25° C. for 48 h. The precipitates were collected and purified by column chromatography ($SiO_2$, EtOAc) to give 168.

Obtained as a white solid; yield: 45%; ESI-MS (Positive mode): m/z 572 $[M+H]^+$, 594 $[M+Na]^+$; ESI-MS (Negative mode): m/z 570 $[M-H]^-$; $^1$H-NMR (CDCl$_3$, 500 MHz): δ 3.64 (3H, s), 5.07 (4H, d, J=9.20 Hz), 5.99 (2H, s), 6.37 (1H, s), 6.79 (1H, s), 7.09 (1H, s), 7.18 (1H, s), 7.27-7.29 (22H, m), 7.59 (1H, s); $^{13}$C-NMR (CDCl$_3$, 125 MHz): δ 55.57, 70.39, 70.43, 97.35, 101.83, 102.25, 107.57, 107.76, 107.82, 109.93, 110.00, 110.80, 110.90, 121.03, 128.09, 128.66, 128.87, 134.98, 134.02, 145.92, 148.07, 151.35, 151.40, 151.91, 160.90, 177.41.

2-(3-(dihydrogen)phosphate-5-methoxyphenyl)-6,7-methylenedioxyquinolin-4-one (169)

A suspension of 38.9 mg (0.068 mmol) of 168 and 20 mg of palladium (10 wt % on activated carbon) in 20 mL of anhydrous methanol was stirred at room temperature under hydrogen gas atmosphere for 15 min. The precipitate were collected and dissolved in 10% NaHCO$_3$ solution and then filtered. The filtrate was acidified with dil aq HCl and the precipitate was then collected and washed with acetone to give 169.

Obtained as white solid; yield: 80%; ESI-MS (Negative mode): m/z 390 [M−H]+; 1H NMR (D2O+NaOD, 500 MHz): δ 3.88 (3H, s), 6.01 (2H, s), 6.78 (1H, s), 6.93 (1H, s), 7.14 (1H, s), 7.15 (1H, s), 7.25 (1H, s), 7.44 (1H, s); 13C-NMR (D2O+NaOD, 125 MHz): δ 55.74, 99.41, 101.53, 103.57, 105.41, 106.64, 107.14, 112.32, 120.87, 142.31, 145.41, 147.13, 150.33, 155.24, 157.79, 159.78, 172.61.

IV-2. Anticancer Activity
In Vitro Tests

MTT (3-(4,5-Dimethylthiazol-2-yl)-2,5-diphenyltetrazolium bromide) assays. HL-60, Hep 3B, H460, A498, Colo205 and Detroit 551 cells were treated with tested compounds for the indicated periods. After treatment, cells were washed once with PBS and incubated with MTT (Sigma, St. Louis, Mo., USA) for 2 h. The formazan precipitate was dissolved in 150 μL of DMSO, and the absorbance was measured with an ELISA reader at 570 nm.

Results

Table 6 shows IC$_{50}$ (μM) Values from In Vitro Cytotoxicity Testing of 166.

TABLE 6

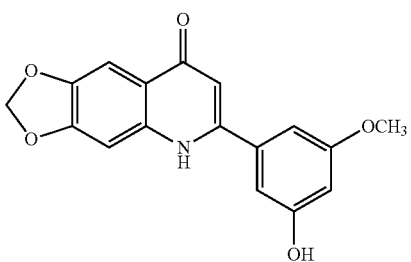 [SMILES: COc1cc(O)cc(-c2cc(=O)c3cc4c(cc3[nH]2)OCO4)c1]

166

| Compound | HL-60 | Hep 3B | H460 | A498 | Colo205 | Detroit 551 |
|---|---|---|---|---|---|---|
| 166 | 0.4 | >50 | >50 | >50 | >50 | >50 |

Representative compounds of the present invention are Show in Table 7 below.

TABLE 7

(Formula I)

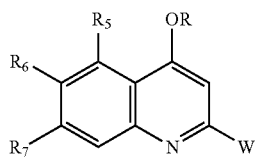

| Comp'd | Structure | Name | Substituent on Formula I |
|---|---|---|---|
| 16 | ![structure] | 2-(2-Fluorophenyl)-5,6-dimethoxyquinolin-4-one | R = H<br>W = 2-fluorophenyl<br>R5 = methoxy<br>R6 = methoxy<br>R7 = hydrogen |
| 17 | ![structure] | 2-(3-Fluorophenyl)-5,6-dimethoxyquinolin-4-one | R = H<br>W = 3-fluorophenyl<br>R5 = methoxy<br>R6 = methoxy<br>R7 = hydrogen |
| 18 | ![structure] | 2-(4-Fluorophenyl)-5,6-dimethoxyquinolin-4-one | R = H<br>W = 4-fluorophenyl<br>R5 = methoxy<br>R6 = methoxy<br>R7 = hydrogen |

TABLE 7-continued (Formula I)

| Comp'd | Structure | Name | Substituent on Formula I |
|---|---|---|---|
| 19 | 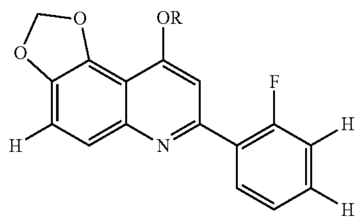 | 2-(2-Fluorophenyl)-5,6-methylenedioxy quinolin-4-one | R = H<br>W = 2-fluorophenyl<br>R5, R6 = methylenedioxy<br>R7 = hydrogen |
| 20 | 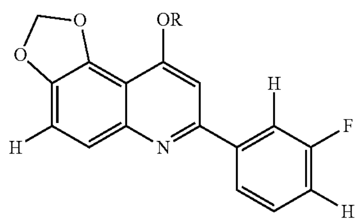 | 2-(3-Fluorophenyl)-5,6-methylenedioxy quinolin-4-one | R = H<br>W = 3-fluorophenyl<br>R5, R6 = methylenedioxy<br>R7 = hydrogen |
| 21 | 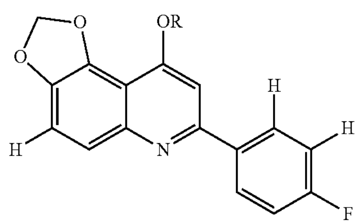 | 2-(4-Fluorophenyl)-5,6-methylenedioxy quinolin-4-one | R = H<br>W = 4-Fluorophenyl<br>R5, R6 = methylenedioxy<br>R7 = hydrogen |
| 22 | 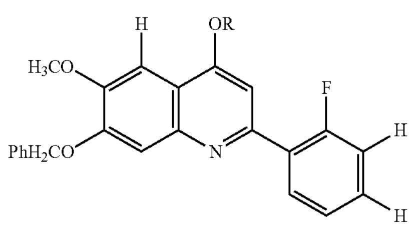 | 7-Benzyloxy-2-(2-fluorophenyl)-6-methoxyquinolin-4-one | R = H<br>W = 2-fluorophenyl<br>R5 = hydrogen<br>R6 = methoxy<br>R7 = O-benzyl |
| 23 | 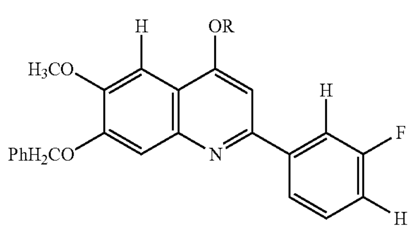 | 7-Benzyloxy-2-(3-fluorophenyl)-6-methoxyquinolin-4-one | R = H<br>W = 3-fluorophenyl<br>R5 = hydrogen<br>R6 = methoxy<br>R7 = O-benzyl |
| 24 | 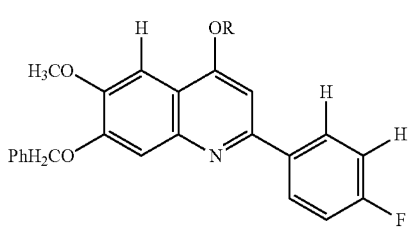 | 7-Benzyloxy-2-(4-fluorophenyl)-6-methoxyquinolin-4-one | R = H<br>W = 4-fluorophenyl<br>R5 = hydrogen<br>R6 = methoxy<br>R7 = O-benzyl |

TABLE 7-continued (Formula I)

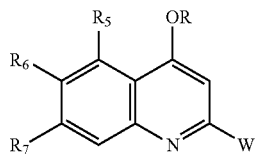

| Comp'd | Structure | Name | Substituent on Formula I |
|---|---|---|---|
| 37 | 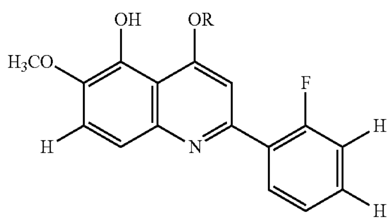 | 2-(2-Fluorophenyl)-5-hydroxy-6-methoxyquinolin-4-one | R = H<br>W = 2-fluorophenyl<br>R5 = hydroxyl<br>R6 = methoxy<br>R7 = hydrogen |
| 38 | 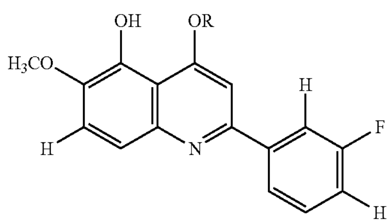 | 2-(3-Fluorophenyl)-5-hydroxy-6-methoxyquinolin-4-one | R = H<br>W = 3-fluorophenyl<br>R5 = hydroxyl<br>R6 = methoxy<br>R7 = hydrogen |
| 39 | 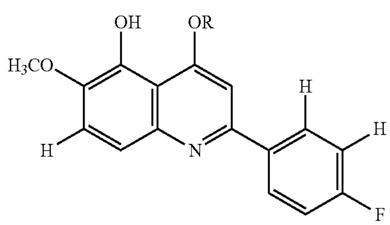 | 2-(4-Fluorophenyl)-5-hydroxy-6-methoxyquinolin-4-one | R = H<br>W = 4-fluorophenyl<br>R5 = hydroxyl<br>R6 = methoxy<br>R7 = hydrogen |
| 40 | 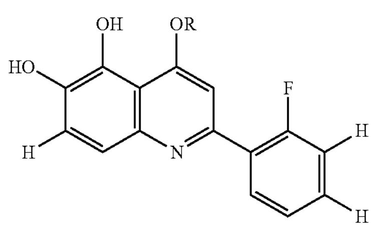 | 2-(2-Fluorophenyl)-5,6-dihydroxyquinolin-4-one | R = H<br>W = 2-fluorophenyl<br>R5 = hydroxyl<br>R6 = hydroxyl<br>R7 = hydrogen |
| 41 | 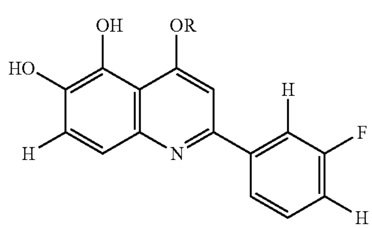 | 2-(3-Fluorophenyl)-5,6-dihydroxyquinolin-4-one | R = H<br>W = 3-fluorophenyl<br>R5 = hydroxyl<br>R6 = hydroxyl<br>R7 = hydrogen |

TABLE 7-continued (Formula I)

| Comp'd | Structure | Name | Substituent on Formula I |
|---|---|---|---|
| 42 | 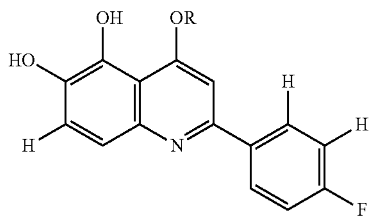 | 2-(4-Fluorophenyl)-5,6-dihydroxyquinolin-4-one | R = H<br>W = 4-fluorophenyl<br>R5 = hydroxyl<br>R6 = hydroxyl<br>R7 = hydrogen |
| 43 | 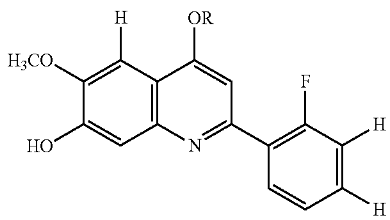 | 2-(2-Fluorophenyl)-7-hydroxy-6-methoxy-quinolin-4-one | R = H<br>W = 2-fluorophenyl<br>R5 = hydrogen<br>R6 = methoxy<br>R7 = hydroxyl |
| 44 | 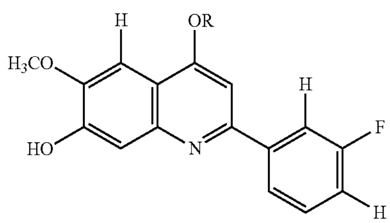 | 2-(3-Fluorophenyl)-7-hydroxy-6-methoxy-quinolin-4-one | R = H<br>W = 3-fluorophenyl<br>R5 = hydrogen<br>R6 = methoxy<br>R7 = hydroxyl |
| 45 | 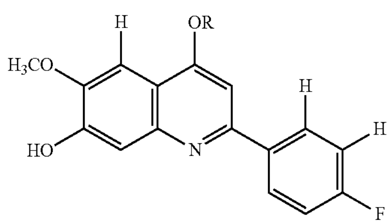 | 2-(4-Fluorophenyl)-7-hydroxy-6-methoxy-quinolin-4-one | R = H<br>W = 4-fluorophenyl<br>R5 = hydrogen<br>R6 = methoxy<br>R7 = hydroxyl |
| 48 | 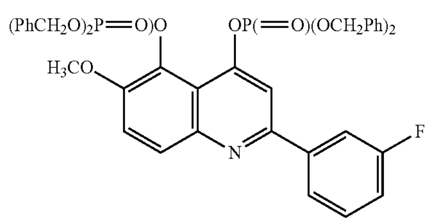 | 2-(3-Fluorophenyl)-6-methoxyquinoline-4,5-diyl bis(dibenzyl phosphate) | R = PO(O-benzyl)2<br>W = 3-fluorophenyl<br>R5 = OR8<br>R6 = methoxy<br>R7 = hydrogen<br>R8 = P(=O)(O-benzyl)2 |
| 49 | 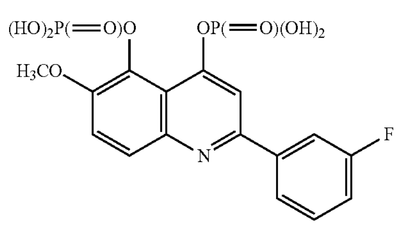 | 2-(3-Fluorophenyl)-6-methoxyquinoline-4,5-diyl bis(dihydrogen phosphate) | R = PO(OH)2<br>W = 3-fluorophenyl<br>R5 = OR8<br>R6 = methoxy<br>R7 = hydrogen<br>R8 = —P(=O)(OH)2 |

TABLE 7-continued (Formula I)

| Comp'd | Structure | Name | Substituent on Formula I |
|---|---|---|---|
| 50 | (structure) | 2-(3-Fluorophenyl)-6-methoxyquinoline-4,5-diyl bis(disodium phosphate) | R = PO(ONa)2<br>W = 3-fluorophenyl<br>R5 = OR8<br>R6 = methoxy<br>R7 = hydrogen<br>R8 = P(=O)(ONa)2 |
| 51 | (structure) | Dibenzyl 2-(3-fluorophenyl)-6-methoxy-4-oxo-1,4-dihydroquinolin-5-yl phosphate | R = H<br>W = 3-fluorophenyl<br>R5 = OR8<br>R6 = methoxy<br>R7 = hydrogen<br>R8 = P(=O)(O-benzyl)2 |
| 52 | (structure) | 2-(3-Fluorophenyl)-6-methoxy-4-oxo-1,4-dihydroquinolin-5-yl dihydrogen phosphate | R = H<br>W = 3-fluorophenyl<br>R5 = OR8<br>R6 = methoxy<br>R7 = hydrogen<br>R8 = P(=O)(OH)2 |
| 53 | (structure) | Sodium 2-(3-fluorophenyl)-6-methoxy-4-oxo-1,4-dihydroquinolin-5-yl phosphate | R = H<br>W = 3-fluorophenyl<br>R5 = OR8<br>R6 = methoxy<br>R7 = hydrogen<br>R8 = P(=O)(ONa)2 |
| 124 | (structure) | 2-(benzo[d][1,3]dioxol-86-yl)-6-morpholinoquinolin-4-one | R = H<br>W = benzo[d][1,3]dioxol-4-yl,<br>R5 = hydrogen<br>R6 = N-morpholino<br>R7 = hydrogen |
| 125 | (structure) | 2-(benzo[d][1,3]dioxol-4-yl)-6-pyrrolidinoquinolin-4-one | R = H<br>W= benzo[d][1,3]dioxol-4-yl,<br>R5 = hydrogen<br>R6 = N-pyrrolindino<br>R7 = hydrogen |

TABLE 7-continued (Formula I)

| Comp'd | Structure | Name | Substituent on Formula I |
|---|---|---|---|
| 126 | 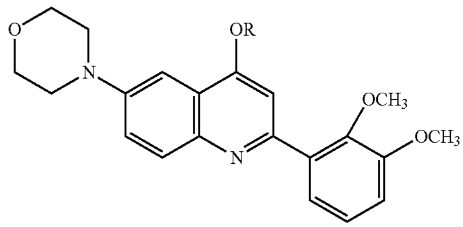 | 2-(2,3-dimethoxyphenyl)-6-morpholino-quinolin-4-one | R = H<br>W = 2,3-dimethoxyphenyl<br>R5 = hydrogen<br>R6 = N-morpholino<br>R7 = hydrogen |
| 127 | 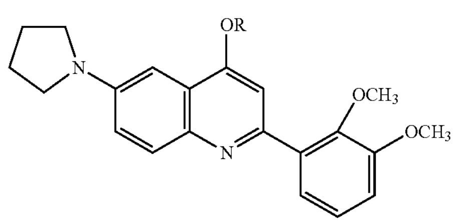 | 2-(2,3-dimethoxyphenyl)-6-pyrrolidino-quinolin-4-one | R = H<br>W = 2,3-dimethoxyphenyl<br>R5 = hydrogen<br>R6 = N-pyrrolindino<br>R7 = hydrogen |
| 128 | 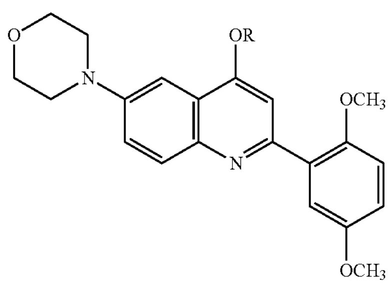 | 2-(2,5-dimethoxyphenyl)-6-morpholino-quinolin-4-one | R = H<br>W = 2,5-dimethoxyphenyl<br>R5 = hydrogen<br>R6 = N-morpholino<br>R7 = hydrogen |
| 129 | 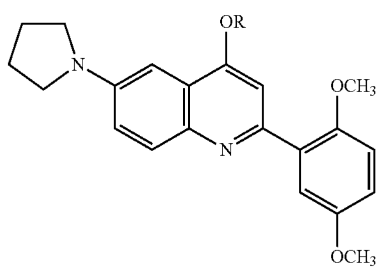 | 2-(2,5-dimethoxyphenyl)-6-pyrrolidino-quinolin-4-one | R = H<br>W = 2,5-dimethoxyphenyl<br>R5 = hydrogen<br>R6 = N-pyrrolindino<br>R7 = hydrogen |
| 130 | 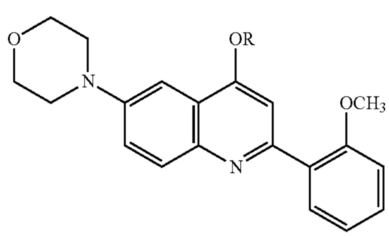 | 2-(2-methoxyphenyl)-6-morpholino-quinolin-4-one | R = H<br>W = 2-methoxyphenyl<br>R5 = hydrogen<br>R6 = N-morpholino<br>R7 = hydrogen |

TABLE 7-continued

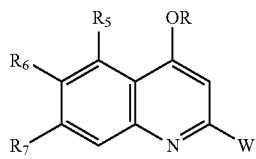
(Formula I)

| Comp'd | Structure | Name | Substituent on Formula I |
|---|---|---|---|
| 131 | 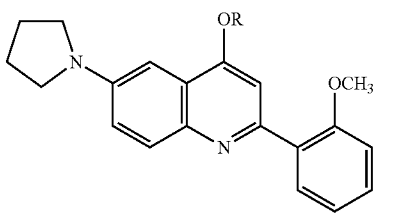 | 2-(2,5-dimethoxyphenyl)-6-pyrrolidino-quinolin-4-one | R = H<br>W = 2-methoxyphenyl<br>R5 = hydrogen<br>R6 = N-pyrrolindino<br>R7 = hydrogen |
| 132 | 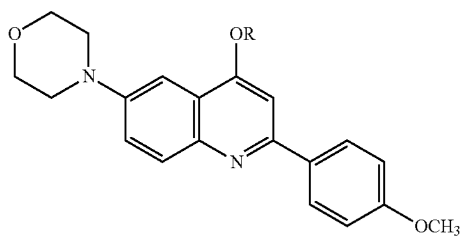 | 2-(4-methoxyphenyl)-6-morpholinoquinolin-4-one | R = H<br>W = 4-methoxyphenyl<br>R5 = hydrogen<br>R6 = N-morpholino<br>R7 = hydrogen |
| 133 | 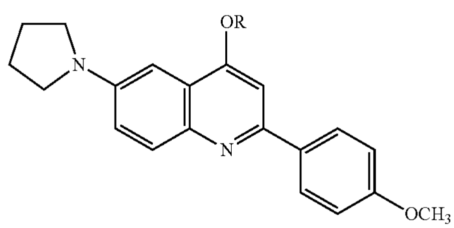 | 2-(4-methoxyphenyl)-6-pyrrolidinoquinolin-4-one | R = H<br>W = 4-methoxyphenyl<br>R5 = hydrogen<br>R6 = N-pyrrolindino<br>R7 = hydrogen |
| 134 | 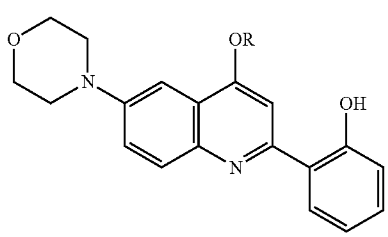 | 2-(2-Hydroxyphenyl)-6-morpholinoquinolin-4-one | R = H<br>W = 2-hydroxyphenyl<br>R5 = hydrogen<br>R6 = N-morpholino<br>R7 = hydrogen |
| 135 | 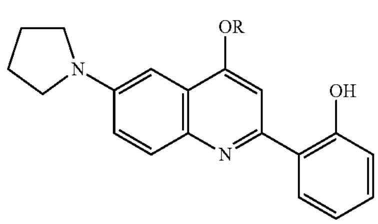 | 2-(2-hydroxyphenyl)--6-pyrrolidinoquinolin-4-one | R = H<br>W = 2-hydroxyphenyl<br>R5 = hydrogen<br>R6 = N-pyrrolindino<br>R7 = hydrogen |

TABLE 7-continued (Formula I)

| Comp'd | Structure | Name | Substituent on Formula I |
|---|---|---|---|
| 136 | 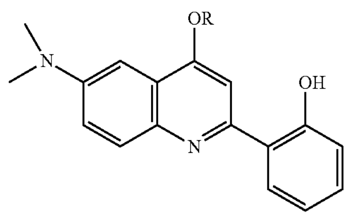 | 2-(2-hydroxyphenyl)-6-dimethylaminoquinolin-4-one | R = H<br>W = 2-hydroxyphenyl<br>R5 = hydrogen<br>R6 = N,N-dimethylamino<br>R7 = hydrogen |
| 137 | 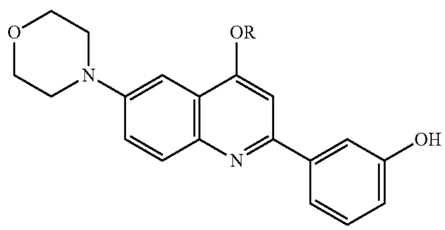 | 2-(3-Hydroxyphenyl)-6-morpholinoquinolin-4-one | R = H<br>W = 3-hydroxyphenyl<br>R5 = hydrogen<br>R6 = N-morpholino<br>R7 = hydrogen |
| 138 | 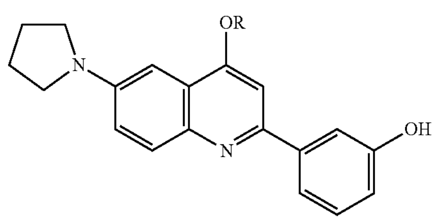 | 2-(3-hydroxyphenyl)-6-pyrrolidinoquinolin-4-one | R = H<br>W = 3-hydroxyphenyl<br>R5 = hydrogen<br>R6 = N-pyrrolindino<br>R7 = hydrogen |
| 139 | 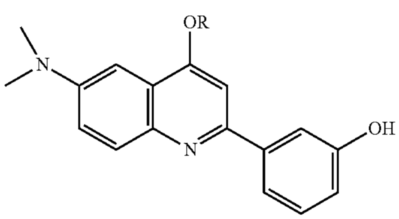 | 2-(3-hydroxyphenyl)-6-dimethylaminoquinolin-4-one | R = H<br>W = 3-hydroxyphenyl<br>R5 = hydrogen<br>R6 = N,N-dimethylamino<br>R7 = hydrogen |
| 140 | 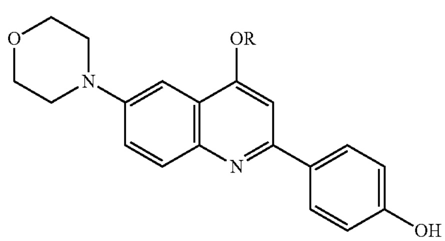 | 2-(4-Hydroxyphenyl)-6-morpholinoquinolin-4-one | R = H<br>W = 4-hydroxyphenyl<br>R5 = hydrogen<br>R6 = N-morpholino<br>R7 = hydrogen |
| 141 | 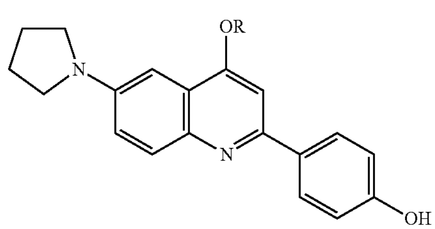 | 2-(4-hydroxyphenyl)-6-pyrrolidinoquinolin-4-one | R = H<br>W = 4-hydroxyphenyl<br>R5 = hydrogen<br>R6 = N-pyrrolindino<br>R7 = hydrogen |

TABLE 7-continued

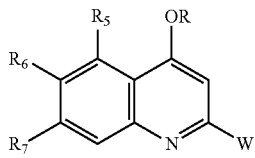
(Formula I)

| Comp'd | Structure | Name | Substituent on Formula I |
|---|---|---|---|
| 142 | 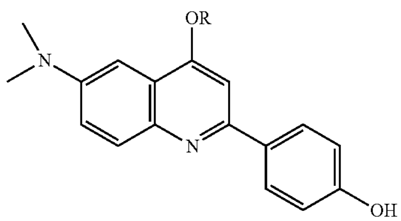 | 2-(4-hydroxyphenyl)-6-dimethylaminoquinolin-4-one | R = H<br>W = 4-hydroxyphenyl<br>R5 = hydrogen<br>R6 = N,N-dimethylamino<br>R7 = hydrogen |
| 143 | 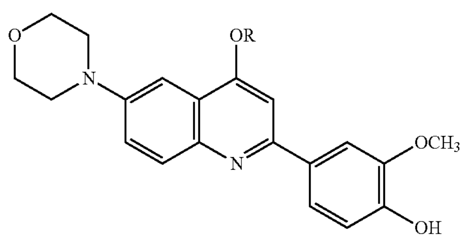 | 2-(4-hydroxy-3-methoxyphenyl)-6-morpholinoquinolin-4-one | R = H<br>W = 4-hydroxy-3-methoxyphenyl<br>R5 = hydrogen<br>R6 = N-morpholino<br>R7 = hydrogen |
| 143a | 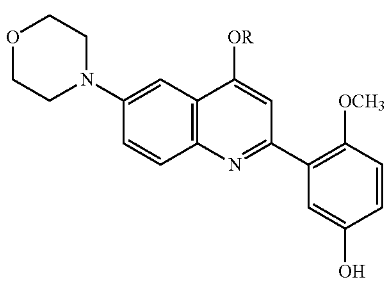 | 2-(5-hydroxy-2-methoxyphenyl)-6-morpholinoquinolin-4-one | R = H<br>W = 5-hydroxy-2-methoxyphenyl<br>R5 = hydrogen<br>R6 = N-morpholino<br>R7 = hydrogen |
| 143b | 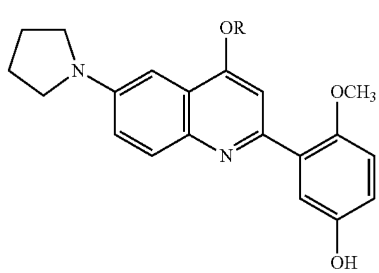 | 2-(5-hydroxy-2-methoxyphenyl)-6-pyrrolidino-quinolin-4-one | R = H<br>W = 5-hydroxy-2-methoxyphenyl<br>R5 = hydrogen<br>R6 = N-pyrrolindino<br>R7 = hydrogen |
| 144 | 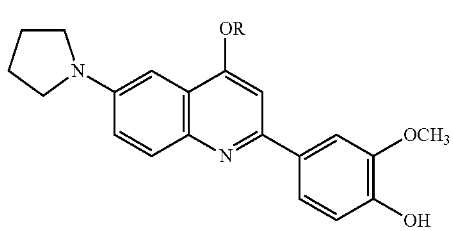 | 2-(4-hydroxy-3-methoxyphenyl)-6-pyrrolidino-quinolin-4-one | R = H<br>W = 4-hydroxy-3-methoxyphenyl<br>R5 = hydrogen<br>R6 = N-pyrrolindino<br>R7 = hydrogen |

TABLE 7-continued (Formula I)

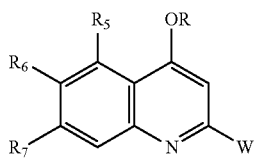

| Comp'd | Structure | Name | Substituent on Formula I |
|---|---|---|---|
| 144a | 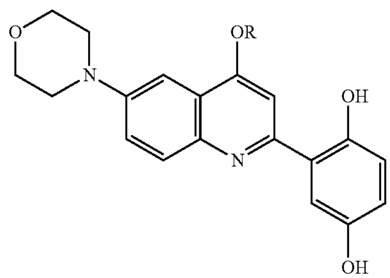 | 2-(2,5-dihydroxyphenyl)-6-morpholinoquinolin-4-one | R = H<br>W = 2,5-dihydroxyphenyl<br>R5 = hydrogen<br>R6 = N-morpholino<br>R7 = hydrogen |
| 144b | 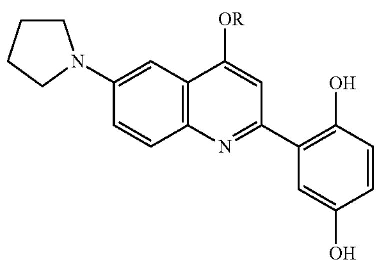 | 2-(2,5-dihydroxy-phenyl)-6-pyrrolidinoquinolin-4-one | R = H<br>W = 2,5-dihydroxyphenyl<br>R5 = hydrogen<br>R6 = N-pyrrolindino<br>R7 = hydrogen |
| 146 | 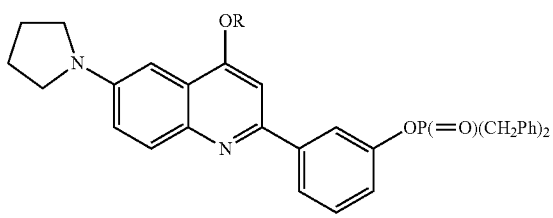 | Dibenzyl 3-(4-oxo-6-(pyrrolidin-1-yl)-1,4-dihydroquinolin-2-yl)phenyl phosphate | R = H<br>W = 3-OR8-phenyl<br>R5 = hydrogen<br>R6 = N-pyrrolindino<br>R8 = P(=O)(O-benzyl)2 |
| 147 | 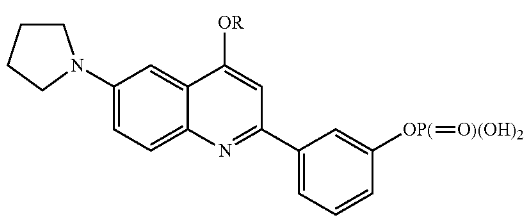 | 3-(4-Oxo-6-(pyrrolidin-1-yl)-1,4-dihydroquinolin-2-yl)phenyl dihydrogen phosphate | R = H<br>W= 3-OR8-phenyl<br>R5 = hydrogen<br>R6 = N-pyrrolindino<br>R8 = P(=O)(OH)2 |
| 151 (JMC-39) | 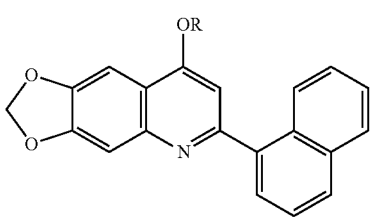 | 2-(1-Naphthalenyl)-6,7-methylenedioxy quinolin-4-one | R = H<br>W = naphtha-1-yl<br>R5 = hydrogen<br>R6 and R7 = methylenedioxy |

TABLE 7-continued (Formula I)

| Comp'd | Structure | Name | Substituent on Formula I |
|---|---|---|---|
| 152 | OP(=O)(OCH$_2$Ph)$_2$ | Dibenzyl 2-(1-naphthalenyl)-6,7-methylenedioxyquinolin-4-yl phosphate | R = P(=O)(O-benzyl)2<br>W = naphtha-1-yl<br>R5 = hydrogen<br>R6 and R7 = methylenedioxy |
| 153 | OP(=O)(OH)$_2$ | 2-(1-Naphthalenyl)-6,7-methylenedioxy-quinolin-4-yl dihydrogen phosphate | R = P(=O)(OH)2<br>W = naphtha-1-yl<br>R5 = hydrogen<br>R6 and R7 = methylenedioxy |
| 156 (JMC-37) | OR | 2-(3-Benzo[b]furyl)-6,7-methylenedioxy-quinolin-4-one | R = H<br>W = benzo[b]furan-3-yl<br>R5 = hydrogen<br>R6 and R7 = methylenedioxy |
| 157 | OP(=O)(OCH$_2$Ph)$_2$ | Dibenzyl 2-(3-benzo[b]furyl)-6,7-methylenedioxy quinolin-4-yl phosphate | R = P(=O)(O-benzyl)2<br>W = benzo[b]furan-3-yl<br>R5 = hydrogen<br>R6 and R7 = methylenedioxy |
| 158 | OP(=O)(OH)$_2$ | 2-(3-Benzo[b]furyl)-6,7-methylenedioxy quinolin-4-yl dihydrogen phosphate | R = P(=O)(OH)2<br>W = benzo[b]furan-3-yl<br>R5 = hydrogen<br>R6 and R7 = methylenedioxy |
| 166 | OR | 2-(3-Hydroxy-5-methoxyphenyl)-6,7-methylenedioxyquinolin-4-one | R = H<br>W = 3-OR8-5-methoxyphenyl<br>R5 = hydrogen<br>R6 and R7 = methylenedioxy |

TABLE 7-continued

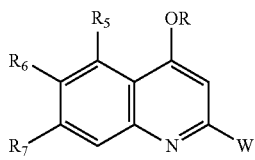
(Formula I)

| Comp'd | Structure | Name | Substituent on Formula I |
|---|---|---|---|
| 167 | 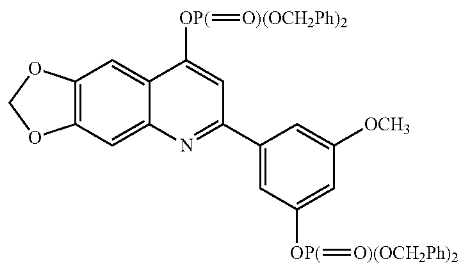 | Dibenzyl 2-(3-([bis-[(benzyl)oxy]]phosphoryl)oxy-5-methoxyphenyl)-6,7-methylenedioxyquinolin-4-yl phosphate | R = P(=O)(O-benzyl)2<br>W = 3-OR8-5-methoxyphenyl<br>R5 = hydrogen<br>R6 and R7 = methylenedioxy<br>R8 = P(=O)(O-benzyl)2 |
| 168 | 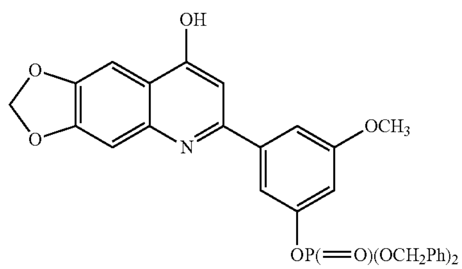 | 2-(3-([bis-[(benzyl)oxy]]phosphoryl)oxy-5-methoxyphenyl)-6,7-methylenedioxyquinolin-4-one | R = H<br>W = 3-OR8-5-methoxyphenyl<br>R5 = hydrogen<br>R6 and R7 = methylenedioxy<br>R8 = P(=O)(O-benzyl)2 |
| 169 | 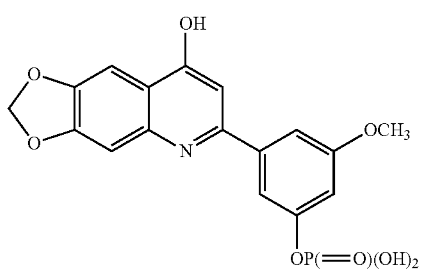 | 2-(3-(dihydrogen)phosphate-5-methoxy-phenyl)-6,7-methylene-dioxyquinolin-4-one | R = H<br>W = 3-OR8-5-methoxyphenyl<br>R5 = hydrogen<br>R6 and R7 = methylenedioxy<br>R8 = P(=O)(OH)2 |
| JMC-1 | 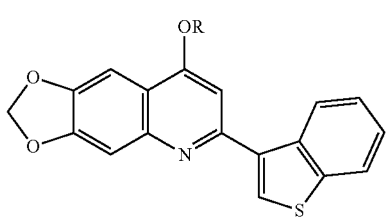 | 2-(3-Benzo[b]thienyl)-6,7-methylene-dioxyquinolin-4-one | R = H<br>W = benzo[b]thiophen-3-yl<br>R5 = hydrogen<br>R6 and R7 = methylenedioxy |
| JMC-36 | 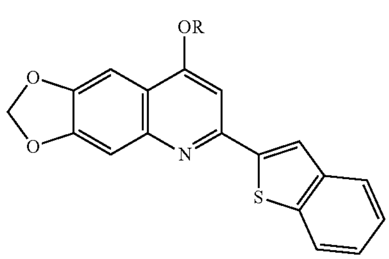 | 2-(2-Benzo[b]thienyl)-6,7-methylenedioxy-quinolin-4-one | R = H<br>W = benzo[b]thiophen-2-yl<br>R5 = hydrogen<br>R6 and R7 = methylenedioxy |

TABLE 7-continued (Formula I)

| Comp'd | Structure | Name | Substituent on Formula I |
|---|---|---|---|
| JMC-38 | 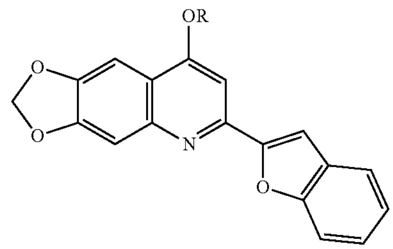 | 2-(2-Benzo[b]furyl)-6,7-methylenedioxy quinolin-4-one | R = H<br>W = benzo[b]furan-2-yl<br>R6 and R7 = methylenedioxy<br>R5 = H |
| JMC-40 | 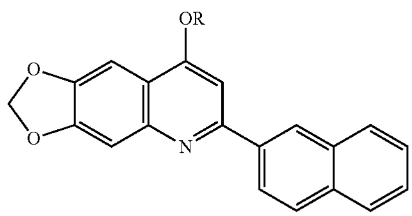 | 2-(2-Naphthalenyl)-6,7-methylenedioxy quinolin-4-one | R = H<br>W = naphtha-2-yl<br>R5 = hydrogen<br>R6 and R7 = methylenedioxy |
| JMC-41 | 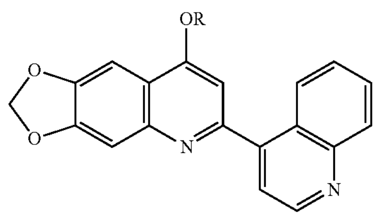 | 2-(4-Quinolinyl)-6,7-methylenedioxy-quinolin-4-one | R = H<br>W = quinolin-4-yl<br>R5 = hydrogen<br>R6 and R7 = methylenedioxy |
| JMC-42 | 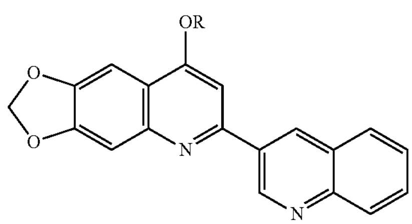 | 2-(3-Quinolinyl)-6,7-methylenedioxy-quinolin-4-one | R = H<br>W = quinolin-3-yl<br>R5 = hydrogen<br>R6 and R7 = methylenedioxy |
| JMC-43 | 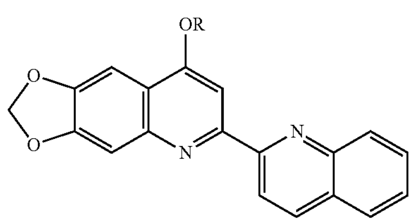 | 2-(2-Quinolinyl)-6,7-methylenedioxy-quinolin-4-one | R = H<br>W = quinolin-2-yl<br>R5 = hydrogen<br>R6 and R7 = methylenedioxy |
| JMC-44 | 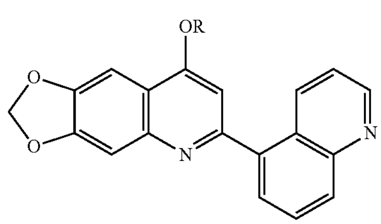 | 2-(5-Quinolinyl)-6,7-methylenedioxy-quinolin-4-one | R = H<br>W = quinolin-5-yl<br>R5 = hydrogen<br>R6 and R7 = methylenedioxy |

TABLE 7-continued (Formula I)

| Comp'd | Structure | Name | Substituent on Formula I |
|---|---|---|---|
| JMC-45 | 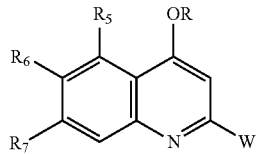 | 2-(1-Anthracenyl)-6,7-methylenedioxy-quinolin-4-one | R = H<br>W = anthracen-1-yl<br>R5 = hydrogen<br>R6 and R7 = methylenedioxy |

The foregoing description of the exemplary embodiments of the invention has been presented only for the purposes of illustration and description and is not intended to be exhaustive or to limit the invention to the precise forms disclosed. The embodiments and examples were chosen and described in order to explain the principles of the invention and their practical application so as to enable others skilled in the art to utilize the invention and various embodiments and with various modifications as are suited to the particular use contemplated. Accordingly, the scope of the present invention is defined by the appended claims rather than the foregoing description and the exemplary embodiments described therein.

All references cited and discussed in this specification are incorporated herein by reference in their entireties and to the same extent as if each reference was individually incorporated by reference.

What is claimed is:

1. A compound of Formula I:

Formula I or a pharmaceutically acceptable salt thereof,
(i) wherein:
R is hydrogen, $PO(OH)_2$, $P(=O)(O-(C_1-C_{18})$alkylenephenyl))$_2$, $P(=O)(OH)(OM)$, or $P(=O)(OM)_2$;
W is 2-halophenyl, 3-halophenyl, -halophenyl;
$R_5$ is $(C_1-C_{18})$alkoxy, hydrogen, hydroxyl, $OR_8$;
$R_6$ is hydroxyl, or $(C_1-C_{18})$alkoxy;
$R_7$ is hydrogen, hydroxyl, or $O-(C_1-C_{18})$alkylenephenyl;
$R_8$ is hydrogen, $PO(OH)_2$, $P(=O)(O-(C_1-C_{18})$alkylenephenyl)$_2$, $P(=O)(OH)(OM)$, or $P(=O)(OM)_2$; and
M is a monovalent or divalent metal ion, or alkylammonium ion;
(ii) or wherein;

R is hydrogen, $PO(OH)_2$, $P(=O)(O-(C_1-C_{18})$alkylenephenyl))$_2$, $P(=O)(OH)(OM)$, or $P(=O)(OM)_2$;
W is 2-halophenyl, 3-halophenyl, 4-halophenyl;
$R_5$ is hydrogen, $(C_1-C_{18})$alkoxy, hydroxyl, or $OR_8$;
$R_6$ is hydroxyl or $(C_1-C_{18})$alkoxy;
$R_7$ hydroxyl, or $O-(C_1-C_{18})$alkylenephenyl;
$R_8$ hydrogen, $PO(OH)_2$, $P(=O)(O-(C_1-C_{18})$alkylenephenyl)$_2$, $P(=O)(OH)(OM)$, or $P(=O)(OM)_2$; and
M is a monovalent or divalent metal ion, or alkylammonium ion.

2. The compound of claim 1,
(i) wherein;
R is hydrogen, $P(=O)(OH)_2$, $P(=O)(O$-benzyl$)_2$, $P(=O)(OH)(OM)$, or $P(=O)(OM)_2$;
W is 2-fluorophenyl, 3-fluorophenyl, 4-fluorophenyl,
$R_5$ is methoxy, hydroxyl, halo or $OR_8$;
$R_6$ is hydroxyl or methoxy;
$R_7$ is hydrogen, hydroxyl, or O-benzyl;
$R_8$ is hydrogen $PO(OH)_2$, $P(=O)(O$-benzyl$)_2$, $P(=O)(OH)(OM)$, or $P(=O)(OM)_2$, and
M is a sodium ion;
(ii) or wherein
R is hydrogen, $PO(OH)_2$, $P(=O)(O$-benzyl$)_2$, $P(=O)(OH)(OM)$, or $P(=O)(OM)_2$;
W is 2-fluorophenyl, 3-fluorophenyl, 4-fluorophenyl,
$R_5$ is methoxy, hydroxyl, halo or $OR_8$;
$R_6$ is hydroxyl or methoxy;
$R_7$ is hydrogen, hydroxyl, or O-benzyl;
$R_8$ is hydrogen $PO(OH)_2$, $P(=O)(O$-benzyl$)_2$, $P(=O)(OH)(OM)$, or $P(=O)(OM)_2$, and
M is a sodium ion.

3. The compound of claim 2, wherein the compound is selected from the group consisting of
2-(2-Fluorophenyl)-5,6-dimethoxyquinolin-4-one;
2-(3-Fluorophenyl)-5,6-dimethoxyquinolin-4-one;
2-(4-Fluorophenyl)-5,6-dimethoxyquinolin-4-one;
7-Benzyloxy-2-(2-fluorophenyl)-6-methoxyquinolin-4-one;
7-Benzyloxy-2-(3-fluorophenyl)-6-methoxyquinolin-4-one;
7-Benzyloxy-2-(4-fluorophenyl)-6-methoxyquinolin-4-one;

2-(2-Fluorophenyl)-5-hydroxy-6-methoxyquinolin-4-one;

2-(3-Fluorophenyl)-5-hydroxy-6-methoxyquinolin-4-one;

2-(4-Fluorophenyl)-5-hydroxy-6-methoxyquinolin-4-one;

2-(2-Fluorophenyl)-5,6-dihydroxyquinolin-4-one;

2-(3-Fluorophenyl)-5,6-dihydroxyquinolin-4-one;

2-(4-Fluorophenyl)-5,6-dihydroxyquinolin-4-one;

2-(2-Fluorophenyl)-7-hydroxy-6-methoxyquinolin-4-one;

2-(3-Fluorophenyl)-6-methoxyquinolin-4,5-diyl bis(dibenzyl phosphate), 2-(3-Fluorophenyl)-6-methoxyquinolin-4,5-diyl bis(dihydrogen phosphate), 2-(3-Fluorophenyl)-6-methoxyquinolin-4,5-diyl bis(disodium phosphate), Dibenzyl 2-(3-fluorophenyl)-6-methoxy-4-oxo-1,4-dihydroquinolin-5-yl phosphate, 2-(3-Fluorophenyl)-6-methoxy-4-oxo-1,4-dihydroquinolin-5-yl dihydrogen phosphate, and Sodium 2-(3-fluorophenyl)-6-methoxy-4-oxo-1,4-dihydroquinolin-5-yl phosphate.

4. The compound of claim 2, wherein the compound comprises is selected from the group consisting of

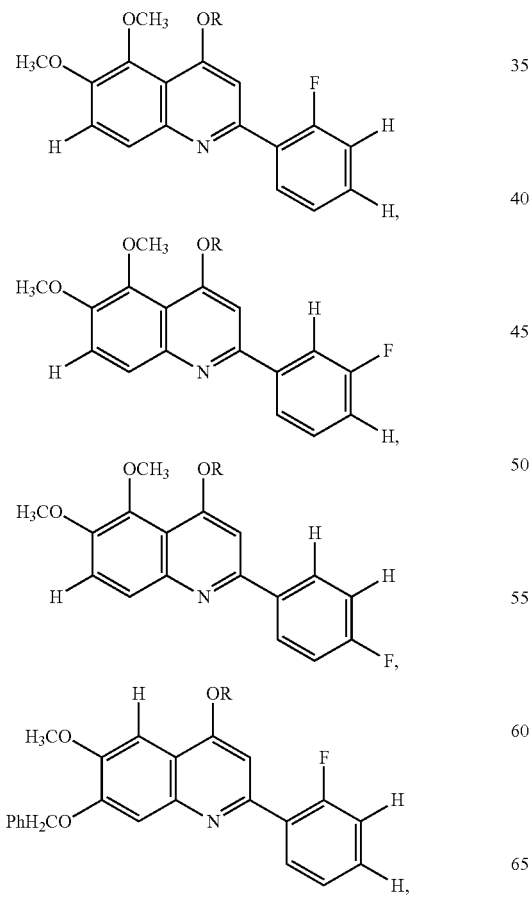

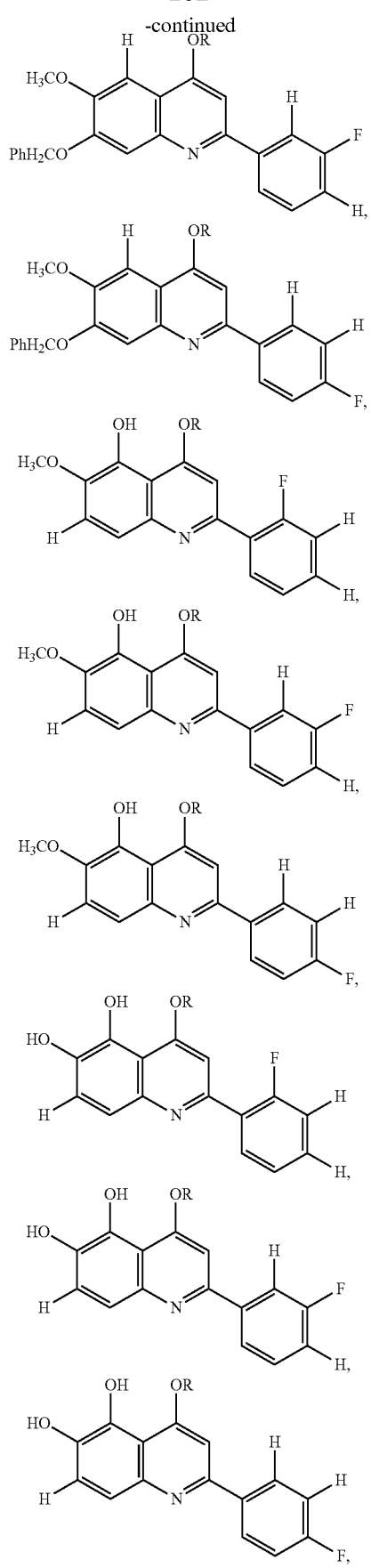

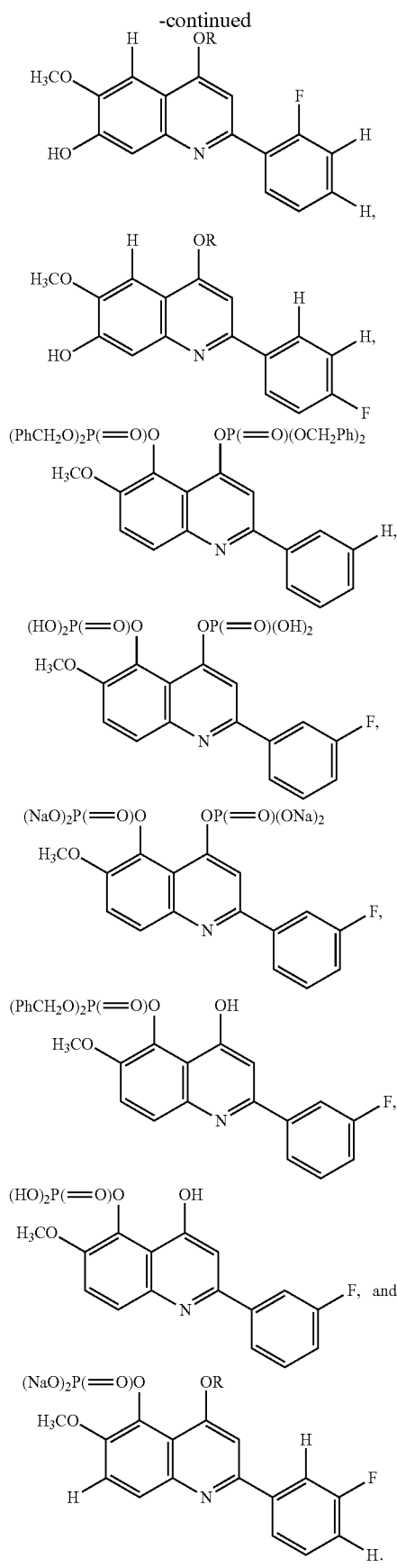

5. A compound of Formula I:

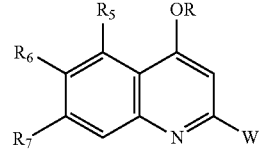

Formula I or pharmaceutically acceptable salt therof, wherein:
R is hydrogen, PO(OH)$_2$, P(=O)(O—($C_1$-$C_{\infty}$)alkylenephenyl))$_2$, P(=O)(OH)(OM), or P(=O)(OM)$_2$;
W is benzo[d][1,3]dioxol-4-yl, 2,3-di($C_1$-$C_{18}$)alkoxyphenyl, 2,5-di($C_1$-$C_{18}$)alkoxyphenyl, 2-($C_1$-$C_{18}$)alkoxyphenyl, 4-($C_1$-$C_{18}$)alkoxyphenyl, 2-hydroxyphenyl, 3-hydroxyphenyl, 4-hydroxyphenyl, 4-hydroxy-3-($C_1$-$C_{18}$)alkoxyphenyl, 5-hydroxy-2-($C_1$-$C_{18}$)alkoxy phenyl, 3-(O-di($C_1$-$C_{18}$)alkylenephenyl))phenyl, 3-(O-dihydrogen phosphate)phenyl, or 2,5-dihydroxyphenyl;
R$_5$ is hydrogen;
R$_6$ hydroxyl, ($C_1$-$C_{18}$)alkoxy, N,N-di($C_1$-$C_{18}$)alkylamino, or N—($C_1$-$C_{18}$)cycloalkylamino;
R$_7$ is hydrogen.

6. The compound of claim 5, wherein:
R is hydrogen;
W is benzo[d][1,3]dioxo1-4-yl, 2,3-dimethoxyphenyl, 2,5-dimethoxyphenyl, 2-methoxyphenyl, 4-methoxyphenyl, 2-hydroxyphenyl, 3-hydroxyphenyl, 4-hydroxyphenyl, 4-hydroxy-3-metboxyphenyl, 5-hydroxy-2-methoxyphenyl, 3-(O-dibenzylphosphate)phenyl, 3-(O-dihydrogen phosphate)phenyl, or 2,5-dihydroxyphenyl;
R$_5$ is hydrogen;
R$_6$ is hydroxyl, methoxy, N,N-dimethylamino, N-morpholino, or N-pyrrolindino; and R$_7$ is hydrogen.

7. The compound of claim 6, wherein the compound is selected from the group consisting of
2-(benzo[d][1,3]dioxol-1-yl)-6-morpholinoquinolin-4-one,
2-(benzo[d][1,3]dioxol-4-yl)-6-pyrrolidinoquinolin-4-one,
2-(2,3-dimethoxyphenyl)-6-morpholinoquinolin-4-one,
2-(2,3-dimethoxyphenyl)-6-pyrrolidinoquinolin-4-one,
2-(2,5-dimethoxyphenyl)-6-morpholinoquinolin-4-one,
2-(2,5-dimethoxyphenyl)-6-pyrrolidinoquinolin-4-one,
2-(2-methoxyphenyl)-6-morpholinoquinolin-4-one,
2-(2,5-dimethoxyphenyl)-6-pyrrolidinoquinolin-4-one,
2-(4-methoxyphenyl)-6-morpholinoquinolin-4-one,
2-(4-methoxyphenyl)-6-pyrrolidinoquinolin-4-one,
2-(2-Hydroxyphenyl)-6-morpholinoquinolin-4-one,
2-(2-hydroxyphenyl)-6-pyrrolidinoquinolin-4-one,
2-(2-hydroxyphenyl)-6-dimethylaminoquinolin-4-one,
2-(3-Hydroxyphenyl)-6-morpholinoquinolin-4-one,
2-(3-hydroxyphenyl)-6-pyrrolidinoquinolin-4-one,
2-(3-hydroxyphenyl)-6-dimethyaminoquinolin-4-one,
2-(4-Hydroxyphenyl)-6-morpholinoquinolin-4-one,
2-(4-hydroxyphenyl)-6-pyrrolidinoquinolin-4-one,
2-(4-hydroxyphenyl)-6-dimethylaminoquinolin-4-one,
2-(4-hydroxy-3-methoxyphenyl)-6-morpholinoquinolin-4-one,
2-(5-hydroxy-2-methoxyphenyl)-6-morpholinoquinolin-4-one,
2-(5-hydroxy-2-methoxyphenyl)-6-pyrrolidinoquinolin-4-one,
2-(4-hydroxy-3-methoxyphenyl)-6-pyrrolidinoquinolin-4-one, 2-(2,5-dihydroxy-phenyl)-6-morpholinoquinolin-4-one,
2-(2,5dihydroxy-phenyl)-6-pyrrolidinoquinolin-4-one,
Dibenzyl 3-(4-oxo-6-(pyrrolidin-1-yl)-1,4-dihydroquinolin-2-yl)phenyl phosphate, and
3-(4-Oxo-6-(pyrrolidin-1-yl)-1,4-dihydroquinolin-2-yl)phenyl dihydrogen phosphate.
8. The compound of claim 6, wherein the compound is selected from the group consisting of
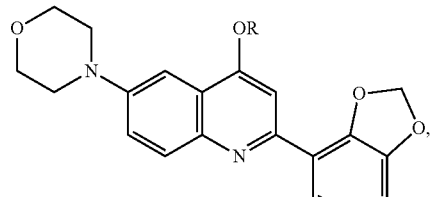,
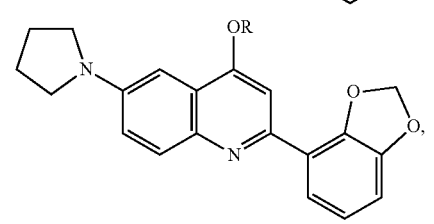,
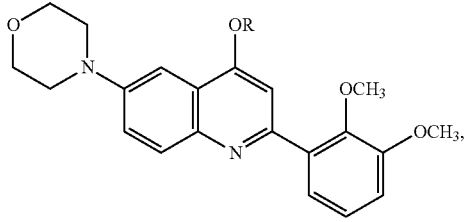,
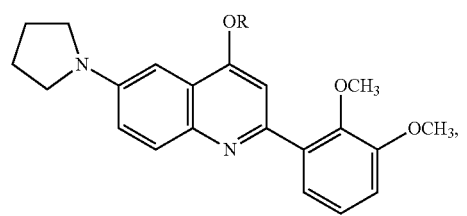,
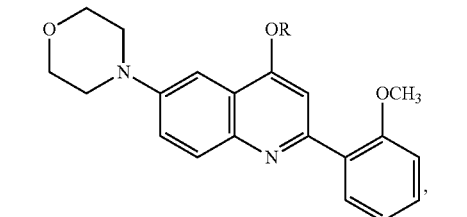,
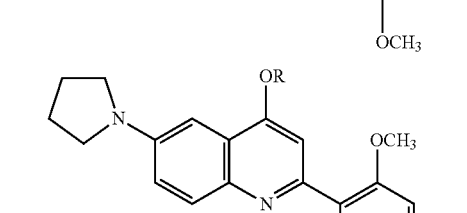,
-continued
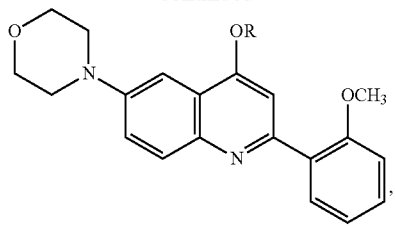,
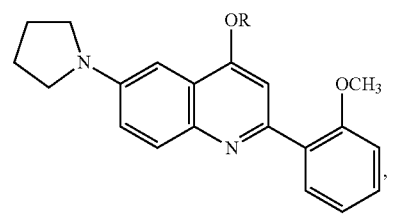,
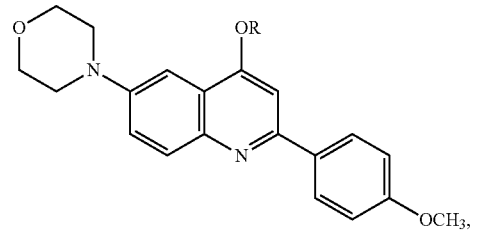,
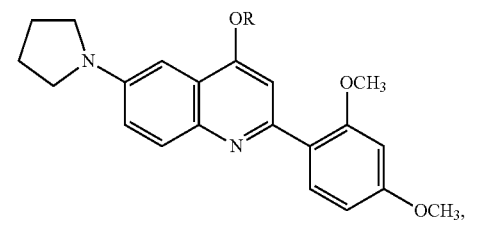,
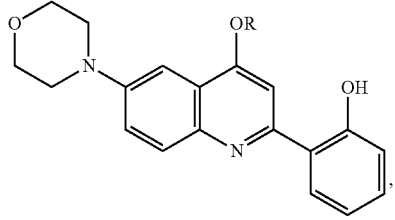,
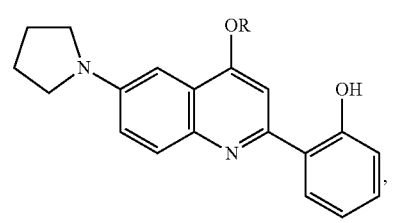,
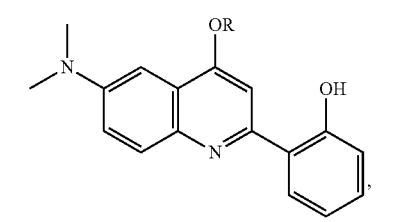,

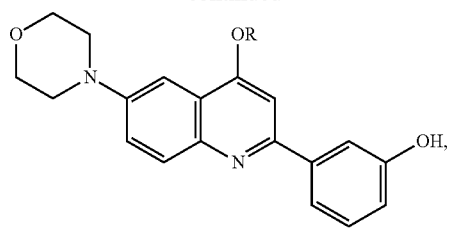
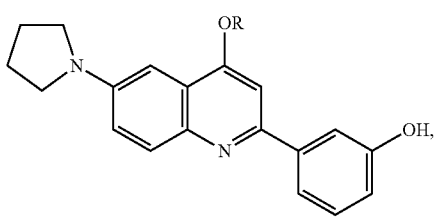
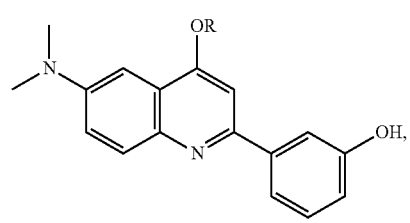
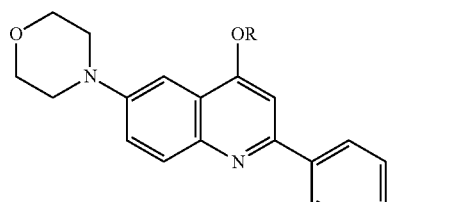
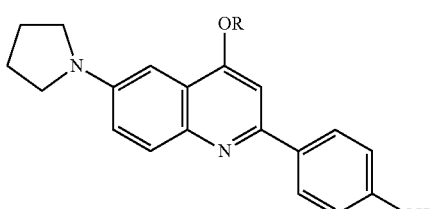
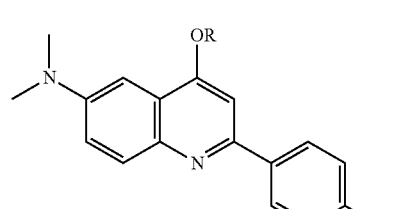
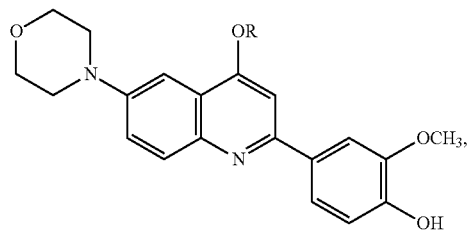
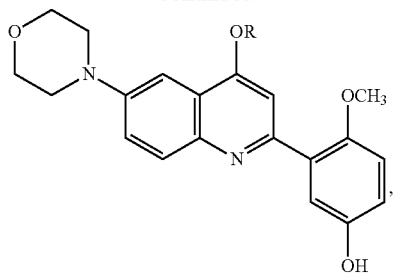
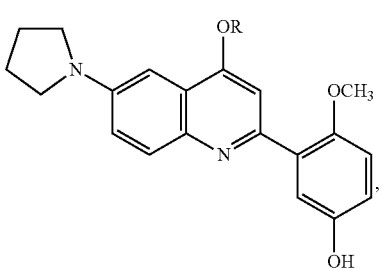
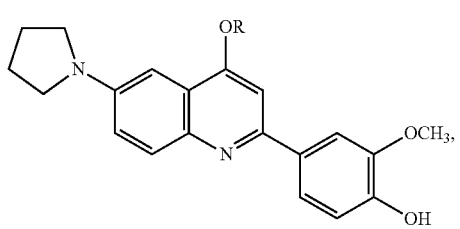
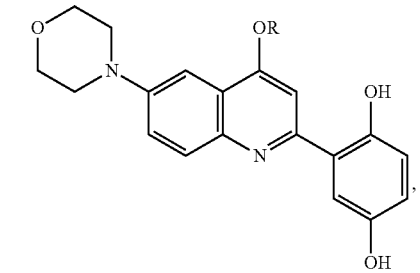
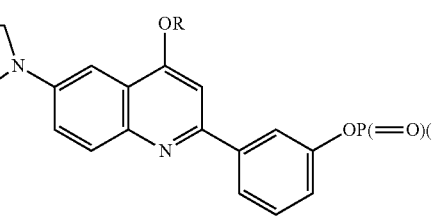
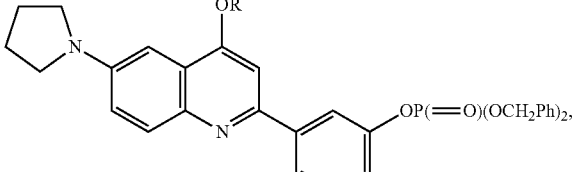
and
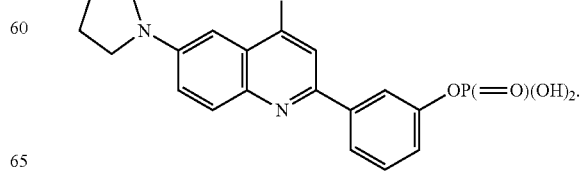

9. A compound of Formula I:

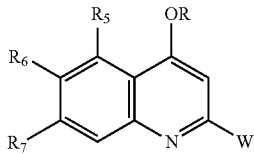

Formula I or pharmaceutically acceptable salt, thereof, wherein:

R is hydrogen;

W is 2-halophenyl, 3-halophenyl, 4-halophenyl;

$R_5$ and $R_6$ are $(C_1-C_{18})$alkylenedioxy provided that $R_7$ is hydrogen; and $R_8$ is hydrogen.

10. The compound of claim 9, wherein:

R is hydrogen;

W is 2-fluorophenyl, 3-fluorophenyl, 4-fluorophenyl;

$R_5$ and $R_6$ are methylenedioxy provided that $R_7$ is hydrogen; and $R_8$ is hydrogen.

11. The compound of claim 10, wherein the compound is selected from the group consisting of 2-(2-Fluorophenyl)-5,6-methylenedioxyquinolin-4-one, 2-(3-Fluorophenyl)-5,6-methylenedioxyquinolin-4-one, and 2-(4-Fluorophenyl)-5,6-methylenedioxyquinolin-4-one.

12. The compound of claim 10, wherein the compound is selected from the group consisting of

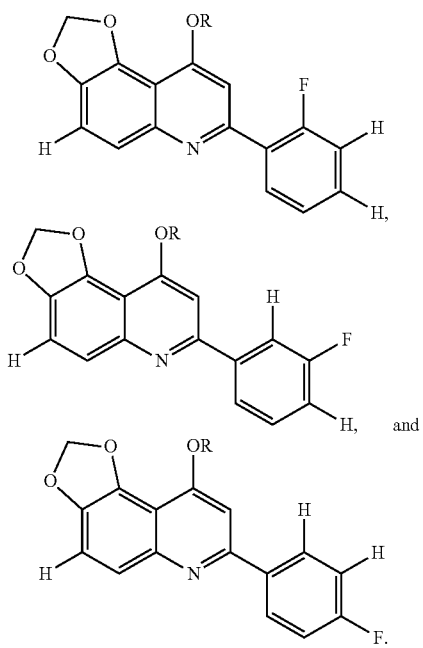

and

13. A compound of Formula I:

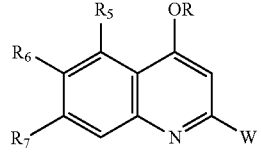

Formula I or pharmaceutically acceptable salt thereof, wherein:

R is hydrogen, $P(=O)(OH)_2$, $P(=O)(O-(C_1-C_{18})$alkylenephenyl$)_2$,

W is naphtha-1-yl, naphtha-2-yl, quinolin-2-yl, quinolin-3-yl, anthracen-1-yl, benzo[b]furan-3-yl, benzo[b]thiophen-3-yl, benzo[b]thiophen-2-yl, 3-([bis-[(($C_1$-$C_{18}$)alkylenephenyl)oxy]]phosphoryl)oxy-5-($C_1$-$C_{18}$) alkoxy phenyl, 3-(dihydrogen)phosphate-5-($C_1$-$C_{18}$) alkoxy phenyl; and $R_6$ and $R_7$ are $(C_1-C_{18})$alkylenedioxy provided that $R_5$ is hydrogen.

14. The compound of claim 13, wherein:

R is hydrogen, $P(=O)(OH)_2$, $P(=O)(O$-benzyl$)_2$,

W is naphtha-1-yl, naphtha-2-yl, quinolin-2-yl, quinolin-3-yl, quinolin-5-yl, anthracen-1-yl, benzo[b]furan-3-yl, benzo[b]thiophen-3-yl, benzo[b]thiophen-2-yl, 3-([bis-[(benzyl)oxy]]phosphoryl)oxy-5-methoxyphenyl, 3-(dihydrogen)phosphate-5-methoxyphenyl, and $R_6$ and $R_7$ are methylenedioxy provided that $R_5$ is hydrogen.

15. The compound of claim 13, wherein the compound is selected from the group consisting of Dibenzyl 2-(1-naphthalenyl)-6,7-methylenedioxyquinolin-4-yl phosphate, 2-(1-Naphthalenyl)-6,7-methylenedioxyquinolin-4-yl dihydrogen phosphate, Dibenzyl 2-(3-benzo[b]furyl)-6,7-methylenedioxyquinolin-4-yl phosphate, 2-(3-Benzo[b]furyl)-6,7-methylenedioxyquinolin-4-yl dihydrogen phosphate, 2-(3-Hydroxy-5-methoxyphenyl)-6,7-methylenedioxyquinolin-4-one, Dibenzyl 2-(3-([bis-[(benzyl)oxy]]phosphoryl)oxy-5-methoxyphenyl) -6,7-methylenedioxyquinolin-4-yl phosphate, 2-(3-([bis-[(benzyl)oxy]]phosphoryl)oxy-5-methoxyphenyl)-6,7-methylenedioxyquinolin-4-one, 2-(3-(dihydrogen)phosphate-5-methoxyphenyl)-6,7-methylenedioxyquinolin-4-one, 2(1-Naphthalenyl)-6,7-methylenedioxyquinolin-4-one, 2-(3-Benzo[b]furyl)-6,7-methylenedioxyquinolin-4-one, 2-(3-Benzo[b]thienyl)-6,7-methylenedioxyquinolin-4-one, 2-(2-Benzo[b]thienyl)-6,7-methylenedioxyquinolin-4-one, 2-(2-Benzo[b]furyl)-6,7-methylenedioxyquinolin-4-one, 2-(2-Naphthalenyl)-6,7-methylenedioxyquinolin-4-one, 2-(4-Quinolinyl)-6,7-methylenedioxyquinolin-4-one, 2-(3-Quinolinyl)-6,7-methylenedioxyquinolin-4-one, 2-(2-Quinolinyl)-6,7-methylenedioxyquinolin-4-one, 2-(5-Quinolinyl)-6,7-methylenedioxyquinolin-4-one, and 2-(1-Anthracenyl)-6,7-methylenedioxyquinolin-4-one.

16. The compound of claim 13, wherein the compound is selected from the group consisting of 111
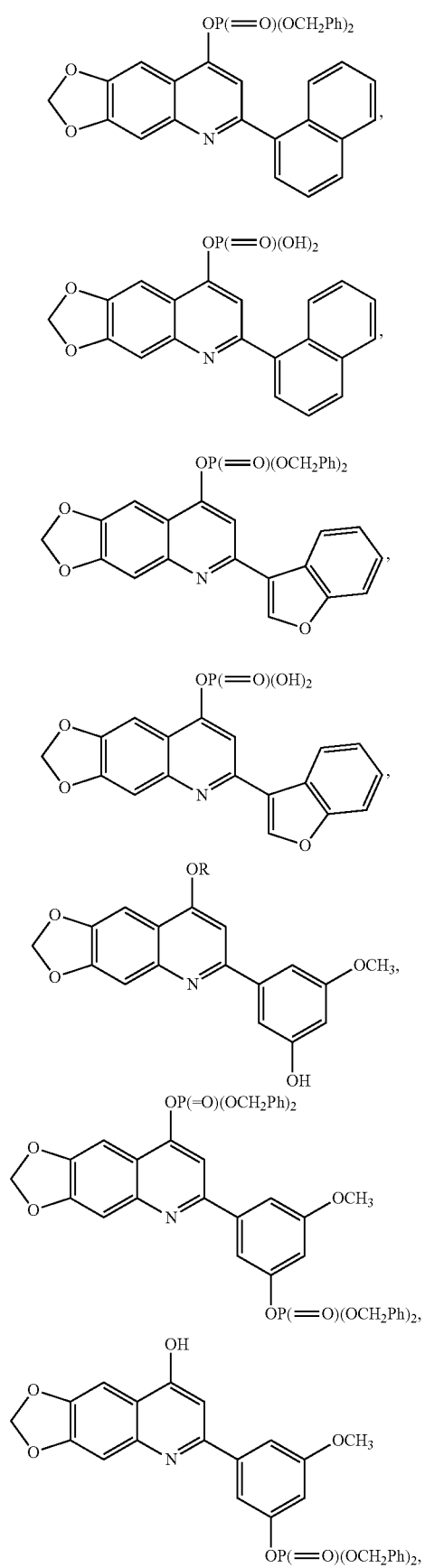
112
-continued
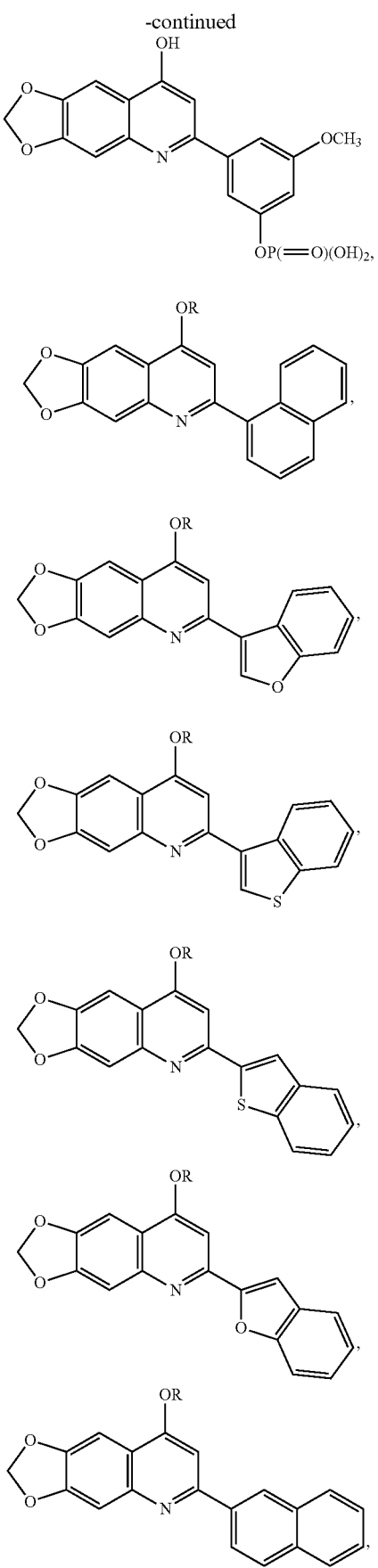

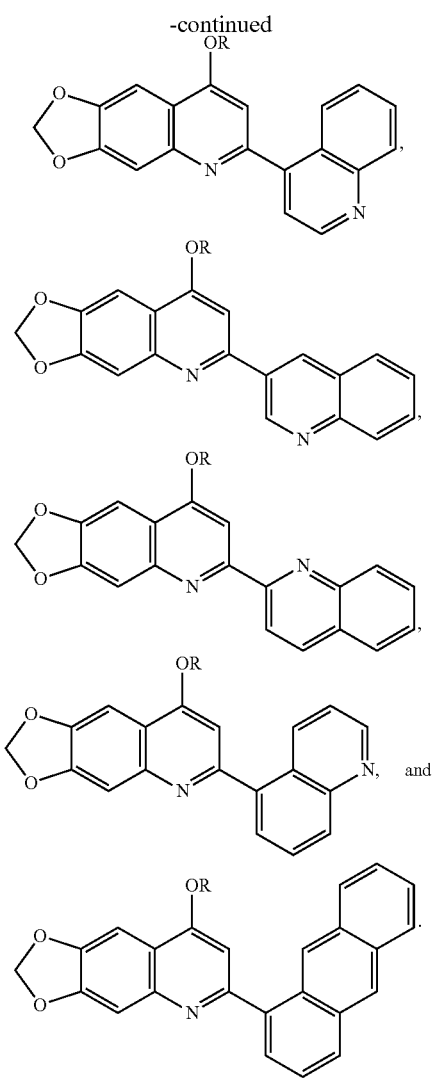

17. A method of treating cancer in a subject in need thereof, comprising administering to the subject an effective amount of a composition comprising the compound of claim 1 or a pharmaceutically acceptable salt thereof, and a pharmaceutically acceptable carrier.

18. The method of claim 17, wherein the cancer is at least one selected from the group consisting of lung cancer, colon cancer, breast cancer, liver cancer, prostate cancer, ovarian cancer, leukemia, lymphoma, pancreatic cancer, skin cancer, brain tumor, kidney cancer, bladder cancer, esophagus cancer, gastric cancer, head and neck cancer, cervical cancer, endometrial cancer, thyroid cancer, bone cancer, and soft tissue sarcoma.

19. A process for preparing a compound of Formula I

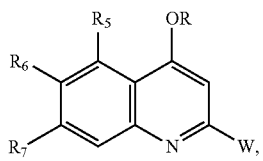

Formula I (i) wherein
R is hydrogen;
W is 2-fluorophenyl, 3-fluorophenyl, 4-fluorophenyl, benzo[d][1,3]dioxol-4-yl, 2,3-dimethoxyphenyl, 2,5-dimethoxyphenyl, 2-methoxyphenyl, 4-metboxyphenyl, 2-hydroxyphenyl, 3-hydroxyphenyl, 4-hydroxyphenyl, 2-benzyloxyphenyl, 3-benzyoxyphenyl, 4-benzyloxyphenyl, 4-benzyloxy-3-methoxyphenyl, 3-benzyoxy-5-methoxyphenyl, 4-hydroxy-3-methoxyphenyl, 5-hydroxy-2-methoxyphenyl, 2,5-dihydroxyphenyl, benzo[b]furan-3-yl, or naphtha-1-yl;
$R_5$ is methoxy, hydroxyl, or $OR_8$, or $R_5$ and $R_6$ are methylenedioxy provided that $R_7$ is hydrogen;
$R_6$ is N,N-dimethyamino, hydroxyl, methoxy, N-morpholino, or N-pyrrolindino;
$R_7$ is hydrogen, hydroxyl, or O-benzyl; and
$R_8$ is hydrogen; or a pharmaceutically acceptable salt thereof;
(ii) or wherein
R is hydrogen;
W is 2-fluorophenyl, 3-fluorophenyl, 4-fluorophenyl, benzo[d][1,3]dioxol-4-yl, 2,3-dimethoxyphenyl, 2,5-dimethoxyphenyl, 2-methoxyphenyl, 4-methoxyphenyl, 2-hydroxyphenyl, 3-hydroxyphenyl, 4-hydroxyphenyl, 2-benzyloxyphenyl, 3-benzyloxyphenyl, 4-benzyloxphenyl, 4-benzyloxy-3-methoxyphenyl, 3-benzyloxy-5-methoxyphenyl, 4-hydroxy-3-methoxyphenyl, 5-hydroxy-2-methoxyphenyl, 2,5-dihydroxyphenyl, benzo[b]furan-3-yl, or naphtha-1-yl;
$R_5$ is hydrogen, methoxy, hydroxyl, or $OR_8$;
$R_6$ is N,N-dimethylamino, hydroxyl, methoxy, N-morpholino, or N-pyrrolindino;
$R_7$ is hydroxyl, or O-benzyl;
or $R_6$ and $R_7$ are methylenedioxy provided that $R_5$ is hydrogen; and
$R_8$ is hydrogen,
the method comprising;
ai) reacting a compound of Formula II

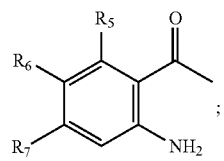

Formula II wherein $R_5$ is hydroxyl, methoxy, or $OR_8$, or $R_5$ and $R_6$ are methylenedioxy provided that $R_7$ is hydrogen;
$R_6$ is hydroxyl, N,N-dimethylamino, methoxy, N-morpholino, or N-pyrrolindino;
$R_7$ is hydrogen, halo, $OR_8$, hydroxyl, or O-benzyl; and
$R_8$ is hydrogen;
(aii) or reacting a compound of Formula II

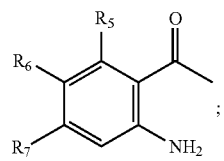

Formula II wherein
$R_5$ is hydrogen, hydroxyl, methoxy, or $OR_8$;

R$_6$ hydroxyl, N,N-dimethylamino, methoxy, N-morpholino, or N-pyrrolindino;
R$_7$ is halo, OR$_8$, hydroxyl, or O-benzyl;
or R$_6$ and R$_7$ are methylenedioxy provided that R$_5$ is hydrogen; and
R$_8$ is hydrogen;
with a compound of Formula III

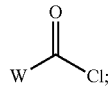

Formula III in the presence of a base; wherein W is 2-fluorophenyl, 3-fluorophenyl, 4fluorophenyl, benzo[d] [1,3]dioxol-4-yl, 2,3-dimethoxyphenyl, 2,5-dimethoxyphenyl, 2-methoxyphenyl, 4-methoxyphenyl, 2-hydroxyphenyl, 3-hydroxyphenyl, 4-hydroxyphenyl, 2-benzyloxyphenyl, 3-benzyloxyphenyl, 4-benzyloxyphenyl, 4-benzyloxy-3-methoxyphenyl, 3-benzyloxy-5-methoxyphenyl, 4-hydroxy-3-methoxyphenyl, 5-hydroxy-2-methoxyphenyl, 2,5-dihydroxyphenyl, benzo[b]furan-3-yl, or naphtha-1-yl;
to afford a compound of Formula IV

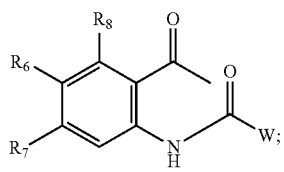

Formula IV (1) wherein
R is hydrogen;
W is 2-fluorophenyl, 3-fluorophenyl, 4-fluorophenyl, benzo[d ] [1,3]dioxol-4-yl, 2,3-dimethoxyphenyl, 2,5-dimethoxyphenyl, 2-methoxyphenyl, 4-methoxyphenyl, 2-hydroxyphenyl, 3-hydroxyphenyl, 4-hydroxyphenyl, 2-benzyloxyphenyl, 3-benzyloxvphenyl, 4-benzyloxphenyl, 4-benzyloxy-3-methoxyphenyl, 3-benzyloxy-5-methoxyphenyl, 4-hydroxy-3-methoxyphenyl, 5-hydroxy-2-methoxyphenyl, 2,5-dihydroxyphenyl, benzo[b]furan-3-yl, or naphtha-1-yl;
R$_5$ is methoxy, hydroxyl, or OR$_8$, or R$_5$ and R$_6$ are methylenedioxy provided that R$_7$ is hydrogen;
R$_6$ is N,N-dimethylamino, hydroxyl, methoxy, N-morpholino, or N-pyrrolindino;
R$_7$ is hydrogen, hydroxyl, or O-benzyl; and
R$_8$ is hydrogen;
(2) or wherein
R is hydrogen;
W is 2-fluorophenyl, 3-fluorophenyl, 4-fluorophenyl, benzo[d ] [1,3]dioxol-4-yl, 2,3-dimethoxyphenyl, 2,5-dimethoxyphenyl, 2-methoxyphenyl, 4-methoxyphenyl, 2-hydroxyphenyl, 3-hydroxyphenyl, 4-hydroxyphenyl, 2-benzyloxyphenyl, 3-benzyloxyphenyl, 4-benzyloxphenyl, 4-benzyloxy-3-methoxyphenyl, 3-benzyloxy-5-methoxyphenyl, 4-hydroxy-3-methoxyphenyl, 5-hydroxy-2-methoxyphenyl, 2,5-dihydroxyphenyl, benzo[b]furan-3-yl, or naphtha-1-yl;
R$_5$ is hydrogen, methoxy, hydroxyl, or OR$_8$,
R$_6$ is N,N-dimethydroxyl, hydroxyl, methoxy, N-morpholino, or N-pyrrolindino;
R$_7$ is hydroxyl or O-benzyl;
or R$_6$ and R$_7$ are methylenedioxy provided that R$_5$ is hydrogen; and
R$_8$ is hydrogen;
(b) and reacting the compound of Formula IV with a base to afford the compound of Formula I.
20. The process of claim 19, further comprising dealkylating the compound of Formula I to afford the compound of Formula I

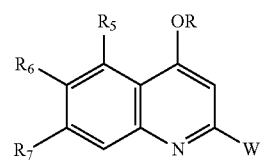

Formula I (i) wherein
R is hydrogen;
W is 2-fluorophenyl, 3-fluorophenyl, 4-fluorophenyl, benzo[d ] [1,3]dioxol-4-yl, 2,3-dimethoxyphenyl, 2,5-dimethoxyphenyl, 2-methoxyphenyl, 4-methoxyphenyl, 2-hydroxyphenyl, 3-hydroxyphenyl, 4-hydroxyphenyl, 2-benzyloxyphenyl, 3-benzyloxyphenyl, 4-benzyloxphenyl, 4-benzyloxy-3-methoxyphenyl, 3-benzyloxy-5-methoxyphenyl, 4-hydroxy-3-methoxyphenyl, 5-hydroxy-2-methoxyphenyl, 2,5-dihydroxyphenyl, benzo[b]furan-3-yl, or naphtha-1-yl;
R$_5$ is hydroxyl, or methoxy;
R$_6$ is N,N-dimethylamino, hydroxyl, methoxy, N-morpholino, or N-pyrrolindino; and
R$_7$ is hydrogen;
(ii) or wherein
R is hydrogen;
W is 2-fluorophenyl, 3-fluorophenyl, 4-fluorophenyl, benzo[d ] [1,3]dioxol-4-yl, 2,3-dimethoxyphenyl, 2,5-dimethoxyphenyl, 2-methoxyphenyl, 4-methoxyphenyl, 2-hydroxyphenyl, 3-hydroxyphenyl, 4-hydroxyphenyl, 2-benzyloxyphenyl, 3-benzyloxyphenyl, 4-benzyloxphenyl, 4-benzyloxy-3-methoxyphenyl, 3-benzyloxy-5-methoxyphenyl, 4-hydroxy-3-methoxyphenyl, 5-hydroxy-2-methoxyphenyl, 2,5-dihydroxyphenyl, benzo[b]furan-3-yl, or naphtha-1-yl;
R$_5$ is hydrogen, hydroxyl, or methoxy;
R$_6$ is N,N-dimethylamino, hydroxyl, N-morpholino, or N-pyrrolindino, provided that R$_7$ is hydrogen, or R$_6$ and R$_7$ are methylenedioxy provided that R$_5$ is hydrogen.

* * * * *